US008110572B2

(12) United States Patent
Dai et al.

(10) Patent No.: US 8,110,572 B2
(45) Date of Patent: Feb. 7, 2012

(54) INHIBITORS OF PROTEIN KINASES

(75) Inventors: Yujia Dai, Gurnee, IL (US); Zhiqin Ji, Libertyville, IL (US); Michael R. Michaelides, Libertyville, IL (US)

(73) Assignee: Abbott Laboratories, Abbott Park, IL (US)

( * ) Notice: Subject to any disclaimer, the term of this patent is extended or adjusted under 35 U.S.C. 154(b) by 500 days.

(21) Appl. No.: 12/174,334

(22) Filed: Jul. 16, 2008

(65) Prior Publication Data

US 2009/0054430 A1    Feb. 26, 2009

Related U.S. Application Data

(60) Provisional application No. 60/949,886, filed on Jul. 16, 2007.

(51) Int. Cl.
| | | |
|---|---|---|
| *A61K 31/423* | (2006.01) | |
| *A61K 31/416* | (2006.01) | |
| *A61K 31/5377* | (2006.01) | |
| *C07D 261/20* | (2006.01) | |
| *C07D 231/56* | (2006.01) | |
| *C07D 413/02* | (2006.01) | |

(52) U.S. Cl. ............... 514/233.8; 514/254.04; 514/379; 514/403; 544/137; 544/368; 548/241; 548/362.1

(58) Field of Classification Search ........................ None
See application file for complete search history.

(56) References Cited

U.S. PATENT DOCUMENTS

| 6,677,369 B2 * | 1/2004 | Beight et al. .................. 514/447 |
| 2004/0235892 A1 | 11/2004 | Dai et al. |
| 2005/0020603 A1 | 1/2005 | Dai et al. |
| 2006/0178378 A1 | 8/2006 | Dai et al. |

FOREIGN PATENT DOCUMENTS

| WO | 03078402 | 9/2003 |
| WO | 03097610 | 11/2003 |

OTHER PUBLICATIONS

Sally A. Amundson et al., *An Informatics Approach Identifying Markers of Chemosensitivity in Human Cancer Cell Lines*, Cancer Research 60: 6101-6110 (Nov. 2000).
Kasumi Araki et al., *High Expression of Aurora-B/Aurora and Ipl1-like midbody-associated protein (AIM-1) in astrocytomas*, Journal of Neuro-Oncology 67: 53-64 (2004).
James R. Bischoff et al., *A homologue of Drosophila aurora kinase is oncogenic and amplified in human colorectal cancers*, The EMBO Journal 17(11): 3052-3065 (1998).
Sigridur K. Bodvarsdottir et al., *Aurora-A amplification associated with BRCA2 mutation in breast tumours*, Cancer Letters 248: 96-102 (2007).
Jinyun Chen et al., *Association Between Aurora-A Kinase Polymorphisms and Age of Onset of Hereditary Nonpolyposis Colorectal Cancer in a Caucasian Population*, Molecular Carcinogenesis 46: 249-256 (2007).
Paolo Chieffi et al., *Aurora B expression Directly Correlates With Prostate Cancer Malignancy and Influence Prostate Cell Proliferation*, The Prostate 66: 326-333 (2006).
E. Comperat et al., *Aurora-A/STK-15 is a predictive factor for recurrent behaviour in non-invasive bladder carcinoma: a study of 128 cases of non-invasive neoplasms*, Virchows Arch 450: 419-424 (2007).
David G. Cox et al., *Polymorphisms of the AURKA (STK15/Aurora kinase) gene and breast cancer risk* (United States), Cancer Causes and Control 17: 81-83 (2006).
Amanda Ewart-Toland et al., *Aurora-A/STK15 Tρ91A is a general low penetrance cancer susceptibility gene: a meta-analysis of multiple cancer*, Carcinogenesis 26(8): 1368-1373 (2005).
Amanda Ewart-Toland et al., *Identification of Stk6/STK15 as a candidate low-penetrance tumor-susceptibility gene in mouse and human*, Nature Genetics 34(4) 403-412 (2003).
Gail C. Fraizer et al., *Aurora-A/STK15/BTAK enhances chromosomal instability in bladder cancer cells*, International Journal of Oncology 25: 1631-1639 (2004).
Jian Gu et al., *Polymorphisms of STK15 (Aurora-A) gene and lung cancer risk in Caucasians*, Carcinogenesis 28(2): 350-355 (2007).
Truija Hienonen et al., *Preferential amplification of AURKA 91A (Ile31) in familial colorectal cancers*, Intl J Cancer 118: 505-508 (2006).
Eliska Holzelova et al., *Autoimmune Lymphoproliferative Syndrome with Somatic Fas Mutations*, The New England Journal of Medicine 351: 1409-1418 (2004).
Ashraful Hoque et al., *Loss of Aurora A/STK15/BTAK Overexpression Correlates with Transition of in Situ to Invasive Ductal Carcinoma of the Breast*, Cancer Epidemiology Biomarkers & Prevention 12: 1518-1522 (2003).
Hyoungseok Ju et al., *Functional polymorphism 57ValOlle of aurora kinase A associated with increased risk of gastric cancer progression*, Cancer Letters 242: 273-279 (2006).
Nicholas Keen et al., *Aurora-Kinase Inhibitors as Anticancer Agents*, Nature Reviews 4: 927-936 (Dec. 2004).
Makoto T. Kimura et al., *Two Functional Coding Single Nucleotide Polymorphisms in STK15 (Aurora-A) Coordinately Increase Esophageal Cancer Risk*, Cancer Research 65(9): 3548-3554 (2005).
Alexandra Klein et al., *Overexpression and amplification of STK15 in human gliomas*, International Journal of Oncology 25: 1789-1794 (2004).
Toshifumi Kurahashi et al., *Significance of Aurora-A expression in renal cell carcinoma*, Urologic Oncology 25: 128-133 (2007).
Charles N. Landen et al., *Overexpression of the Centrosomal Protein Aurora-A Kinase is Associated with Poor Prognosis in Epithelial Ovarian Cancer Patients*, Clinical Cancer Research 13(14): 4098-4104 (Jul. 15, 2007).
Silke Lassmann et al., *PredictiveValue of Aurora-A/STK15 Expression for Late Stage Epithelial Ovarian Cancer Patients Treated by Adjuvant Chemotherapy*, Clinical Cancer Research 13(14): 4083-4091 (Jul. 15, 2007).
Donghui Li et al., *Overexpression of Oncogenic STK15/BTAK/Aurora A Kinase in Human Pancreatic Cancer*, Clinical Cancer Research 9: 991-997 (2003).
Yong-Shiang Li et al., *Gene Expression Profiles of the Aurora Family Kinases*, Gene Expressions 13: 15-26.
Yen-Li Lo et al., *Breast cancer risk associated with genotypic polymorphism of the mitosis-regulating gene Aurora-A/STK15/BTAK*, Intl J Cancer 115: 276-283 (2005).
Yung-Ming Jeng et al., *Overexpression and Amplification of Aurora-A in Hepatocellular Carcinoma*, Clinical Cancer Research 10: 2065-2071 (Mar. 15, 2004).

(Continued)

*Primary Examiner* — Kamal Saeed
(74) *Attorney, Agent, or Firm* — Susan L. Steele

(57) ABSTRACT

Compounds that inhibit Aurora-kinases, compositions containing the compounds and methods of treating diseases using the compounds are disclosed.

15 Claims, No Drawings

OTHER PUBLICATIONS

Yasuo Miyoshi et al., *Association of Centrosomal Kinase STK15/BTAK MRNA Expression With Chromosomal Instability in Human Breast Cancers*, Intl J Cancer 92: 370-373 (2001).

Gema Moreno-Bueno et al., *Differential Gene Expression Profile in Endometrioid and Nonendometrioid Endometrial Carcinoma: STK15 is Frequently Overexpressed and Amplified in Nonendometrioid Carcinomas*, Cancer Research 63: 5697-5702 (Sep. 15, 2003).

Kai Neben et al., *Microarray-Based Screening for Molecular Markers in Medulloblastoma Revealed STK15 as Independent Predictor for Survival*, Cancer Research 64: 3101-3111 (May 1, 2004).

Naoshi Nishida et al., *High Copy Amplification of the Aurora-A Gene is Associated with Chromosomal Instability Phenotype in Human Colorectal Cancers*, Cancer Biology & Therapy 6(4): e1-e9 (2007).

Jennifer M. Puck et al., *Immune Disorders Caused by Defects in the Caspase Cascade*, Current Allergy and Asthma Reports 3: 378-384 (2003).

Guangying Qi et al., *Aurora-B expression and its correlation with cell proliferation and metastasis in oral cancer*, Virchows Arch 450: 297-302 (2007).

Wilfred Reichardt et al., *The putative serine/threonine kinase gene STK15 on chromosome 20q13.2 is amplified in human gliomas*, Oncology Reports 10: 1275-1279 (2003).

Rudolf Reiter et al., *Aurora KinaseA Messenger RNA Overexpression is Correlated with Tumor Progression and Shortened Survival in Head and NeckS quamous Cell Carcinoma*, Clinical Cancer Research 6(12): 5136-5141 (Sep. 1 2006).

Ramesh Rengan et al., *Actin cytoskeletal function is spared, but apoptosis is increased, in WAS patient hematopoietic cells*, Blood 95: 1283-1292 (2000).

Melanie E. Royce et al., *STK15/Aurora-A Expression in Primary Breast Tumors is Correlated with Nuclear Grade but Not with Prognosis*, Cancer 100(1): (Jan. 1, 2004).

Subrata Sen et al., *Amplification/Overexpression of a Mitotic Kinase Gene in Human Bladder Cancer*, J of the National Cancer Institute 94(17): 1320-1329 (Sep. 4, 2002).

Subrata Sen et al., *A putative serine/threonine kinase encoding gene BTAK on chromosome 20q13 is ampli® ed and overexpressed in human breast cancer cell lines*, Oncogene 14: 2195-2200 (1997).

K. Shimazaki et al., *Evaluation of apoptosis as a prognostic factor in myelodysplastic syndromes*, British Journal of Haematology 110: 584-590 (2000).

SL Smith et al., *Overexpression of aurora B kinase (AURKB) in primary non-small cell lung carcinoma is frequent, generally driven from one allele, and correlates with the level of genetic instability*, British Journal of Cancer 93: 719-729 (2005).

Rosanna Sorrentino et al., *Aurora B Overexpression Associates with the Thyroid Carcinoma Undifferentiated Phenotype and is Required for Thyroid Carcinoma Cell Proliferation*, Journal of Clinical Endocrinology & Metabolism 90(2): 928-935 (2005).

Takuji Tanaka et al., *Centrosomal Kinase AIK1 is Overexpressed in Invasive Ductal Carcinoma of the Breast*, Cancer Research 59: 6041-2044 (May 1, 1999).

Masaaki Tatsuka et al., *Overexpression of Aurora-A potentiates HRAS-mediated oncogenic transformation and is implicated in oral carcinogenesis*, Oncogene 24: 1122-1127 (2005).

Sandrine Tchatchou et al., *Aurora kinases A and B and familial breast cancer risk*, Cancer Letters 247: 266-272 (2007).

Tong Tong et al., Overexpression of Aurora-A Contributes to Malignant Development of Human Esophageal Squamous Cell Carcinoma, Clinical Cancer Research 10: 7304-7310 (Nov. 1, 2004).

Linda Vidarsdottir et al., *Breast cancer risk associated with AURKA 91T A polymorphism in relation to BRCA mutations*, Cancer Letters 250: 206-212 (2007).

Barbara Vischioni et al., *Frequent overexpression of aurora B kinase, a novel drug target, in non-small cell lung carcinoma patients*, Mol Cancer Ther 5(11): 2905-2913 (2006).

Elisabeth Walsby et al., *Effects of the aurora kinase inhibitors AZD1152-HQPA and ZM447439 on growth arrest and polyploidy in acute myeloid leukemia cell lines and primary blasts*, Haermatologica 93(5): 662-669 (2005).

Hong-Tao Xu et al., *Expression of serine threonine kinase 15 is associated with poor differentiation in lung squamous cell carcinoma and adenocarcinoma*, Pathology International 56: 375-380 (2006).

Shang-Bin Yang et al., *Amplification and overexpression of Aurora-A in esophageal squamous cell carcinoma*, Oncology Reports 17: 1083-1088 (2007).

Weifen F Zeng et al., *Aurora B expression correlates with aggressive behaviour in glioblastoma multiforme*, J Clin Pathol 60: 218-221 (2007).

Zhonghua Thong Liu et al., Chin J Oncol 27(3) (2005).

Zhonghua Zhong Liu et al., Natl J Med China 83(4) (Feb. 25, 2003).

Jijiang Zhu et al., *AURKA amplification, chromosome instability, and centrosome abnormality in human pancreatic*, Cancer Genetics and Cytogenetics 159: 10-17 (2005).

T. Zincke et al., Justus Liebig'S Der Chemie 427: 221-255 (1922).

PCT International Search Report WO2009012312, Date of Mailing Nov. 18, 2008.

\* cited by examiner

INHIBITORS OF PROTEIN KINASES

This application claims priority to U.S. Provisional Patent Application Ser. No. 60/949,886 filed Jul. 16, 2007.

FIELD OF THE INVENTION

This invention pertains to compounds that inhibit protein kinases such as Aurora-kinases, compositions containing the compounds and methods of treating diseases using the compounds.

BACKGROUND OF THE INVENTION

Mitosis is a process by which a complete copy of a duplicated genome is segregated by the microtuble spindle apparatus into two daughter cells. Aurora-kinases, key mitotic regulators required for genome stability, have been found to be overexpressed in human tumors. There is therefore an existing need in the therapeutic arts for compounds which inhibit Aurora-kinases, compositions comprising the inhibitors and methods of treating diseases during which Aurora-kinases are unregulated or overexpressed.

SUMMARY OF THE INVENTION

One embodiment of this invention, therefore, pertains to compounds that inhibit Aurora-kinases, the compounds having Formula I

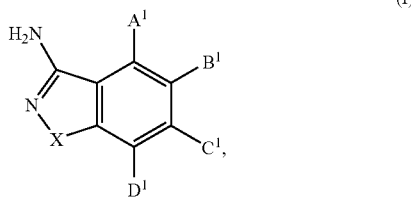

and therapeutically acceptable salts, prodrugs and salts of prodrugs thereof, wherein X is S, O or $NG^1$;

$G^1$ is H or is alkyl, alkenyl or alkynyl, each of which is unsubstituted or substituted with one, two, three, four or five of independently selected $R^6$, $OR^6$, $NH_2$, $NHR^6$, $N(R^6)_2$, OH or (O);

at least one of $A^1$, $B^1$, $C^1$, and $D^1$ is $R^1$, $C(O)NHR^1$, $C(O)N(R^1)_2$, $NHC(O)R^1$, $NR^1C(O)R^1$, $NHC(O)NHR^1$, $NHC(O)N(R^1)_2$, $NR^1C(O)NHR^1$, $NR^1C(O)N(R^1)_2$, $SO_2NHR^1$, $SO_2N(R^1)_2$, $NHSO_2R^1$, $NR^1SO_2R^1$, $OC(O)OR^1$, $NHC(O)OR^1$, $NR^1C(O)OR^1$, $OR^1$ or $SR^1$; and the remainder are independently selected H, F, Br, Cl or I;

$R^1$ is $R^2$, $R^3$, $R^4$ or $R^5$;

$R^2$ is phenyl which is unfused or fused with benzene, heteroarene or $R^{2A}$; $R^{2A}$ is cycloalkane, cycloalkene, heterocycloalkane or heterocycloalkene;

$R^3$ is heteroaryl which is unfused or fused with benzene, heteroarene or $R^{3A}$; $R^{3A}$ is cycloalkane, cycloalkene, heterocycloalkane or heterocycloalkene;

$R^4$ is cycloalkyl, cycloalkenyl, heterocycloalkyl or heterocycloalkenyl, each of which is unfused or fused with benzene, heteroarene or $R^{4A}$; $R^{4A}$ is cycloalkane, cycloalkene, heterocycloalkane or heterocycloalkene;

$R^5$ is alkyl, alkenyl or alkynyl, each of which is unsubstituted or substituted with one, two, three, four or five of independently selected $R^6$, $OR^6$, $SR^6$, $S(O)R^6$, $SO_2R^6$, $CO(O)R^6$, $OC(O)R^6$, $OC(O)OR^6$, $NH_2$, $NHR^6$, $N(R^6)_2$, $NHC(O)R^6$, $NR^6C(O)R^6$, $NHS(O)_2R^6$, $NR^6S(O)_2R^6$, $NHC(O)OR^6$, $NR^6C(O)OR^6$, $NHC(O)NH_2$, $NHC(O)NHR^6$, $NHC(O)N(R^6)_2$, $NR^6C(O)NHR^6$, $NR^6C(O)N(R^6)_2$, $C(O)NH_2$, $C(O)NHR^6$, $C(O)N(R^6)_2$, $C(O)NHOH$, $C(O)NHOR^6$, $C(O)NHSO_2R^6$, $C(O)NR^6SO_2R^6$, $SO_2NH_2$, $SO_2NHR^6$, $SO_2N(R^6)_2$, $C(O)OH$, $C(N)NH_2$, $C(N)NHR^6$, $C(N)N(R^6)_2$, $CNOH$, $CNOCH_3$, OH, (O), CN, $N_3$, $NO_2$, $CF_3$, $CF_2CF_3$, $OCF_3$, $OCF_2CF_3$, F, Cl, Br or I;

$R^6$ is $R^7$, $R^8R^9$ or $R^{9B}$;

$R^7$ is phenyl which is unfused or fused with benzene, heteroarene or $R^{7A}$; $R^{7A}$ is cycloalkane, cycloalkene, heterocycloalkane or heterocycloalkene;

$R^8$ is heteroaryl which is unfused or fused with benzene, heteroarene or $R^{8A}$; $R^{8A}$ is cycloalkane, cycloalkene, heterocycloalkane or heterocycloalkene;

$R^9$ is cycloalkyl, cycloalkenyl, heterocycloalkyl or heterocycloalkenyl, each of which is unfused or fused with benzene, heteroarene or $R^{9A}$; $R^{9A}$ is cycloalkane, cycloalkene, heterocycloalkane or heterocycloalkene;

$R^{9B}$ is alkyl, alkenyl or alkynyl;

wherein each foregoing cyclic moiety is independently unsubstituted or substituted with one or two or three or four or five of independently selected $R^{10}$, $OR^{10}$, $SR^{10}$, $S(O)R^{10}$, $SO_2R^{10}$, $C(O)R^{10}$, $CO(O)R^{10}$, $OC(O)R^{10}$, $OC(O)OR^{10}$, $NH_2$, $NHR^{10}$, $N(R^{10})_2$, $NHC(O)R^{10}$, $NR^{10}C(O)R^{10}$, $NHS(O)_2R^{10}$, $NR^{10}S(O)_2R^{10}$, $NHC(O)OR^{10}$, $NR^{10}C(O)OR^{10}$, $NHC(O)NH_2$, $NHC(O)NHR^{10}$, $NHC(O)N(R^{10})_2$, $NR^{10}C(O)NHR^{10}$, $NR^{10}C(O)N(R^{10})_2$, $C(O)NH_2$, $C(O)NHR^{10}$, $C(O)N(R^{10})_2$, $C(O)NHOH$, $C(O)NHOR^{10}$, $C(O)NHSO_2R^{10}$, $C(O)NR^{10}SO_2R^{10}$, $SO_2NH_2$, $SO_2NHR^{10}$, $SO_2N(R^{10})_2$, $C(O)H$, $C(O)OH$, $C(N)NH_2$, $C(N)NHR^{10}$, $C(N)N(R^{10})_2$, $CNOH$, $CNOCH_3$, OH, (O), CN, $N_3$, $NO_2$, $CF_3$, $CF_2CF_3$, $OCF_3$, $OCF_2CF_3$, F, Cl, Br or I;

$R^{10}$ is $R^{11}$, $R^{12}$, $R^{13}$ or $R^{14}$;

$R^{11}$ is phenyl which is unfused or fused with benzene, heteroarene or $R^{11A}$; $R^{11A}$ is cycloalkane, cycloalkene, heterocycloalkane or heterocycloalkene;

$R^{12}$ is heteroaryl which is unfused or fused with benzene, heteroarene or $R^{12A}$; $R^{12A}$ is cycloalkane, cycloalkene, heterocycloalkane or heterocycloalkene;

$R^{13}$ is cycloalkyl, cycloalkenyl, heterocycloalkyl or heterocycloalkenyl, each of which is unfused or fused with benzene, heteroarene or $R^{13A}$; $R^{13A}$ is cycloalkane, cycloalkene, heterocycloalkane or heterocycloalkene;

$R^{14}$ is alkyl, alkenyl or alkenyl, each of which is unsubstituted or substituted with one, two, three, four or five of independently selected $R^{15}$, $OR^{15}$, $SR^{15}$, $S(O)R^{15}$, $SO_2R^{15}$, $CO(O)R^{15}$, $OC(O)R^{15}$, $OC(O)OR^{15}$, $NH_2$, $NHR^{15}$, $N(R^{15})_2$, $NHC(O)R^{15}$, $NR^{15}C(O)R^{15}$, $NHS(O)_2R^{15}$, $NR^{15}S(O)_2R^{15}$, $NHC(O)OR^{15}$, $NR^{15}C(O)OR^{15}$, $NHC(O)NH_2$, $NHC(O)NHR^{15}NHC(O)N(R^{15})_2$, $NR^{15}C(O)NHR^{15}$, $NR^{15}C(O)N(R^{15})_2$, $C(O)NH_2$, $C(O)NHR^{15}$, $C(O)N(R^{15})_2$, $C(O)NHOH$, $C(O)NHOR^{15}$, $C(O)NHSO_2R^{15}$, $C(O)NR^{15}SO_2R^{15}$, $SO_2NH_2$, $SO_2NHR^{15}$, $SO_2N(R^5)_2$, $C(O)OH$, $C(N)NH_2$, $C(N)NHR^{15}$, $C(N)N(R^{15})_2$, $CNOH$, $CNOCH_3$, OH, (O), CN, $N_3$, $NO_2$, $CF_3$, $CF_2CF_3$, $OCF_3$, $OCF_2CF_3$, F, Cl, Br or I;

$R^{15}$ is $R^{16}$, $R^{17}$, $R^{18}$ or $R^{19}$;

$R^{16}$ is phenyl which is unfused or fused with benzene, heteroarene or $R^{16A}$; $R^{16A}$ is cycloalkane, cycloalkene, heterocycloalkane or heterocycloalkene;

$R^{17}$ is heteroaryl which is unfused or fused with benzene, heteroarene or $R^{17A}$; $R^{17A}$ is cycloalkane, cycloalkene, heterocycloalkane or heterocycloalkene;

$R^{18}$ is cycloalkyl, cycloalkenyl, heterocycloalkyl or heterocycloalkenyl, each of which is unfused or fused with benzene, heteroarene or $R^{18A}$; $R^{18A}$ is cycloalkane, cycloalkene, heterocycloalkane or heterocycloalkene;

$R^{19}$ is alkyl, alkenyl or alkenyl, each of which is unsubstituted or substituted with $R^{20}$;

$R^{20}$ is phenyl, heteroaryl, cycloalkyl, cycloalkenyl, heterocycloalkyl or heterocycloalkenyl;

wherein the moieties represented by $R^{11}$, $R^{12}$, $R^{13}$, $R^{16}$, $R^{17}$, $R^{18}$ and $R^{20}$ are independently unsubstituted or substituted with one or two or three of independently selected $R^{21}$, $OR^{21}$, $SR^{21}$, $S(O)R^{21}$, $SO_2R^{21}$, $C(O)R^{21}$, $CO(O)R^{21}$, $OC(O)R^{21}$, $OC(O)OR^{21}$, $NH_2$, $NHR^{21}$, $N(R^{21})_2$, $NHC(O)R^{21}$, $NR^{21}C(O)R^{21}$, $NHS(O)_2R^{21}$, $NR^{21}S(O)_2R^{21}$, $NHC(O)OR^{21}$, $NR^{21}OC(O)OR^{21}$, $NHC(O)NH_2$, $NHC(O)NHR^{21}$, $NHC(O)N(R^{21})_2$, $NR^{21}C(O)NHR^{21}$, $NR^{21}OC(O)N(R^{21})_2$, $C(O)NH_2$, $C(O)NHR^{21}$, $C(O)N(R^{21})_2$, $C(O)NHOH$, $C(O)NHOR^{21}$, $C(O)NHSO_2R^{21}$, $C(O)NR^{21}SO_2R^{21}$, $SO_2NH_2$, $SO_2NHR^{21}$, $SO_2N(R^{21})_2$, $C(O)H$, $C(O)OH$, $C(N)NH_2$, $C)NHR^{21}$, $C(N)N(R^2)_2$, CNOH, $CNOCH_3$, OH, (O), CN, $N_3$, $NO_2$, $CF_3$, $CF_2CF_3$, $OCF_3$, $OCF_2CF_3$, F, Cl, Br or I;

$R^{21}$ is alkyl, alkenyl or alkynyl, each of which is unsubstituted or substituted with one or two or three of independently selected $R^{22}$, F, Cl, Br, I, OH, C(O)OH, $NO_2$ or $NH_2$; and $R^{22}$ is phenyl, heteroaryl, cycloalkyl, cycloalkenyl or heterocycloalkyl.

Still another embodiment pertains to methods of treating diseases involving overexpression or unregulation of Aurorakinases in a mammal, the methods comprising administering thereto a therapeutically effective amount of a compound having Formula I, (I)

and therapeutically acceptable salts, prodrugs and salts of prodrugs thereof, wherein X is S, O or $NG^1$;

$G^1$ is H or is alkyl, alkenyl or alkynyl, each of which is unsubstituted or substituted with one, two, three, four or five of independently selected $R^6$, $OR^6$, $NH_2$, $NHR^6$, $N(R^6)_2$, OH or (O);

at least one of $A^1$, $B^1$, $C^1$, and $D^1$ is $R^1$, $C(O)NHR^1$, $C(O)N(R^1)_2$, $NHC(O)R^1$, $NR^1C(O)R^1$, $NHC(O)NHR^1$, $NHC(O)N(R^1)_2$, $NR^1C(O)NHR^1$, $NR^1C(O)N(R^1)_2$, $SO_2NHR^1$, $SO_2N(R^1)_2$, $NHSO_2R^1$, $NR^1SO_2R^1$, $OC(O)OR^1$, $NHC(O)OR^1$, $NR^1C(O)OR^1$, $OR^1$ or $SR^1$; and the remainder are independently selected H, F, Br, Cl or I;

$R^1$ is $R^2$, $R^3R^4$ or $R^5$;

$R^2$ is phenyl which is unfused or fused with benzene, heteroarene or $R^{2A}$; $R^{2A}$ is cycloalkane, cycloalkene, heterocycloalkane or heterocycloalkene;

$R^3$ is heteroaryl which is unfused or fused with benzene, heteroarene or $R^{3A}$; $R^{3A}$ is cycloalkane, cycloalkene, heterocycloalkane or heterocycloalkene;

$R^4$ is cycloalkyl, cycloalkenyl, heterocycloalkyl or heterocycloalkenyl, each of which is unfused or fused with benzene, heteroarene or $R^{4A}$; $R^{4A}$ is cycloalkane, cycloalkene, heterocycloalkane or heterocycloalkene;

$R^5$ is alkyl, alkenyl or alkynyl, each of which is unsubstituted or substituted with one, two, three, four or five of independently selected $R^6$, $OR^6$, $SR^6$, $S(O)R^6$, $SO_2R^6$, $CO(O)R^6$, $OC(O)R^6$, $OC(O)OR^6$, $NH_2$, $NHR^6$, $N(R^6)_2$, $NHC(O)R^6$, $NR^6C(O)R^6$, $NHS(O)_2R^6$, $NR^6S(O)_2R^6$, $NHC(O)OR^6$, $NR^6C(O)OR^6$, $NHC(O)NH_2$, $NHC(O)NHR^6$, $NHC(O)N(R^6)_2$, $NR^6C(O)NHR^6$, $NR^6C(O)N(R^6)_2$, $C(O)NH_2$, $C(O)NHR^6$, $C(O)N(R^6)_2$, $C(O)NHOH$, $C(O)NHOR^6$, $C(O)NHSO_2R^6$, $C(O)NR^6SO_2R^6$, $SO_2NH_2$, $SO_2NHR^6$, $SO_2N(R^6)_2$, C(O)OH, $C(N)NH_2$, $C(N)NHR^6$, $C(N)N(R^6)_2$, CNOH, $CNOCH_3$, OH, (O), CN, $N_3$, $NO_2$, $CF_3$, $CF_2CF_3$, $OCF_3$, $OCF_2CF_3$, F, Cl, Br or I;

$R^6$ is $R^7$, $R^8$, $R^9$ or $R^{9B}$;

$R^7$ is phenyl which is unfused or fused with benzene, heteroarene or $R^{7A}$; $R^{7A}$ is cycloalkane, cycloalkene, heterocycloalkane or heterocycloalkene;

$R^8$ is heteroaryl which is unfused or fused with benzene, heteroarene or $R^{8A}$; $R^{8A}$ is cycloalkane, cycloalkene, heterocycloalkane or heterocycloalkene;

$R^9$ is cycloalkyl, cycloalkenyl, heterocycloalkyl or heterocycloalkenyl, each of which is unfused or fused with benzene, heteroarene or $R^{9A}$; $R^{9A}$ is cycloalkane, cycloalkene, heterocycloalkane or heterocycloalkene;

$R^{9B}$ is alkyl, alkenyl or alkynyl;

wherein each foregoing cyclic moiety is independently unsubstituted or substituted with one or two or three or four or five of independently selected $R^{10}$, $OR^{10}$, $SR^{10}$, $S(O)R^{10}$, $SO_2R^{10}$, $C(O)R^{10}$, $CO(O)R^{10}$, $OC(O)R^{10}$, $OC(O)OR^{10}$, $NH_2$, $NHR^{10}$, $N(R^{10})_2$, $NHC(O)R^{10}$, $NR^{10}C(O)R^{10}$, $NHS(O)_2R^{10}$, $NR^{10}S(O)_2R^{10}$, $NHC(O)OR^{10}$, $NR^{10}C(O)OR^{10}$, $NHC(O)NH_2$, $NHC(O)NHR^{10}$, $NHC(O)N(R^{10})_2$, $NR^{10}C(O)NHR^{10}$, $NR^{10}C(O)N(R^{10})_2$, $C(O)NH_2$, $C(O)NHR^{10}$, $C(O)N(R^{10})_2$, $C(O)NHOH$, $C(O)NHOR^{10}$, $C(O)NHSO_2R^{10}$, $C(O)NR^{10}SO_2R^{10}$, $SO_2NH_2$, $SO_2NHR^{10}$, $SO_2N(R^{10})_2$, C(O)H, C(O)OH, $C(N)NH_2$, $C(N)NHR^{10}$, $C(N)N(R^{10})_2$, CNOH, $CNOCH_3$, OH, (O), CN, $N_3$, $NO_2$, $CF_3$, $CF_2CF_3$, $OCF_3$, $OCF_2CF_3$, F, Cl, Br or I;

$R^{10}$ is $R^{11}$, $R^{12}$, $R^{13}$ or $R^{14}$ $R^{11}$ is phenyl which is unfused or fused with benzene, heteroarene or $R^{11A}$; $R^{11A}$ is cycloalkane, cycloalkene, heterocycloalkane or heterocycloalkene;

$R^{12}$ is heteroaryl which is unfused or fused with benzene, heteroarene or $R^{12A}$; $R^{12A}$ is cycloalkane, cycloalkene, heterocycloalkane or heterocycloalkene;

$R^{13}$ is cycloalkyl, cycloalkenyl, heterocycloalkyl or heterocycloalkenyl, each of which is unfused or fused with benzene, heteroarene or $R^{13A}$; $R^{13A}$ is cycloalkane, cycloalkene, heterocycloalkane or heterocycloalkene;

$R^{14}$ is alkyl, alkenyl or alkenyl, each of which is unsubstituted or substituted with one, two, three, four or five of independently selected $R^{15}$, $OR^{15}$, $SR^{15}$, $S(O)R^{15}$, $SO_2R^{15}$, $CO(O)R^{15}$, $OC(O)R^{15}$, $OC(O)OR^{15}$, $NH_2$, $NHR^{15}$, $N(R^{15})_2$, $NHC(O)R^{15}$, $NR^{15}C(O)R^{15}$, $NHS(O)_2R^{15}$, $NR^{15}S(O)_2R^{15}$, $NHC(O)OR^{15}$, $NR^{15}C(O)OR^{15}$, $NHC(O)NH_2$, $NHC(O)NHR^{15}$ $NHC(O)N(R^{15})_2$, $NR^{15}C(O)NHR^{15}$, $NR^{15}C(O)N(R^{15})_2$, $C(O)NH_2$, $C(O)NHR^{15}$, $C(O)N(R^{15})_2$, $C(O)NHOH$, $C(O)NHOR^{15}$, $C(O)NHSO_2R^{15}$, $C(O)NR^{15}SO_2R^{15}$, $SO_2NH_2$, $SO_2NHR^{15}$, $SO_2N(R^{15})_2$, C(O)OH, $C(N)NH_2$, $C(N)NHR^{15}$, $C(N)N(R^{15})_2$, CNOH, $CNOCH_3$, OH, (O), CN, $N_3$, $NO_2$, $CF_3$, $CF_2CF_3$, $OCF_3$, $OCF_2CF_3$, F, Cl, Br or I;

$R^{15}$ is $R^{16}$, $R^{17}$, $R^{18}$ or $R^{19}$;

$R^{16}$ is phenyl which is unfused or fused with benzene, heteroarene or $R^{16A}$; $R^{16A}$ is cycloalkane, cycloalkene, heterocycloalkane or heterocycloalkene;

$R^{17}$ is heteroaryl which is unfused or fused with benzene, heteroarene or $R^{17A}$; $R^{17A}$ is cycloalkane, cycloalkene, heterocycloalkane or heterocycloalkene;

$R^{18}$ is cycloalkyl, cycloalkenyl, heterocycloalkyl or heterocycloalkenyl, each of which is unfused or fused with benzene, heteroarene or $R^{18A}$; $R^{18A}$ is cycloalkane, cycloalkene, heterocycloalkane or heterocycloalkene;

$R^{19}$ is alkyl, alkenyl or alkenyl, each of which is unsubstituted or substituted with $R^{20}$;

$R^{20}$ is phenyl, heteroaryl, cycloalkyl, cycloalkenyl, heterocycloalkyl or heterocycloalkenyl;

wherein the moieties represented by $R^{11}$, $R^{12}$, $R^{13}$, $R^{16}$, $R^{17}R^{18}$ and $R^{20}$ are independently unsubstituted or substituted with one or two or three of independently selected $R^{21}$, $OR^{21}$, $SR^{21}$, $S(O)R^{21}$, $SO_2R^{21}$, $C(O)R^{21}$, $CO(O)R^{21}$, $OC(O)R^{21}$, $OC(O)OR^{21}$, $NH_2$, $NHR^{21}$, $N(R^{21})_2$, $NHC(O)R^{21}$, $NR^{21}C(O)R^{21}$, $NHS(O)_2R^{21}$, $NR^{21}S(O)_2R^{21}$, $NHC(O)OR^{21}$, $NR^{21}C(O)OR^{21}$, $NHC(O)NH_2$, $NHC(O)NHR^{21}$, $NHC(O)N(R^{21})_2$, $NR^{21}C(O)NHR^{21}$, $NR^{21}C(O)N(R^2)_2$, $C(O)NH_2$, $C(O)NHR^{21}$, $C(O)N(R^{21})_2$, $C(O)NHOH$, $C(O)NHOR^{21}$, $C(O)NHSO_2R^{21}$, $C(O)NR^{21}SO_2R^{21}$, $SO_2NH_2$, $SO_2NHR^{21}$, $SO_2N(R^{21})_2$, $C(O)H$, $C(O)OH$, $C(N)NH_2$, $C(N)NHR^{21}$, $C(N)N(R^{21})_2$, CNOH, $CNOCH_3$, OH, (O), CN, $N_3$, $NO_2$, $CF_3$, $CF_2CF_3$, $OCF_3$, $OCF_2CF_3$, F, Cl, Br or I;

$R^{21}$ is alkyl, alkenyl or alkynyl, each of which is unsubstituted or substituted with one or two or three of independently selected $R^{22}$, F, Cl, Br, I, OH, C(O)OH, $NO_2$ or $NH_2$; and $R^{22}$ is phenyl, heteroaryl, cycloalkyl, cycloalkenyl or heterocycloalkyl, with or without also administering radiotherapy thereto.

Still another embodiment pertains to methods of treating bladder cancer, breast cancer, cervical cancer, colon cancer, endometrial cancer, esophageal cancer, lung cancer, ovarian cancer, pancreatic cancer, prostate cancer, rectal cancer, skin cancer, stomach cancer and thyroid cancer in a mammal, the methods comprising administering thereto a therapeutically effective amount of a compound having Formula I, with or without also administering radiotherapy thereto.

Still another embodiment pertains to compositions comprising an excipient and a therapeutically effective amount of a compound having Formula I and a therapeutically effective amount of one additional therapeutic agent or more than one additional therapeutic agent.

Still another embodiment pertains to methods of treating diseases involving overexpression or unregulation of Aurora-kinases in a mammal, the methods comprising administering thereto a therapeutically effective amount of a compound having Formula I and a therapeutically effective amount of one additional therapeutic agent or more than one additional therapeutic agent with or without also administering radiotherapy thereto.

Still another embodiment pertains to methods of treating bladder cancer, breast cancer, cervical cancer, colon cancer, endometrial cancer, esophageal cancer, lung cancer, ovarian cancer, pancreatic cancer, prostate cancer, rectal cancer, skin cancer, stomach cancer and thyroid cancer in a mammal, the methods comprising administering thereto a therapeutically effective amount of a compound having Formula I and a therapeutically effective amount of one additional therapeutic agent or more than one additional therapeutic agent, with or without also administering radiotherapy thereto.

Still another embodiment pertains to compounds
3-amino-N-(3-(((((3-fluorophenyl)amino)carbonyl)amino)methyl)phenyl)-1,2-benzisoxazole-4-carboxamide,
3-amino-N-(3-(((((2-fluorophenyl)amino)carbonyl)amino)methyl)phenyl)-1,2-benzisoxazole-4-carboxamide,
3-amino-N-(3-(((anilinocarbonyl)amino)methyl)phenyl)-1,2-benzisoxazole-4-carboxamide,
3-amino-N-(3-(((((4-(trifluoromethyl)phenyl)amino)carbonyl)amino)methyl)phenyl)-1,2-benzisoxazole-4-carboxamide,
3-amino-N-(3-(((((4-methylphenyl)amino)carbonyl)amino)methyl)phenyl)-1,2-benzisoxazole-4-carboxamide,
3-amino-N-(3-(((((2-fluoro-5-methylphenyl)amino)carbonyl)amino)methyl)phenyl)-1,2-benzisoxazole-4-carboxamide,
3-amino-N-(3-(((((3-methoxyphenyl)amino)carbonyl)amino)methyl)phenyl)-1,2-benzisoxazole-4-carboxamide,
3-amino-N-(3-(((((4-methoxyphenyl)amino)carbonyl)amino)methyl)phenyl)-1,2-benzisoxazole-4-carboxamide,
3-amino-N-(3-(((((3,4-difluorophenyl)amino)carbonyl)amino)methyl)phenyl)-1,2-benzisoxazole-4-carboxamide,
3-amino-N-(3-(((((3,5-difluorophenyl)amino)carbonyl)amino)methyl)phenyl)-1,2-benzisoxazole-4-carboxamide,
3-amino-N-(3-(((((4-fluorophenyl)amino)carbonyl)amino)methyl)phenyl)-1,2-benzisoxazole-4-carboxamide,
3-amino-N-(3-((((cyclopentylamino)carbonyl)amino)methyl)phenyl)-1,2-benzisoxazole-4-carboxamide,
3-amino-N-(3-((((cyclohexylamino)carbonyl)amino)methyl)phenyl)-1,2-benzisoxazole-4-carboxamide,
3-amino-N-(3-((((thien-2-ylamino)carbonyl)amino)methyl)phenyl)-1,2-benzisoxazole-4-carboxamide,
3-amino-N-(3-((((thien-3-ylamino)carbonyl)amino)methyl)phenyl)-1,2-benzisoxazole-4-carboxamide,
3-amino-N-(3-(((((3-methylphenyl)amino)carbonyl)amino)methyl)phenyl)-1,2-benzisoxazole-4-carboxamide,
3-amino-N-(3-(((((3,5-dimethylphenyl)amino)carbonyl)amino)methyl)phenyl)-1,2-benzisoxazole-4-carboxamide,
3-amino-N-(3-(((((3-chlorophenyl)amino)carbonyl)amino)methyl)phenyl)-1,2-benzisoxazole-4-carboxamide,
3-amino-N-(3-(((((2-(trifluoromethyl)phenyl)amino)carbonyl)amino)methyl)phenyl)-1,2-benzisoxazole-4-carboxamide,
3-amino-N-(3-(((3-methylbenzoyl)amino)methyl)phenyl)-1,2-benzisoxazole-4-carboxamide,
3-amino-N-(3-((benzoylamino)methyl)phenyl)-1,2-benzisoxazole-4-carboxamide,
3-amino-N-(3-(((phenylacetyl)amino)methyl)phenyl)-1,2-benzisoxazole-4-carboxamide,
3-amino-N-(4-((((3-fluorophenyl)amino)carbonyl)amino)phenyl)-1,2-benzisoxazole-4-carboxamide,
3-amino-N-(4-((anilinocarbonyl)amino)phenyl)-1,2-benzisoxazole-4-carboxamide,
3-amino-N-(4-((((3-(trifluoromethyl)phenyl)amino)carbonyl)amino)phenyl)-1,2-benzisoxazole-4-carboxamide,
3-amino-N-(4-(((thien-3-ylamino)carbonyl)amino)phenyl)-1,2-benzisoxazole-4-carboxamide,
3-amino-N-(4-((((4-methylphenyl)amino)carbonyl)amino)phenyl)-1,2-benzisoxazole-4-carboxamide,
3-amino-N-(4-((((3-methylphenyl)amino)carbonyl)amino)phenyl)-1,2-benzisoxazole-4-carboxamide,
3-amino-N-(4-((((2,4-difluorophenyl)amino)carbonyl)amino)phenyl)-1,2-benzisoxazole-4-carboxamide,
3-amino-N-(4-((((3,5-difluorophenyl)amino)carbonyl)amino)phenyl)-1,2-benzisoxazole-4-carboxamide,
3-amino-N-(4-((((3,4-difluorophenyl)amino)carbonyl)amino)phenyl)-1,2-benzisoxazole-4-carboxamide,
3-amino-N-(3-(((((3-fluorophenyl)amino)carbonyl)amino)methyl)phenyl)-7-methyl-1,2-benzisoxazole-4-carboxamide,
3-amino-N-(3-(((anilinocarbonyl)amino)methyl)phenyl)-7-methyl-1,2-benzisoxazole-4-carboxamide,
3-amino-N-(4-((((3-fluorophenyl)amino)carbonyl)amino)phenyl)-7-methyl-1,2-benzisoxazole-4-carboxamide,
3-amino-N-(4-((anilinocarbonyl)amino)phenyl)-7-methyl-1,2-benzisoxazole-4-carboxamide,
3-amino-N-(4-(benzoylamino)phenyl)-1,2-benzisoxazole-4-carboxamide, 3-amino-N-(3-(((((3-fluorophenyl)amino)carbonyl)amino)methyl)phenyl)-1,2-benzisothiazole-4-carboxamide, 3-amino-N-(3-(((anilinocarbonyl)amino)methyl)phenyl)-1,2-benzisothiazole-4-carboxamide, 3-amino-N-(3-(((((4-(trifluoromethyl)phenyl)amino)carbonyl)amino)methyl)phenyl)-1,2-benzisothiazole-4-carboxamide, 3-amino-N-(4-((((3-fluorophenyl)amino)carbonyl)amino)phenyl)-1,2-benzisothiazole-4-carboxamide, 3-amino-N-(4-((anilinocarbonyl)amino)phenyl)-1,2-benzisothiazole-4-carboxamide, 3-amino-N-(4-((((3-(2-hydroxyethyl)phenyl)amino)carbonyl)amino)phenyl)-1,2-benzisothiazole-4-carboxamide, 3-amino-N-(4-((((3,4-dichlorophenyl)amino)carbonyl)amino)phenyl)-1,2-benzisoxazole-4-carboxamide, 3-amino-N-(4-((((3-methoxyphenyl)amino)carbonyl)amino)phenyl)-1,2-benzisoxazole-4-carboxamide, 3-amino-N-(4-((((4-bromophenyl)amino)carbonyl)amino)phenyl)-1,2-benzisoxazole-4-carboxamide, 3-amino-N-(4-((((4-fluorophenyl)amino)carbonyl)amino)phenyl)-1,2-benzisoxazole-4-carboxamide, 3-amino-N-(4-((((4-chlorophenyl)amino)carbonyl)amino)phenyl)-1,2-benzisoxazole-4-carboxamide, 3-amino-N-(4-((((4-methoxyphenyl)amino)carbonyl)amino)phenyl)-1,2-benzisoxazole-4-carboxamide, 3-amino-N-(4-(((benzylamino)carbonyl)amino)phenyl)-1,2-benzisoxazole-4-carboxamide, 3-amino-N-(4-((((3-cyanophenyl)amino)carbonyl)amino)phenyl)-1,2-benzisoxazole-4-carboxamide, 3-amino-N-(4-((((3-(methylthio)phenyl)amino)carbonyl)amino)phenyl)-1,2-benzisoxazole-4-carboxamide, 3-amino-N-(4-((((4-(methylthio)phenyl)amino)carbonyl)amino)phenyl)-1,2-benzisoxazole-4-carboxamide, 3-amino-N-(4-(((((3-chloro-4-fluorophenyl)amino)carbonyl)amino)phenyl)-1,2-benzisoxazole-4-carboxamide, 3-amino-N-(3-(((((4-fluorophenyl)amino)carbonyl)amino)methyl)phenyl)-1H-indazole-4-carboxamide, 3-amino-N-(3-(((((3-chlorophenyl)amino)carbonyl)amino)methyl)phenyl)-1H-indazole-4-carboxamide, 3-amino-N-(3-((((((4-(trifluoromethoxy)phenyl)amino)carbonyl)amino)methyl)phenyl)-1H-indazole-4-carboxamide, 3-amino-N-(3-(((((3-methylphenyl)amino)carbonyl)amino)methyl)phenyl)-1H-indazole-4-carboxamide, 3-amino-N-(3-(((((4-(trifluoromethyl)phenyl)amino)carbonyl)amino)methyl)phenyl)-1H-indazole-4-carboxamide, 3-amino-N-(3-(((((3-(trifluoromethyl)phenyl)amino)carbonyl)amino)methyl)phenyl)-1H-indazole-4-carboxamide, 3-amino-N-(3-(((((3-fluorophenyl)amino)carbonyl)amino)methyl)phenyl)-1H-indazole-4-carboxamide, 3-amino-N-(4-((anilinocarbonyl)amino)phenyl)-1H-indazole-4-carboxamide, 3-amino-N-(4-((((3-fluorophenyl)amino)carbonyl)amino)phenyl)-1H-indazole-4-carboxamide, 3-amino-N-(3-(((((3-fluorophenyl)amino)carbonyl)amino)methyl)phenyl)-7-(3-hydroxypropoxy)-1,2-benzisoxazole-4-carboxamide, 3-amino-N-(3-(((anilinocarbonyl)amino)methyl)phenyl)-7-(3-hydroxypropoxy)-1,2-benzisoxazole-4-carboxamide, 3-amino-N-(3-(1-((((3-fluorophenyl)amino)carbonyl)amino)ethyl)phenyl)-1,2-benzisoxazole-4-carboxamide, 3-amino-N-(4-((anilinocarbonyl)amino)benzyl)-1,2-benzisoxazole-4-carboxamide, 3-amino-N-(3-(((anilinocarbonyl)amino)methyl)phenyl)-1H-indazole-4-carboxamide, 3-amino-N-(3-(((((4-chlorophenyl)amino)carbonyl)amino)methyl)phenyl)-1H-indazole-4-carboxamide, 3-amino-N-(3-(((((4-chloro-2-fluorophenyl)amino)carbonyl)amino)methyl)phenyl)-1H-indazole-4-carboxamide, 3-amino-N-(3-(((((3-fluoro-4-methylphenyl)amino)carbonyl)amino)methyl)phenyl)-1H-indazole-4-carboxamide, 3-amino-N-(3-(((((2-fluoro-5-methylphenyl)amino)carbonyl)amino)methyl)phenyl)-1H-indazole-4-carboxamide, 3-amino-N-(3-(((((2-fluoro-5-(trifluoromethyl)phenyl)amino)carbonyl)amino)methyl)phenyl)-1H-indazole-4-carboxamide, 3-amino-N-(3-(((((3,5-difluorophenyl)amino)carbonyl)amino)methyl)phenyl)-1H-indazole-4-carboxamide, 3-amino-N-(3-(((((3,4-difluorophenyl)amino)carbonyl)amino)methyl)phenyl)-1H-indazole-4-carboxamide, 3-amino-N-(3-(((((3-fluoro-4-methylphenyl)amino)carbonyl)amino)methyl)phenyl)-1,2-benzisoxazole-4-carboxamide, 3-amino-N-(3-(((((4-chlorophenyl)amino)carbonyl)amino)methyl)phenyl)-1,2-benzisoxazole-4-carboxamide, 3-amino-N-(3-(((((3-bromophenyl)amino)carbonyl)amino)methyl)phenyl)-1,2-benzisoxazole-4-carboxamide, 3-amino-N-(3-(((((3-fluorophenyl)amino)carbonyl)amino)methyl)phenyl)-7-(2-morpholin-4-ylethoxy)-1,2-benzisoxazole-4-carboxamide;

3-amino-N-(3-(((anilinocarbonyl)amino)methyl)phenyl)-7-(2-morpholin-4-ylethoxy)-1,2-benzisoxazole-4-carboxamide;

3-amino-7-(2-morpholin-4-ylethoxy)-N-(3-(((((4-(trifluoromethyl)phenyl)amino)carbonyl)amino)methyl)phenyl)-1,2-benzisoxazole-4-carboxamide;

3-amino-N-(3-(((((3-fluorophenyl)amino)carbonyl)amino)methyl)phenyl)-7-methoxy-1,2-benzisoxazole-4-carboxamide;

3-amino-N-(3-(((anilinocarbonyl)amino)methyl)phenyl)-7-methoxy-1,2-benzisoxazole-4-carboxamide;

3-amino-7-methoxy-N-(3-(((((4-(trifluoromethyl)phenyl)amino)carbonyl)amino)methyl)phenyl)-1,2-benzisoxazole-4-carboxamide;

3-amino-N-(3-(((((4-chloro-2-fluorophenyl)amino)carbonyl)amino)methyl)phenyl)-1,2-benzisoxazole-4-carboxamide;

3-amino-N-(3-(((((4-chloro-2-fluorophenyl)amino)carbonyl)amino)methyl)phenyl)-7-methoxy-1,2-benzisoxazole-4-carboxamide;

3-amino-7-(3-hydroxypropoxy)-N-(3-(((((4-(trifluoromethyl)phenyl)amino)carbonyl)amino)methyl)phenyl)-1,2-benzisoxazole-4-carboxamide;

3-amino-N-(3-(((((3,4-difluorophenyl)amino)carbonyl)amino)methyl)phenyl)-7-methoxy-1,2-benzisoxazole-4-carboxamide;

3-amino-N-(3-((((pyridin-3-ylamino)carbonyl)amino)methyl)phenyl)-1,2-benzisoxazole-4-carboxamide;

3-amino-7-methoxy-N-(3-((((pyridin-3-ylamino)carbonyl)amino)methyl)phenyl)-1,2-benzisoxazole-4-carboxamide;

3-amino-N-(3-(((((4-chlorophenyl)amino)carbonyl)amino)methyl)phenyl)-7-(2-morpholin-4-ylethoxy)-1,2-benzisoxazole-4-carboxamide;

3-amino-N-(4-((anilinocarbonyl)amino)phenyl)-7-(2-morpholin-4-ylethoxy)-1,2-benzisoxazole-4-carboxamide;

3-amino-N-(3-(((((4-chlorophenyl)amino)carbonyl)amino)methyl)phenyl)-7-(2-(4-methylpiperazin-1-yl)ethoxy)-1,2-benzisoxazole-4-carboxamide;

3-amino-7-(2-(4-methylpiperazin-1-yl)ethoxy)-N-(3-(((((4-(trifluoromethyl)phenyl)amino)carbonyl)amino)methyl)phenyl)-1,2-benzisoxazole-4-carboxamide;

3-amino-N-(3-(((((4-methylphenyl)amino)carbonyl) amino)methyl)phenyl)-7-(2-(4-methylpiperazin-1-yl) ethoxy)-1,2-benzisoxazole-4-carboxamide;

3-amino-N-(3-(((((2,4-difluorophenyl)amino)carbonyl) amino)methyl)phenyl)-7-methoxy-1,2-benzisoxazole-4-carboxamide;

3-amino-N-(3-(((((4-chlorophenyl)amino)carbonyl) amino)methyl)phenyl)-7-methoxy-1,2-benzisoxazole-4-carboxamide;

3-amino-7-methoxy-N-(3-(((((4-methylphenyl)amino) carbonyl)amino)methyl)phenyl)-1,2-benzisoxazole-4-carboxamide;

3-amino-N-(3-(((((2,5-difluorophenyl)amino)carbonyl) amino)methyl)phenyl)-7-methoxy-1,2-benzisoxazole-4-carboxamide;

3-amino-N-(3-(((((4-(difluoromethoxy)phenyl)amino) carbonyl)amino)methyl)phenyl)-7-methoxy-1,2-benzisoxazole-4-carboxamide;

3-amino-N-(4-((((3-fluorophenyl)amino)carbonyl) amino)-3-methylphenyl)-1,2-benzisoxazole-4-carboxamide;

3-amino-N-(4-((((3-fluorophenyl)amino)carbonyl) amino)-3-methylphenyl)-7-methoxy-1,2-benzisoxazole-4-carboxamide;

3-amino-N-(4-((((2-fluorophenyl)amino)carbonyl) amino)-3-methylphenyl)-1,2-benzisoxazole-4-carboxamide;

3-amino-N-(4-((((2-fluorophenyl)amino)carbonyl) amino)-3-methylphenyl)-7-methoxy-1,2-benzisoxazole-4-carboxamide;

3-amino-N-(3-methyl-4-((((4-(trifluoromethyl)phenyl) amino)carbonyl)amino)phenyl)-1,2-benzisoxazole-4-carboxamide;

3-amino-7-methoxy-N-(3-methyl-4-((((4-(trifluoromethyl)phenyl)amino)carbonyl)amino)phenyl)-1,2-benzisoxazole-4-carboxamide;

3-amino-N-(3-(((((4-chlorophenyl)amino)carbonyl) amino)methyl)-4-fluorophenyl)-1,2-benzisoxazole-4-carboxamide;

3-amino-N-(4-fluoro-3-(((((4-methylphenyl)amino)carbonyl)amino)methyl)phenyl)-1,2-benzisoxazole-4-carboxamide;

3-amino-N-(3-(((((4-(difluoromethoxy)phenyl)amino) carbonyl)amino)methyl)-4-fluorophenyl)-1,2-benzisoxazole-4-carboxamide;

3-amino-N-(4-fluoro-3-(((((2-fluoro-5-methylphenyl) amino)carbonyl)amino)methyl)phenyl)-1,2-benzisoxazole-4-carboxamide;

3-amino-N-(3-(((((4-chloro-2-fluorophenyl)amino)carbonyl)amino)methyl)-4-fluorophenyl)-1,2-benzisoxazole-4-carboxamide;

3-amino-N-(4-fluoro-3-(((((4-(trifluoromethyl)phenyl) amino)carbonyl)amino)methyl)phenyl)-1,2-benzisoxazole-4-carboxamide;

3-amino-N-(3-(((anilinocarbonyl)amino)methyl)-4-fluorophenyl)-1,2-benzisoxazole-4-carboxamide;

3-amino-N-(4-fluoro-3-(((((4-fluorophenyl)amino)carbonyl)amino)methyl)phenyl)-1,2-benzisoxazole-4-carboxamide;

3-amino-N-(4-fluoro-3-(((((3-(trifluoromethyl)phenyl) amino)carbonyl)amino)methyl)phenyl)-1,2-benzisoxazole-4-carboxamide;

3-amino-N-(3-(((((2,5-difluorophenyl)amino)carbonyl) amino)methyl)-4-fluorophenyl)-1,2-benzisoxazole-4-carboxamide;

3-amino-N-(3-(((4-fluorobenzoyl)amino)methyl)phenyl)-1,2-benzisoxazole-4-carboxamide;

3-amino-N-(3-(((3-fluorobenzoyl)amino)methyl)phenyl)-1,2-benzisoxazole-4-carboxamide;

3-amino-N-(3-(((anilinocarbonyl)amino)methyl)-4-methylphenyl)-1,2-benzisoxazole-4-carboxamide;

3-amino-N-(3-(aminomethyl)phenyl)-1,2-benzisoxazole-4-carboxamide;

3-amino-N-(3-(((((3-fluorophenyl)amino)carbonyl) amino)methyl)phenyl)-1-methyl-1H-indazole-4-carboxamide;

3-amino-N-(3-(((((4-chloro-2-fluorophenyl)amino)carbonyl)amino)methyl)phenyl)-1-methyl-1H-indazole-4-carboxamide;

3-amino-N-(3-(((((4-chlorophenyl)amino)carbonyl) amino)methyl)phenyl)-1-methyl-1H-indazole-4-carboxamide;

3-amino-N-(3-(((((3-fluoro-4-methylphenyl)amino)carbonyl)amino)methyl)phenyl)-1-methyl-1H-indazole-4-carboxamide;

3-amino-N-(3-(((((3-chloro-4-fluorophenyl)amino)carbonyl)amino)methyl)phenyl)-1-methyl-1H-indazole-4-carboxamide;

3-amino-1-methyl-N-(3-(((((3-(trifluoromethyl)phenyl) amino)carbonyl)amino)methyl)phenyl)-1H-indazole-4-carboxamide;

3-amino-1-methyl-N-(3-(((((4-(trifluoromethyl)phenyl) amino)carbonyl)amino)methyl)phenyl)-1H-indazole-4-carboxamide;

3-amino-N-(3-(((((4-fluorophenyl)amino)carbonyl) amino)methyl)phenyl)-1-methyl-1H-indazole-4-carboxamide;

3-amino-N-(3-(((((2-chlorophenyl)amino)carbonyl) amino)methyl)phenyl)-1-methyl-1H-indazole-4-carboxamide;

3-amino-N-(3-(((((4-methylphenyl)amino)carbonyl) amino)methyl)phenyl)-1H-indazole-4-carboxamide;

3-amino-N-(3-(((((2-fluorophenyl)amino)carbonyl) amino)methyl)phenyl)-1H-indazole-4-carboxamide;

3-amino-N-(3-(((((4-isopropylphenyl)amino)carbonyl) amino)methyl)phenyl)-1H-indazole-4-carboxamide;

and therapeutically acceptable salts, prodrugs, esters, amides, salts of prodrugs, salts of esters, and salts of amides thereof.

DETAILED DESCRIPTION OF THE INVENTION

Variable moieties of compounds herein are represented by identifiers (capital letters with numerical and/or alphabetical superscripts) and may be specifically embodied.

It is meant to be understood that proper valences are maintained for all moieties and combinations thereof, that monovalent moieties having more than one atom are attached through their left ends.

It is also meant to be understood that a specific embodiment of a variable moiety may be the same or different as another specific embodiment having the same identifier.

The term "cyclic moiety," as used herein, means benzene, cycloalkane, cycloalkyl, cycloalkene, cycloalkenyl, heteroarene, heteroaryl, heterocycloalkane, heterocycloalkyl, heterocycloalkene, heterocycloalkenyl and phenyl.

The term "cycloalkane," as used herein, means $C_3$-cycloalkane, $C_4$-cycloalkane, $C_5$-cycloalkane and $C_6$-cycloalkane.

The term "cycloalkyl," as used herein, means $C_3$-cycloalkyl, $C_4$-cycloalkyl, $C_5$-cycloalkyl and $C_6$-cycloalkyl.

The term "cycloalkene," as used herein, means $C_4$-cycloalkene, $C_5$-cycloalkene and $C_6$-cycloalkene.

The term "cycloalkenyl," as used herein, means $C_4$-cycloalkenyl, $C_5$-cycloalkenyl and $C_6$-cycloalkenyl.

The term "heteroarene," as used herein, means furan, imidazole, isothiazole, isoxazole, 1,2,3-oxadiazole, 1,2,5-oxadiazole, oxazole, pyrazine, pyrazole, pyridazine, pyridine, pyrimidine, pyrrole, thiazole, thiophene, triazine and 1,2,3-triazole.

The term "heteroaryl," as used herein, means furanyl, imidazolyl, isothiazolyl, isoxazolyl, 1,2,3-oxadiazoyl, 1,2,5-oxadiazolyl, oxazolyl, pyrazinyl, pyrazolyl, pyridazinyl, pyridinyl, pyrimidinyl, pyrrolyl, tetrazolyl, thiazolyl, thiophenyl, triazinyl and 1,2,3-triazolyl.

The term "heterocycloalkane," as used herein, means cycloalkane having one or two or three $CH_2$ moieties replaced with independently selected O, S, S(O), $SO_2$ or NH and one or two CH moieties unreplaced or replaced with N and also means cycloalkane having one or two or three $CH_2$ moieties unreplaced or replaced with independently selected O, S, S(O), $SO_2$ or NH and one or two CH moieties replaced with N.

The term "heterocycloalkyl," as used herein, means cycloalkyl having one or two or three $CH_2$ moieties replaced with independently selected O, S, S(O), $SO_2$ or NH and one or two CH moieties unreplaced or replaced with N and also means cycloalkyl having one or two or three $CH_2$ moieties unreplaced or replaced with independently selected O, S, S(O), $SO_2$ or NH and one or two CH moieties replaced with N.

The term "heterocycloalkene," as used herein, means cycloalkene having one or two or three $CH_2$ moieties replaced with independently selected O, S, S(O), $SO_2$ or NH and one or two CH moieties unreplaced or replaced with N and also means cycloalkene having one or two or three $CH_2$ moieties unreplaced or replaced with independently selected O, S, S(O), $SO_2$ or NH and one or two CH moieties replaced with N.

The term "heterocycloalkenyl," as used herein, means cycloalkenyl having one or two or three $CH_2$ moieties replaced with independently selected O, S, S(O), $SO_2$ or NH and one or two CH moieties unreplaced or replaced with N and also means cycloalkenyl having one or two or three $CH_2$ moieties unreplaced or replaced with independently selected O, S, S(O), $SO_2$ or NH and one or two CH moieties replaced with N.

The term "alkenyl," as used herein, means $C_2$-alkenyl, $C_3$-alkenyl, $C_4$-alkenyl, $C_5$-alkenyl and $C_6$-alkenyl.

The term "alkyl," as used herein, means $C_1$-alkyl, $C_2$-alkyl, $C_3$-alkyl, $C_4$-alkyl, $C_5$-alkyl and $C_6$-alkyl.

The term "alkynyl," as used herein, means $C_2$-alkynyl, $C_3$-alkynyl, $C_4$-alkynyl, $C_5$-alkynyl and $C_6$-alkynyl.

Compounds of this invention may contain asymmetrically substituted carbon atoms in the R or S configuration, wherein the terms "R" and "S" are as defined in Pure Appl. Chem. (1976) 45, 13-10. Compounds having asymmetrically substituted carbon atoms with equal amounts of R and S configurations are racemic at those atoms. Atoms having excess of one configuration over the other are assigned the configuration in excess, preferably an excess of about 85%-90%, more preferably an excess of about 95%-99%, and still more preferably an excess greater than about 99%. Accordingly, this invention is meant to embrace racemic mixtures and relative and absolute diastereoisomers of the compounds thereof.

Compounds of this invention may also contain carbon-carbon double bonds or carbon-nitrogen double bonds in the Z or E configuration, in which the term "Z" represents the larger two substituents on the same side of a carbon-carbon or carbon-nitrogen double bond and the term "E" represents the larger two substituents on opposite sides of a carbon-carbon or carbon-nitrogen double bond. The compounds of this invention may also exist as a mixture of "Z" and "E" isomers.

Compounds of this invention may also exist as tautomers or equilibrium mixtures thereof wherein a proton of a compound shifts from one atom to another. Examples of tautomers include, but are not limited to, keto-enol, phenol-keto, oxime-nitroso, nitro-aci, imine-enamine and the like.

Compounds of this invention containing NH, C(O)OH, OH or SH moieties may have attached thereto prodrug-forming moieties. The prodrug-forming moieties are removed by metabolic processes and release the compounds having the freed NH, C(O)OH, OH or SH in vivo. Prodrugs are useful for adjusting such pharmacokinetic properties of the compounds as solubility and/or hydrophobicity, absorption in the gastrointestinal tract, bioavailability, tissue penetration, and rate of clearance.

Metabolites of compounds having Formula I produced by in vitro or in vivo metabolic processes, may also have utility for treating diseases associated with overexpression or unregulation of protein kinases.

Certain precursor compounds which may be metabolized in vitro or in vivo to form compounds having Formula I may also have utility for treating diseases associated with overexpression or unregulation of protein kinases.

Compounds having Formula I may exist as acid addition salts, basic addition salts or zwitterions. Salts of compounds having Formula I are prepared during their isolation or following their purification. Acid addition salts are those derived from the reaction of a compound having Formula I with acid. Accordingly, salts including the acetate, adipate, alginate, bicarbonate, citrate, aspartate, benzoate, benzenesulfonate (besylate), bisulfate, butyrate, camphorate, camphorsulfonate, digluconate, formate, fumarate, glycerophosphate, glutamate, hemisulfate, heptanoate, hexanoate, hydrochloride, hydrobromide, hydroiodide, lactobionate, lactate, maleate, mesitylenesulfonate, methanesulfonate, naphthylenesulfonate, nicotinate, oxalate, pamoate, pectinate, persulfate, phosphate, picrate, propionate, succinate, tartrate, thiocyanate, trichloroacetic, trifluoroacetic, para-toluenesulfonate and undecanoate salts of the compounds having Formula I are meant to be embraced by this invention. Basic addition salts of compounds are those derived from the reaction of the compounds having Formula I with the bicarbonate, carbonate, hydroxide or phosphate of cations such as lithium, sodium, potassium, calcium and magnesium.

Compounds having Formula I may be administered, for example, bucally, ophthalmically, orally, osmotically, parenterally (intramuscularly, intraperintoneally intrasternally, intravenously, subcutaneously), rectally, topically, transdermally, vaginally and intraarterially as well as by intraarticular injection, infusion, and placement in the body, such as, for example, the vasculature.

Therapeutically effective amounts of a compound having Formula I depend on recipient of treatment, disease treated and severity thereof, composition comprising it, time of administration, route of administration, duration of treatment, potency, rate of clearance and whether or not another drug is co-administered. The amount of a compound having Formula I used to make a composition to be administered daily to a patient in a single dose or in divided doses is from about 0.03 to about 200 mg/kg body weight. Single dose compositions contain these amounts or a combination of submultiples thereof.

Compounds having Formula I may be administered with or without an excipient. Excipients include, but are not limited to, encapsulators and additives such as absorption accelerators, antioxidants, binders, buffers, coating agents, coloring agents, diluents, disintegrating agents, emulsifiers, extenders, fillers, flavoring agents, humectants, lubricants, perfumes, preservatives, propellants, releasing agents, sterilizing agents, sweeteners, solubilizers, wetting agents, mixtures thereof and the like.

Excipients for preparation of compositions comprising a compound having Formula I to be administered orally include, but are not limited to, agar, alginic acid, aluminum hydroxide, benzyl alcohol, benzyl benzoate, 1,3-butylene glycol, carbomers, castor oil, cellulose, cellulose acetate, cocoa butter, corn starch, corn oil, cottonseed oil, cross-povidone, diglycerides, ethanol, ethyl cellulose, ethyl laureate, ethyl oleate, fatty acid esters, gelatin, germ oil, glucose, glycerol, groundnut oil, hydroxypropylmethyl celluose, isopropanol, isotonic saline, lactose, magnesium hydroxide, magnesium stearate, malt, mannitol, monoglycerides, olive oil, peanut oil, potassium phosphate salts, potato starch, povidone, propylene glycol, Ringer's solution, safflower oil, sesame oil, sodium carboxymethyl cellulose, sodium phosphate salts, sodium lauryl sulfate, sodium sorbitol, soybean oil, stearic acids, stearyl fumarate, sucrose, surfactants, talc, tragacanth, tetrahydrofurfuryl alcohol, triglycerides, water, mixtures thereof and the like. Excipients for preparation of compositions comprising a compound having Formula I to be administered ophthalmically or orally include, but are not limited to, 1,3-butylene glycol, castor oil, corn oil, cottonseed oil, ethanol, fatty acid esters of sorbitan, germ oil, groundnut oil, glycerol, isopropanol, olive oil, polyethylene glycols, propylene glycol, sesame oil, water, mixtures thereof and the like. Excipients for preparation of compositions comprising a compound having Formula I to be administered osmotically include, but are not limited to, chlorofluorohydrocarbons, ethanol, water, mixtures thereof and the like. Excipients for preparation of compositions comprising a compound having Formula I to be administered parenterally include, but are not limited to, 1,3-butanediol, castor oil, corn oil, cottonseed oil, dextrose, germ oil, groundnut oil, liposomes, oleic acid, olive oil, peanut oil, Ringer's solution, safflower oil, sesame oil, soybean oil, U.S.P. or isotonic sodium chloride solution, water, mixtures thereof and the like. Excipients for preparation of compositions comprising a compound having Formula I to be administered rectally or vaginally include, but are not limited to, cocoa butter, polyethylene glycol, wax, mixtures thereof and the like.

Compounds having Formula I are also expected to be useful as chemotherapeutic agents in combination with actinomycins, alkylating agents, anthracyclines, antifolates, antiestrogen agents, anti-metabolites, anti-androgens, antimicrotubule agents, aromatase inhibitors, bleomycins, $Ca^{2+}$ adenosine triphosphate (ATP)ase inhibitors, cytosine analogs, deltoids/retinoids, dihydrofolate reductase inhibitors, deoxyribonucleic acid (DNA) topoisomerase inhibitors, dopaminergic neurotoxins, glucocorticoids, histone deacetylase inhibitors, hormonal therapies, immunotherapeutic agents, inosine monophosphate (IMP) dehydrogenase inhibitors, isoprenylation inhibitors, luteinizing hormone-releasing hormone agonists, mammalian target of rapamycin (mtor) inhibitors, multi-drug resistance (MDR) inhibitors, mitomycins, photodyamic therapies, proteasome inhibitors, platinum containing compounds, radiation, receptor tyrosine kinase inhibitors, ribonucleotide reductase inhibitors, thrombospondin mimetics, uracil analogs, vinca alkaloids, and vitamin D3 analogs such as, but not limited to, γ-radiation or an additional chemotherapeutic agent or additional chemotherapeutic agents such as N-Ac-Sar-Gly-Val-D-alloIle-Thr-Nva-Ile-Arg-Pro-NHCH$_2$CH$_3$ or a salt thereof, actinomycin D, AG13736, 17-allylamino-17-demethoxygeldanamycin, 9-aminocamptothecin, N-(4-(3-amino-1H-indazol-4-yl)phenyl)-N'-(2-fluoro-5-methylphenyl)urea or a salt thereof, N-(4-(4-aminothieno(2,3-d)pyrimidin-5-yl)phenyl)-N'-(2-fluoro-5-(trifluoromethyl)phenyl)urea or a salt thereof, anastozole, AP-23573, asparaginase, azacitidine, bevacizumab, bicalutamide, bleomycin a2, bleomycin b2, bortezamib, busulfan, campathecins, carboplatin, carmustine (BCNU), CB1093, cetuximab, CHOP (C: Cytoxan® (cyclophosphamide); H: Adriamycin® (hydroxydoxorubicin); 0: Vincristine (Oncovin®); P: prednisone), chlorambucil, CHIR258, cisplatin, CNF-101, CNF-1001, CNF-2024, CP547632, crisnatol, cytarabine, cyclophosphamide, cytosine arabinoside, daunorubicin, dacarbazine, dactinomycin, dasatinib, daunorubicin, deferoxamine, demethoxyhypocrellin A, depsipeptide, dexamethasone, 17-dimethylaminoethylamino-17-demethoxygeldanamycin, docetaxel, doxifluridine, doxorubicin, EB1089, epothilone D, epirubicin, 5-ethynyl-1-β-D-ribofuranosylimidazole-4-carboxamide (EICAR), erlotinib, etoposide, everolimus, 5-fluorouracil (5-FU), floxuridine, fludarabine, flutamide, gefitinib, geldanamycin, gemcitabine, goserelin, N-(2-(4-hydroxyanilino)-3-pyridinyl)-4-methoxybenzenesulfonamide or a salt thereof, hydroxyurea, idarubicin, ifosfamide, imatinab, interferon-α, interferon-γ, IPI-504, irinotecan, KH 1060, lapatanib, LAQ824, leuprolide acetate, letrozole, lomustine (CCNU), lovastatin, megestrol, melphalan, mercaptopurine, methotrexate, 1-methyl-4-phyenylpyridinium, MG 132, mitomycin, mitoxantrone, MLN-518, MS-275, mycophenolic acid, mitomycin C, nitrosoureas, oxaliplatin, paclitaxel, PD98059, peplomycin, photosensitizer Pc4, phtalocyanine, pirarubicin, plicamycin, prednisone, procarbizine, PTK787, PU24FC1, PU3, radicicol, raloxifene, rapamycin, ratitrexed, retinoids such as pheuretinide, ribavirin, rituximab (Rituxin®), sorafenib, staurosporine, steroids such as dexamethasone and prednisone, suberoylanilide hydroxamic acid, sunitinib, tamoxifen, taxol, temozolamide, temsirolimus, teniposide, thapsigargin, thioguanine, thrombospondin-1, tiazofurin, topotecan, trapoxin, trastuzumab, treosulfan, trichostatin A, trimetrexate, trofosfamide, tumor necrosis factor, valproic acid, VER49009, verapamil, vertoporfin, vinblastine, vincristine, vindesine, vinorelbine vitamin D3, VX-680, zactima, ZK-EPO, zorubicin or combinations thereof.

To determine activity of representative compounds of the invention, Active Aurora B enzyme (recombinant residues 1-344) and INCENP (recombinant GST fusion protein from Upstate) were incubated in wells of a 384 well plate with biotinylted histone H3 peptide residues 1-21 (Upstate), 1 mM ATP, and various concentrations of inhibitors in a Hepes buffer, pH 7.4 containing MgCl$_2$, sodium othrovanadate, and Triton X-100. After 1 hour, the reaction was stopped with EDTA and anti-phospho-histone H3 Europium Cryptate (Cis-Bio) and SA-APC (Phycolink, Prozyme) were added to detect the phosphopeptide. The amount of phosphorylation was determined by the time-resolved fluorescence ratio of signals at 665 nm and 615 nm. The IC$_{50}$'s were calculated by an exponential fit of the inhibition values with the inhibitor concentrations using Assay Explorer software.

The following table of data (nM) demonstrates the utility of compounds having Formula I as inhibitors of Aurora-kinase B.

| | | | | |
|---|---|---|---|---|
| 2.2 | 2.4 | 2.6 | 2.9 | 3.0 |
| 3.6 | 3.8 | 4.6 | 6.4 | 6.5 |
| 6.7 | 6.8 | 7.4 | 7.7 | 8.1 |
| 8.8 | 9.0 | 9.0 | 10.4 | 10.6 |
| 10.9 | 11.3 | 12.1 | 12.2 | 12.2 |
| 13.4 | 14.6 | 15.4 | 15.7 | 15.9 |

-continued

| | | | | |
|---|---|---|---|---|
| 16.2 | 17.5 | 17.9 | 18.4 | 18.5 |
| 19.7 | 21.0 | 21.2 | 21.5 | 21.7 |
| 24.0 | 24.7 | 27.6 | 32.5 | 33.6 |
| 34.0 | 38.3 | 38.4 | 39.0 | 40.7 |
| 40.9 | 45.0 | 47.1 | 50.3 | 51.1 |
| 53.4 | 55.1 | 58.6 | 60.2 | 61.6 |
| 65.3 | 66.0 | 70.4 | 72.6 | 72.7 |
| 76.8 | 80.0 | 81.1 | 82.4 | 85.9 |
| 86.6 | 90.7 | 95.4 | 105.0 | 111.0 |
| 127.0 | 129.0 | 140.0 | 143.0 | 164.0 |
| 173.0 | 188.0 | 194.0 | 195.0 | 197.0 |
| 199.0 | 205.0 | 206.0 | 211.0 | 223.0 |
| 237.0 | 254.0 | 288.0 | 331.0 | 353.0 |
| 395.0 | 397.0 | 447.0 | 450.0 | 471.0 |
| 481.0 | 504.0 | 525.0 | 573.0 | 636.0 |
| 640.0 | 693.0 | 817.0 | 843.0 | 858.0 |
| 887.0 | 915.0 | 939.0 | 1080.0 | 1250.0 |
| 1740.0 | 1830.0 | 2500.0 | 2570.0 | 2590.0 |
| 2700.0 | 2800.0 | 3440.0 | 4890.0 | 5560.0 |
| 5650.0 | 7670.0 | 9800.0 | 10900.0 | 12100.0 |

It is expected that, because compounds having Formula I inhibit the activity of Aurora-kinase B, they could also have utility as inhibitors of protein kinases having close structural homology thereto, such as, for example, Aurora-kinase A and Aurora-kinase C.

The structural homology between Protein Kinases A, B and C is reported in Nature Reviews/Cancer, Vol. 4 December, 2004.

Accordingly, compounds having Formula I are expected to have utility in treatment of diseases during which protein kinases such as any or all Aurora-kinase family members are expressed.

Diseases involving overexpression or unregulation of Aurora-kinase family members include, but are not limited to, acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute t-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic (granulocytic) leukemia, chronic myelogeneous leukemia, colon cancer, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, heavy chain disease, hemangioblastoma, hepatoma, hepatocellular cancer, hormone insensitive prostate cancer, leiomyosarcoma, liposarcoma, lung cancer, lymphangioendotheliosarcoma, lymphangiosarcoma, lymphoblastic leukemia, lymphoma (Hodgkin's and non-Hodgkin's), malignancies and hyperproliferative disorders of the bladder, breast, colon, lung, ovaries, pancreas, prostate, skin and uterus, lymphoid malignancies of T-cell or B-cell origin, leukemia, lymphoma, medullary carcinoma, medulloblastoma, melanoma, meningioma, mesothelioma, multiple myeloma, myelogenous leukemia, myeloma, myxosarcoma, neuroblastoma, non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenström's macroglobulinemia, testicular tumors, uterine cancer and Wilms' tumor.

It is also expected that compounds having Formula I would inhibit the growth of cells derived from a cancer or neoplasm such as breast cancer (including estrogen-receptor positive breast cancer), colorectal cancer, endometrial cancer, lung cancer (including small cell lung cancer), lymphoma (including follicular or Diffuse Large B-cell), lymphoma (including non-Hodgkin's lymphoma), neuroblastoma, ovarian cancer, prostate cancer (including hormone-insensitive prostate cancer) and testicular cancer (including germ cell testicular cancer).

It is also expected that compounds having Formula I would inhibit the growth of cells derived from a pediatric cancer or neoplasm such as embryonal rhabdomyosarcoma, pediatric acute lymphoblastic leukemia, pediatric acute myelogenous leukemia, pediatric alveolar rhabdomyosarcoma, pediatric anaplastic ependymoma, pediatric anaplastic large cell lymphoma, pediatric anaplastic medulloblastoma, pediatric atypical teratoid/rhabdoid tumor of the central nervous system, pediatric biphenotypic acute leukemia, pediatric Burkitts lymphoma, pediatric cancers of Ewing's family of tumors such as primitive neuroectodermal rumors, pediatric diffuse anaplastic Wilm's tumor, pediatric favorable histology Wilm's tumor, pediatric glioblastoma, pediatric medulloblastoma, pediatric neuroblastoma, pediatric neuroblastoma-derived myelocytomatosis, pediatric pre-B-cell cancers (such as leukemia), pediatric psteosarcoma, pediatric rhabdoid kidney tumor, pediatric rhabdomyosarcoma, and pediatric T-cell cancers such as lymphoma and skin cancer.

Involvement of Aurora Kinase in pancreatic carcinoma cells is reported in Zhu, J., et al., AURKA amplification, chromosome instability, and centrosome abnormality in human pancreatic carcinoma cells. Cancer Genet. Cytogenet., 2005. 159(1): p. 10-17; and Li D, ZhuJ, Firozi P F, et al. Overexpression of oncogenic STK15/BTAK/aurora A kinase in human pancreatic cancer. Clin Cancer Res 2003; 9:991-7.

Involvement of Aurora Kinase in non-small cell lung carcinoma is reported in Smith, S. L., et al., Overexpression of Aurora B kinase (AURKB) in primary non-small cell lung carcinoma is frequent, generally driven from one allele, and correlates with the level of genetic instability. Br. J. Cancer, 2005. 93(6): p. 719-729.

Involvement of Aurora Kinase in prostate cancer is reported in Chieffi, P., et al., Aurora B expression directly correlates with prostate cancer malignancy. Prostate, 2006. 66(3): p. 326-33; and Chieffi P, Cozzolino L, KisslingerA, et al. Aurora B expression directly correlates with prostate cancer malignancy and influence prostate cell proliferation. Prostate 2006; 66:326-33.

Involvement of Aurora Kinase in head and neck squamous cell carcinoma is reported in Reiter, R., et al., Aurora kinase a messenger RNA overexpression is correlated with tumor progression and shortened survival in head and neck squamous cell carcinoma. Clin Cancer Res, 2006. 12(17): p. 5136-41.

Involvement of Aurora Kinase in acute myeloid leukemia is reported in Walsby E, Walsh V, Pepper C, Burnett A, Mills K. Haematologica. 2008 May; 93(5):662-9.

Involvement of Aurora Kinase in breast cancer is reported in Tanaka T, Kimura M, Matsunaga K, Fukada D, Mori H, Okano Y. Centrosomal kinase AIK1 is overexpressed in invasive ductal carcinoma of the breast. Cancer Res 1999; 59:2041-4;

Miyoshi Y, Iwao K, Egawa C, Noguchi S. Association of centrosomal kinase STK15/BTAK mRNA expression with chromosomal instability in human breast cancers. Int J Cancer 2001; 92:370-3;

Hoque A, Carter J, Xia W, et al. Loss of aurora A/STK15/BTAK overexpression correlates with transition of in situ to invasive ductal carcinoma of the breast. Cancer Epidemiol Biomarkers Prev 2003; 12:1518-22;

Royce M E, Xia W, Sahin A A, et al. STK15/aurora-A expression in primary breast tumors is correlated with nuclear grade but not with prognosis. Cancer 2004; 100:12-9;

Bodvarsdottir S K, Hilmarsdottir H, Birgisdottir V, Steinarsdottir M, Jonasson J G, Eyfjord J E. Aurora-A amplification associated with BRCA2 mutation in breast tumours. Cancer Lett 2007; 248:96-102;

Sen S, Zhou H, White R A. A putative serine/threonine kinase encoding gene BTAK on chromosome 20q13 is amplified and overexpressed in human breast cancer cell lines. Oncogene 1997; 14:2195-200;

Lo Y L, Yu J C, Chen S T, et al. Breast cancer risk associated with genotypic polymorphism of the mitosis regulating gene aurora-A/STK15/BTAK. Int J Cancer 2005; 115:276-83;

Vidarsdottir L, Bodvarsdottir S K, Hilmarsdottir H, Tryggvadottir L, Eyfjord J E. Breast cancer risk associated with AURKA 91T A polymorphism in relation to BRCA mutations. Cancer Lett 2007; 250:206-12;

Cox D G, Hankinson S E, Hunter D J. Polymorphisms of the AURKA (STK15/aurora kinase) gene and breast cancer risk (United States). Cancer Causes Control 2006; 17:81-3; and Tchatchou S, Wirtenberger M, Hemminki K, et al. Aurora kinases A and B and familial breast cancer risk. Cancer Lett 2007; 247:266-72.

Involvement of Aurora Kinase in lung cancer is reported in Smith S L, Bowers N L, Betticher D C, et al. Overexpression of aurora B kinase (AURKB) in primary nonsmall cell lung carcinoma is frequent, generally driven from one allele, and correlates with the level of genetic instability. Br J Cancer 2005; 93:719-29;

Xu H T, Ma L, Qi F J, et al. Expression of serine threonine kinase15 is associated with poor differentiation in lung squamous cell carcinoma and adenocarcinoma. Pathol Int 2006; 56:375-80;

Vischioni B, Oudejans J J, Vos W, Rodriguez J A, Giaccone G. Frequent overexpression of aurora B kinase, a novel drug target, in non-small cell lung carcinoma patients. Mol Cancer Ther 2006; 5:2905-13; and Gu J, Gong Y, Huang M, Lu C, Spitz M R, Wu X. Polymorphisms of STK15 (aurora-A) gene and lung cancer risk in Caucasians. Carcinogenesis 2007; 28:350-5.

Involvement of Aurora Kinase in bladder cancer is reported in Comperat E, Camparo P, Haus R, et al. Aurora-A/STK-15 is a predictive factor for recurrent behaviour in non-invasive bladder carcinoma: a study of 128 cases of non-invasive neoplasms. Virchows Arch 2007; 450:419-24;

Fraizer G C, Diaz M F, Lee I L, Grossman H B, Sen S. Aurora-A/STK15/BTAK enhances chromosomal instability in bladder cancer cells. Int J Oncol 2004; 25:1631-9; and Sen S, Zhou H, Zhang R D, et al. Amplification/overexpression of a mitotic kinase gene in human bladder cancer. J Natl Cancer Inst 2002; 94:1320-9.

Involvement of Aurora Kinase in esophageal cancer is reported in Tong T, Zhong Y, Kong J, et al. Overexpression of aurora-A contributes to malignant development of human esophageal squamous cell carcinoma. Clin Cancer Res 2004; 10:7304-10;

Yang S B, Zhou X B, Zhu H X, et al. Amplification and overexpression of aurora-A in esophageal squamous cell carcinoma. Oncol Rep 2007; 17:1083-8; and Kimura M T, Mori T, Conroy J, et al. Two functional coding single nucleotide polymorphisms in STK15 (aurora-A) coordinately increase esophageal cancer risk. Cancer Res 2005; 65:3548-54.

Involvement of Aurora Kinase in brain cancer is reported in Araki K, Nozaki K, Ueba T, Tatsuka M, Hashimoto N. High expression of aurora-B/aurora and Ipll-like midbody-associated protein (AIM-1) in astrocytomas. J Neurooncol 2004; 67:53-64;

Zeng W F, Navaratne K, Prayson R A, Weil R J. Aurora B expression correlates with aggressive behaviour in glioblastoma multiforme. J Clin Pathol 2007; 60:218-21;

Reichardt W, Jung V, Brunner C, et al. The putative serine/threonine kinase gene STK15 on chromosome 20q13.2 is amplified in human gliomas. Oncol Rep 2003; 10:1275-9;

Klein A, Reichardt W, Jung V, Zang K D, Meese E, Urbschat S. Overexpression and amplification of STK15 in human gliomas. Int J Oncol 2004; 25:1789-94; and Neben K, Korshunov A, Benner A, et al. Microarray based screening for molecular markers medulloblastoma revealed STK15 as independent predictor for survival. Cancer Res 2004; 64:3103-11.

Involvement of Aurora Kinase in liver cancer is reported in Jeng Y M, Peng S Y, Lin C Y, Hsu H C. Overexpression and amplification of aurora-A in hepatocellular carcinoma. Clin Cancer Res 2004; 10:2065-71.

Involvement of Aurora Kinase in head and neck cancer is reported in Zhao X, Li F C, Li Y H, et al. [Mutation of p53 and overexpression of STK15 in laryngeal squamous-cell carcinoma]. Zhonghua Zhong Liu Za Zhi 2005; 27:134-7;

Li F C, Li Y H, Zhao X, et al. [Deletion of p15 and p16 genes and overexpression of STK15 gene in human laryngeal squamous cell carcinoma]. Zhonghua Yi Xue Za Zhi 2003; 83:316-9;

Reiter R, Gais P, Jutting U, et al. Aurora kinase A messenger RNA overexpression is correlated with tumor progression and shortened survival in head and neck squamous cell carcinoma. Clin Cancer Res 2006; 12:5136-41;

Qi G, Ogawa I, Kudo Y, et al. Aurora-B expression and its correlation with cell proliferation and metastasis in oral cancer. Virchows Arch 2007; 450:297-302; and Tatsuka M, Sato S, Kitajima S, et al. Overexpression of aurora-A potentiates HRAS-mediated oncogenic transformation and is implicated in oral carcinogenesis. Oncogene 2005; 4:1122-7.

Involvement of Aurora Kinase in thyroid cancer is reported in Sorrentino R, Libertini S, Pallante P L, et al. Aurora B overexpression associates with the thyroid carcinoma undifferentiated phenotype and is required for thyroid carcinoma cell proliferation. J Clin Endocrinol Metab 2005; 90:928-35.

Involvement of Aurora Kinase in ovarian cancer is reported in Lassmann S, Shen Y, Jutting U, et al. Predictive value of aurora-A/STK15 expression for late stage epithelial ovarian cancer patients treated by adjuvant chemotherapy. Clin Cancer Res 2007; 13:4083-91; and Landen C N, Jr., Lin Y G, Immaneni A, et al. Overexpression of the centrosomal protein aurora-A kinase is associated with poor prognosis in epithelial ovarian cancer patients. Clin Cancer Res 2007; 13:4098-104.

Involvement of Aurora Kinase in renal cancer is reported in Kurahashi T, Miyake H, Hara I, Fujisawa M. Significance of aurora-A expression in renal cell carcinoma. Urol Oncol 2007; 25:128-33.

Involvement of Aurora Kinase in endometrium cancer is reported in Moreno-Bueno G, Sanchez-Estevez C, Cassia R, et al. Differential gene expression profile in endometrioid and nonendometrioid endometrial carcinoma:STK15 is frequently overexpressed and amplified in nonendometrioid carcinomas. Cancer Res 2003; 63:5697-702.

Involvement of Aurora Kinase in gastric cancer is reported in Ju H, Cho H, Kim Y S, et al. Functional polymorphism 57Val>Ile of aurora kinase A associated with increased risk of gastric cancer progression. Cancer Lett 2006; 242:273-9.

Involvement of Aurora Kinase in colon cancer is reported in Nishida N, Nagasaka T, Kashiwagi K, Boland C R, Goel A. High copy amplification of the Aurora-A gene is associated with chromosomal instability phenotype in human colorectal cancers. Cancer Biol Ther 2007; 6:525-33;

Bischoff J R, Anderson L, Zhu Y, et al. A homologue of Drosophila aurora kinase is oncogenic and amplified in human colorectal cancers. EMBO J. 1998; 17:3052-65;

Chen J, Sen S, Amos C I, et al. Association between aurora-A kinase polymorphisms and age of onset of hereditary nonpolyposis colorectal cancer in a Caucasian population. Mol Carcinog 2007; 46:249-56;

Hienonen T, Salovaara R, Mecklin J P, Jarvinen H, Karhu A, Aaltonen L A. Preferential amplification of AURKA 91A (Ile31) in familial colorectal cancers. Int J Cancer 2006; 118:505-8; and Ewart-Toland A, Briassouli P, de Koning J P, et al. Identification of Stk6/STK15 as a candidate low-penetrance tumor-susceptibility gene in mouse and human. Nat Genet. 2003; 34:403-12.

Involvement of Aurora Kinase in cancer is reported in Lin, Y. S., et al., Gene expression profiles of the aurora family kinases. Gene Expr, 2006. 13(1): p. 15-26; and Ewart-Toland A, Dai Q, Gao Y T, et al. Aurora-A/STK15 T+91A is a general low penetrance cancer susceptibility gene: a meta-analysis of multiple cancer types. Carcinogenesis 2005; 26:1368-73.

Compounds having Formula I are expected to be useful when used with alkylating agents, angiogenesis inhibitors, antibodies, antimetabolites, antimitotics, antiproliferatives, aurora kinase inhibitors, Bcl-2 family protein (for example, Bcl-xL, Bcl-2, Bcl-w, Bfl-1) inhibitors, Bcr-Abl kinase inhibitors, biologic response modifiers, cyclin-dependent kinase inhibitors, cell cycle inhibitors, cyclooxygenase-2 inhibitors, leukemia viral oncogene homolog (ErbB2) receptor inhibitors, growth factor inhibitors, heat shock protein HSP-90 inhibitors, histone deacetylase (HDAC) inhibitors inhibitors, hormonal therapies, immunologicals, intercalating antibiotics, kinase inhibitors, mammalian target of rapomycin inhibitors, mitogen-activated extracellular signal-regulated kinase inhibitors, non-steroidal anti-inflammatory drugs (NSAID's), platinum chemotherapeutics, polo-like kinase inhibitors, proteasome inhibitors, purine analogs, pyrimidine analogs, receptor tyrosine kinase inhibitors, retinoids/deltoids plant alkaloids, topoisomerase inhibitors and the like.

Alkylating agents include altretamine, AMD-473, AP-5280, apaziquone, bendamustine, brostallicin, busulfan, carboquone, carmustine (BCNU), chlorambucil, Cloretazine™ (VNP 40101M), cyclophosphamide, decarbazine, estramustine, fotemustine, glufosfamide, ifosfamide, KW-2170, lomustine (CCNU), mafosfamide, melphalan, mitobronitol, mitolactol, nimustine, nitrogen mustard N-oxide, ranimustine, temozolomide, thiotepa, treosulfan, trofosfamide and the like.

Angiogenesis inhibitors include endothelial-specific receptor tyrosine kinase (Tie-2) inhibitors, epidermal growth factor receptor (EGFR) inhibitors, insulin growth factor-2 receptor (IGFR-2) inhibitors, matrix metalloproteinase-2 (MMP-2) inhibitors, matrix metalloproteinase-9 (MMP-9) inhibitors, platelet-derived growth factor receptor (PDGFR) inhibitors, thrombospondin analogs vascular endothelial growth factor receptor tyrosine kinase (VEGFR) inhibitors and the like.

Aurora kinase inhibitors include AZD-1152, MLN-8054, VX-680 and the like.

Bcl protein family member inhibitors include AT-101 ((−) gossypol), GENASENSE® (G3139 or oblimersen (Bcl-2-targeting antisense oglionucleotide)), IPI-194, IPI-565, N-(4-(4-((4'-chloro(1,1'-biphenyl)-2-yl)methyl)piperazin-1-yl)benzoyl)-4-(((1R)-3-(dimethylamino)-1-((phenylsulfanyl)methyl)propyl)amino)-3-nitrobenzenesulfonamide) (ABT-737), N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide (ABT-263), GX-070 (obatoclax) and the like.

Bcr-Abl kinase inhibitors include DASATINIB® (BMS-354825), GLEEVEC® (imatinib) and the like.

CDK inhibitors include AZD-5438, BMI-1040, BMS-032, BMS-387, CVT-2584, flavopyridol, GPC-286199, MCS-5A, PD0332991, PHA-690509, seliciclib (CYC-202, R-roscovitine), ZK-304709 and the like.

COX-2 inhibitors include ABT-963, ARCOXIA® (etoricoxib), BEXTRA® (valdecoxib), BMS347070, CELEBREX™ (celecoxib), COX-189 (lumiracoxib), CT-3, DERAMAXX® (deracoxib), JTE-522, 4-methyl-2-(3,4-dimethylphenyl)-1-(4-sulfamoylphenyl-1H-pyrrole), MK-663 (etoricoxib), NS-398, parecoxib, RS-57067, SC-58125, SD-8381, SVT-2016, S-2474, T-614, VIOXX® (rofecoxib) and the like.

EGFR inhibitors include ABX-EGF, anti-EGFr immunoliposomes, EGF-vaccine, EMD-7200, ERBITUX® (cetuximab), HR3, IgA antibodies, IRESSA® (gefitinib), TARCEVA® (erlotinib or OSI-774), TP-38, EGFR fusion protein, TYKERB® (lapatinib) and the like.

ErbB2 receptor inhibitors include CP-724-714, CI-1033 (canertinib), Herceptin® (trastuzumab), TYKERB® (lapatinib), OMNITARG® (2C4, petuzumab), TAK-165, GW-572016 (ionafamib), GW-282974, EKB-569, PI-166, dHER2 (HER2 vaccine), APC-8024 (HER-2 vaccine), anti-HER/2neu bispecific antibody, B7.her21gG3, AS HER2 trifunctional bispecfic antibodies, mAB AR-209, mAB 2B-1 and the like.

Histone deacetylase inhibitors include depsipeptide, LAQ-824, MS-275, trapoxin, suberoylanilide hydroxamic acid (SAHA), TSA, valproic acid and the like.

HSP-90 inhibitors include 17-AAG-nab, 17-AAG, CNF-101, CNF-1010, CNF-2024, 17-DMAG, geldanamycin, IPI-504, KOS-953, MYCOGRAB®, NCS-683664, PU24FCl, PU-3, radicicol, SNX-2112, STA-9090 VER49009 and the like.

MEK inhibitors include ARRY-142886, ARRY-438162 PD-325901, PD-98059 and the like.

mTOR inhibitors include AP-23573, CCI-779, everolimus, RAD-001, rapamycin, temsirolimus and the like.

Non-steroidal anti-inflammatory drugs include AMIGESIC® (salsalate), DOLOBID® (diflunisal), MOTRIN® (ibuprofen), ORUDIS® (ketoprofen), RELAFEN® (nabumetone), FELDENE® (piroxicam) ibuprofin cream, ALEVE® and NAPROSYN® (naproxen), VOLTAREN® (diclofenac), INDOCIN® (indomethacin), CLINORIL® (sulindac), TOLECTIN® (tolmetin), LODINE® (etodolac), TORADOL® (ketorolac), DAYPRO® (oxaprozin) and the like.

PDGFR inhibitors include C-451, CP-673, CP-868596 and the like.

Platinum chemotherapeutics include cisplatin, ELOXATIN® (oxaliplatin) eptaplatin, lobaplatin, nedaplatin, PARAPLATIN® (carboplatin), satraplatin and the like.

Polo-like kinase inhibitors include BI-2536 and the like.

Thrombospondin analogs include ABT-510, ABT-567, ABT-898, TSP-1 and the like.

VEGFR inhibitors include AVASTIN® (bevacizumab), ABT-869, AEE-788, ANGIOZYME™, axitinib (AG-13736), AZD-2171, CP-547,632, IM-862, Macugen (pegaptamib), NEXAVAR® (sorafenib, BAY43-9006), pazopanib (GW-786034), (PTK-787, ZK-222584), SUTENT® (sunitinib, SU-11248), VEGF trap, vatalanib, ZACTIMA™ (vandetanib, ZD-6474) and the like.

Antimetabolites include ALIMTA® (premetrexed disodium, LY231514, MTA), 5-azacitidine, XELODA® (capecitabine), carmofur, LEUSTAT® (cladribine), clofarabine, cytarabine, cytarabine ocfosfate, cytosine arabinoside, decitabine, deferoxamine, doxifluridine, eflornithine, EICAR, enocitabine, ethnylcytidine, fludarabine, hydroxyurea, 5-fluorouracil (5-FU) alone or in combination with leucovorin, GEMZAR® (gemcitabine), hydroxyurea, ALKERAN® (melphalan), mercaptopurine, 6-mercaptopurine riboside, methotrexate, mycophenolic acid, nelarabine, nolatrexed, ocfosate, pelitrexol, pentostatin, raltitrexed, Ribavirin, triapine, trimetrexate, S-1, tiazofurin, tegafur, TS-1, vidarabine, UFT and the like.

Antibiotics include intercalating antibiotics aclarubicin, actinomycin D, amirubicin, annamycin, adriamycin, BLENOXANE™ (bleomycin), daunorubicin, CAELYX® or MYOCET® (doxorubicin), elsamitrucin, epirbucin, glarbuicin, ZAVEDOS® (idarubicin), mitomycin C, nemorubicin, neocarzinostatin, peplomycin, pirarubicin, rebeccamycin, stimalamer, streptozocin, VALSTAR® (valrubicin), zinostatin and the like.

Topoisomerase inhibitors include aclarubicin, 9-aminocamptothecin, amonafide, amsacrine, becatecarin, belotecan, BN-80915, CAMPTOSAR® (irinotecan hydrochloride), camptothecin, CARDIOXANE® (dexrazoxine), diflomotecan, edotecarin, ELLENCE® or PHARMORUBICIN® (epirubicin), etoposide, exatecan, 10-hydroxycamptothecin, gimatecan, lurtotecan, mitoxantrone, orathecin, pirarbucin, pixantrone, rubitecan, sobuzoxane, SN-38, tafluposide, topotecan and the like.

Antibodies include AVASTIN® (bevacizumab), CD40-specific antibodies, chTNT-1/B, denosumab, ERBITUX® (cetuximab), HUMAX-CD4 (zanolimumab), IGF1R-specific antibodies, lintuzumab, PANOREX® (edrecolomab), RENCAREX® (WX G250), RITUXAN® (rituximab), ticilimumab, trastuzimab and the like.

Hormonal therapies include ARIMIDLEX® (anastrozole), AROMASIN® (exemestane), arzoxifene, CASODEX® (bicalutamide), CETROTIDE® (cetrorelix), degarelix, deslorelin, DESOPAN® (trilostane), dexamethasone, DROGENIL®, (flutamide), EVISTA® (raloxifene), fadrozole, FARESTON® (toremifene), FASLODEX® (fulvestrant), FEMARA®, (letrozole), formestane, glucocorticoids, HECTOROL® or RENAGEL® (doxercalciferol), lasofoxifene, leuprolide acetate, MEGACE® (megesterol), MIFEPREX® (mifepristone), NILANDRON™ (nilutamide), NOLVADEX® (tamoxifen citrate), PLENAXIS™ (abarelix), predisone, PROPECIA® (finasteride), rilostane, SUPREFACT® (buserelin), TRELSTAR® (luteinizing hormone releasing hormone (LHRH)), vantas, VETORYL®, (trilostane or modrastane), ZOLADEX® (fosrelin, goserelin) and the like.

Deltoids and retinoids include seocalcitol (EB1089, CB1093), lexacalcitrol (KH1060), fenretinide, PANRETIN® (aliretinoin), ATRAGEN® (liposomal tretinoin), TARGRETIN® (bexarotene), LGD-1550 and the like.

Plant alkaloids include, but are not limited to, vincristine, vinblastine, vindesine, vinorelbine and the like.

Proteasome inhibitors include VELCADE® (bortezomib), MG132, NPI-0052, PR-171 and the like.

Examples of immunologicals include interferons and other immune-enhancing agents. Interferons include interferon alpha, interferon alpha-2a, interferon alpha-2b, interferon beta, interferon gamma-1a, ACTIMMUNE® (interferon gamma-1b), interferon gamma-nl, combinations thereof and the like. Other agents include ALFAFERONE®, BAM-002, BEROMUN® (tasonermin), BEXXAR® (tositumomab), CamPath® (alemtuzumab), CTLA4 (cytotoxic lymphocyte antigen 4), decarbazine, denileukin, epratuzumab, GRANOCYTE® (lenograstim), lentinan, leukocyte alpha interferon, imiquimod, MDX-010, melanoma vaccine, mitumomab, molgramostim, MYLOTARG™ (gemtuzumab ozogamicin), NEUPOGEN® (filgrastim), OncoVAC-CL, OvaRex® (oregovomab), pemtumomab (Y-muHMFG1), PROVENGE®, sargaramostim, sizofilan, teceleukin, TheraCys®, ubenimex, VIRULIZIN®, Z-100, WF-10, PROLEUKIN® (aldesleukin), ZADAXIN® (thymalfasin), ZENAPAX® (daclizumab), ZEVALIN® (90Y-Ibritumomab tiuxetan) and the like.

Biological response modifiers are agents that modify defense mechanisms of living organisms or biological responses, such as survival, growth or differentiation of tissue cells to direct them to have anti-tumor activity and include krestin, lentinan, sizofuran, picibanil PF-3512676 (CpG-8954), ubenimex and the like.

Pyrimidine analogs include cytarabine (ara C or Arabinoside C), cytosine arabinoside, doxifluridine, FLUDARA® (fludarabine), 5-FU (5-fluorouracil), floxuridine, GEMZAR® (gemcitabine), TOMUDEX® (ratitrexed), TROXATYL™ (triacetyluridine troxacitabine) and the like.

Purine analogs include LANVIS® (thioguanine) and PURI-NETHOL® (mercaptopurine).

Antimitotic agents include batabulin, epothilone D (KOS-862), N-(2-((4-hydroxyphenyl)amino)pyridin-3-yl)-4-methoxybenzenesulfonamide, ixabepilone (BMS 247550), paclitaxel, TAXOTERE® (docetaxel), PNU100940 (109881), patupilone, XRP-9881, vinflunine, ZK-EPO and the like.

Compounds of the present invention are also intended to be used as a radiosensitizer that enhances the efficacy of radiotherapy. Examples of radiotherapy include, but are not limited to, external beam radiotherapy, teletherapy, brachtherapy and sealed and unsealed source radiotherapy.

Additionally, compounds having Formula I may be combined with other chemptherapeutic agents such as ABRAXANE™ (ABI-007), ABT-100 (farnesyl transferase inhibitor), ADVEXIN®, ALTOCOR® or MEVACOR® (lovastatin), AMPLIGEN® (poly I:poly C12U, a synthetic RNA), APTOSYN™ (exisulind), AREDIA® (pamidronic acid), arglabin, L-asparaginase, atamestane (1-methyl-3,17-dione-androsta-1,4-diene), AVAGE® (tazarotne), AVE-8062, BEC2 (mitumomab), cachectin or cachexin (tumor necrosis factor), canvaxin (vaccine), CeaVac™ (cancer vaccine), CELEUK®

(celmoleukin), CEPLENE® (histamine dihydrochloride), CERVARIX™ (human papillomavirus vaccine), CHOP® (C: CYTOXAN® (cyclophosphamide); H: ADRIAMYCIN® (hydroxydoxorubicin); O: Vincristine (ONCOVIN®); P: prednisone), CyPat™, combrestatin A4P, DAB(389)EGF or TransMID-107R™ (diphtheria toxins), dacarbazine, dactinomycin, 5,6-dimethylxanthenone-4-acetic acid (DMXAA), eniluracil, EVIZON™ (squalamine lactate), DIMERICINE® (T4N5 liposome lotion), discodermolide, DX-8951f (exatecan mesylate), enzastaurin, EP0906, GARDASIL® (quadrivalent human papillomavirus (Types 6, 11, 16, 18) recombinant vaccine), gastrimmune, genasense, GMK (ganglioside conjugate vaccine), GVAX® (prostate cancer vaccine), halofuginone, histerelin, hydroxycarbamide, ibandronic acid, IGN-101, IL-13-PE38, IL-13-PE38QQR (cintredekin besudotox), IL-13-pseudomonas exotoxin, interferon-α, interferon-γ, JUNOVAN™ or MEPACT™ (mifamurtide), lonafarnib, 5,10-methylenetetrahydrofolate, miltefosine (hexadecylphosphocholine), NEOVASTAT® (AE-941), NEUTREXIN® (trimetrexate glucuronate), NIPENT® (pentostatin), ONCONASE® (a ribonuclease enzyme), ONCOPHAGE® (melanoma vaccine treatment), OncoVAX (IL-2 Vaccine), ORATHECIN™ (rubitecan), OSIDEM® (antibody-based cell drug), OvaRex® MAb (murine monoclonal antibody), paditaxel, PANDIMEX™ (aglycone saponins from ginseng comprising 20(S)protopanaxadiol (aPPD) and 20(S)protopanaxatriol (aPPT)), panitumumab, PANVAC®-VF (investigational cancer vaccine), pegaspargase, PEG Interferon A, phenoxodiol, procarbazine, rebimastat, REMOVAB (catumaxomab), REVLIMID® (lenalidomide), RSR13 (efaproxiral), SOMATULINE® LA (lanreotide), SORIATANE® (acitretin), staurosporine (Streptomyces staurospores), talabostat (PT100), TARGRETIN® (bexarotene), Taxoprexin® (DHA-paclitaxel), TELCYTA™ (TLK286), temilifene, TEMODAR® (temozolomide), tesmilifene, thalidomide, THERATOPE® (STn-KLH), thymitaq (2-amino-3,4-dihydro-6-methyl-4-oxo-5-(4-pyridylthio)quinazoline dihydrochloride), TNFerade™ (adenovector: DNA carrier containing the gene for tumor necrosis factor-α), TRACLEER® or ZAVESCA® (bosentan), tretinoin (Retin-A), tetrandrine, TRISENOX® (arsenic trioxide), VIRULIZIN®, ukrain (derivative of alkaloids from the greater celandine plant), vitaxin (anti-alphavbeta3 antibody), XCYTRIN® (motexafin gadolinium), XINLAY™ (atrasentan), XYOTAX™ (paclitaxel poliglumex), YONDELIS™ (trabectedin), ZD-6126, ZINECARD® (dexrazoxane), zometa (zolendronic acid), zorubicin and the like.

It is also expected that compounds having Formula I would inhibit growth of cells derived from a pediatric cancer or neoplasm including embryonal rhabdomyosarcoma, pediatric acute lymphoblastic leukemia, pediatric acute myelogenous leukemia, pediatric alveolar rhabdomyosarcoma, pediatric anaplastic ependymoma, pediatric anaplastic large cell lymphoma, pediatric anaplastic medulloblastoma, pediatric atypical teratoid/rhabdoid tumor of the central nervous system, pediatric biphenotypic acute leukemia, pediatric Burkitts lymphoma, pediatric cancers of Ewing's family of tumors such as primitive neuroectodermal rumors, pediatric diffuse anaplastic Wilm's tumor, pediatric favorable histology Wilm's tumor, pediatric glioblastoma, pediatric medulloblastoma, pediatric neuroblastoma, pediatric neuroblastoma-derived myelocytomatosis, pediatric pre-B-cell cancers (such as leukemia), pediatric psteosarcoma, pediatric rhabdoid kidney tumor, pediatric rhabdomyosarcoma, and pediatric T-cell cancers such as lymphoma and skin cancer and the like (commonly-owned U.S. application Ser. No. 10/988,338), Cancer Res., 2000, 60, 6101-10); and autoimmune disorders include, acquired immunodeficiency disease syndrome, autoimmune lymphoproliferative syndrome, hemolytic anemia, inflammatory diseases, thrombocytopenia and the like (Current Allergy and Asthma Reports 2003, 3:378-384; Br. J. Haematol. 2000 September; 110(3): 584-90; Blood 2000 Feb. 15; 95(4):1283-92; and New England Journal of Medicine 2004 September; 351(14): 1409-1418).

For example, involvement of Aurora-kinases in bladder cancer, breast cancer, cervical cancer, colon cancer, endometrial cancer, esophageal cancer, lung cancer, ovarian cancer, pancreatic cancer, prostate cancer, rectal cancer, skin cancer, stomach cancer and thyroid cancer is reported in Nature Reviews/Cancer, Vol. 4 December, 2004.

Compounds having Formula I may be made by synthetic chemical processes, examples of which are shown herein. It is meant to be understood that the order of the steps in the processes may be varied, that reagents, solvents and reaction conditions may be substituted for those specifically mentioned, and that vulnerable moieties may be protected and deprotected, as necessary.

Protecting groups for C(O)OH moieties include, but are not limited to, acetoxymethyl, allyl, benzoylmethyl, benzyl, benzyloxymethyl, tert-butyl, tert-butyldiphenylsilyl, diphenylmethyl, cyclobutyl, cyclohexyl, cyclopentyl, cyclopropyl, diphenylmethylsilyl, ethyl, para-methoxybenzyl, methoxymethyl, methoxyethoxymethyl, methyl, methylthiomethyl, naphthyl, para-nitrobenzyl, phenyl, n-propyl, 2,2,2-trichloroethyl, triethylsilyl, 2-(trimethylsilyl)ethyl, 2-(trimethylsilyl)ethoxymethyl, triphenylmethyl and the like.

Protecting groups for C(O) and C(O)H moieties include, but are not limited to, 1,3-dioxylketal, diethylketal, dimethylketal, 1,3-dithianylketal, O-methyloxime, O-phenyloxime and the like.

Protecting groups for NH moieties include, but are not limited to, acetyl, alanyl, benzoyl, benzyl (phenylmethyl), benzylidene, benzyloxycarbonyl (Cbz), tert-butoxycarbonyl (Boc), 3,4-dimethoxybenzyloxycarbonyl, diphenylmethyl, diphenylphosphoryl, formyl, methanesulfonyl, para-methoxybenzyloxycarbonyl, phenylacetyl, phthaloyl, succinyl, trichloroethoxycarbonyl, triethylsilyl, trifluoroacetyl, trimethylsilyl, triphenylmethyl, triphenylsilyl, para-toluenesulfonyl and the like.

Protecting groups for OH and SH moieties include, but are not limited to, acetyl, allyl, allyloxycarbonyl, benzyloxycarbonyl (Cbz), benzoyl, benzyl, tert-butyl, tert-butyldimethylsilyl, tert-butyldiphenylsilyl, 3,4-dimethoxybenzyl, 3,4-dimethoxybenzyloxycarbonyl, 1,1-dimethyl-2-propenyl, diphenylmethyl, formyl, methanesulfonyl, methoxyacetyl, 4-methoxybenzyloxycarbonyl, para-methoxybenzyl, methoxycarbonyl, methyl, para-toluenesulfonyl, 2,2,2-trichloroethoxycarbonyl, 2,2,2-trichloroethyl, triethylsilyl, trifluoroacetyl, 2-(trimethylsilyl)ethoxycarbonyl, 2-trimethylsilylethyl, triphenylmethyl, 2-(triphenylphosphonio)ethoxycarbonyl and the like.

The following abbreviations have the meanings indicated. ADDP means 1,1'-(azodicarbonyl)dipiperidine; AD-mix-β means a mixture of (DHQD)$_2$PHAL, K$_3$Fe(CN)$_6$, K$_2$CO$_3$ and K$_2$SO$_4$); AIBN means 2,2'-azobis(2-methylpropionitrile); 9-BBN means 9-borabicyclo(3.3.1)nonane; Cp means cyclopentadiene; (DHQD)$_2$PHAL means hydroquinidine 1,4-phthalazinediyl diethyl ether; DBU means 1,8-diazabicyclo (5.4.0)undec-7-ene; DIBAL means diisobutylaluminum hydride; DIEA means diisopropylethylamine; DMAP means N,N-dimethylaminopyridine; DME means 1,2-dimethoxyethane; DMF means N,N-dimethylformamide; dmpe means 1,2-bis(dimethylphosphino)ethane; DMSO means dimethylsulfoxide; dppa means diphenylphosphoryl azide; dppb means 1,4-bis(diphenylphosphino)butane; dppe means 1,2-bis(diphenylphosphino)ethane; dppf means 1,1'-bis(diphenylphosphino)ferrocene; dppm means 1,1-bis(diphenylphosphino)methane; EDAC means 1-(3-dimethylaminopropyl)-3-ethylcarbodiimide; Fmoc means fluorenylmethoxycarbonyl; HATU means O-(7-azabenzotriazol-1-yl)-N,N'N'N'-tetramethyluronium hexafluorophosphate; HMPA means hexamethylphosphoramide; HOAT means 1-hydroxy-7-azabenzotriazole; IPA means isopropyl alcohol; LDA means lithium diisopropylamide; LHMDS means lithium bis(hexamethyldisilylamide); MP-BH$_3$ means macroporus triethylammonium methylpolystyrene cyanoborohydride; LAH means lithium aluminum hydride; NCS means N-chlorosuccinimide; PyBOP means benzotriazol-1-yloxytripyrrolidinophosphonium hexafluorophosphate; TBTU means O-benzotriazol-1-yl-N,N,N',N'-tetramethyluronium tetrafluoroborate; TDA-1 means tris(2-(2-methoxyethoxy)ethyl)amine; TEA means triethylamine; TFA means trifluoroacetic acid; THF means tetrahydrofuran; NCS means N-chlorosuccinimide; NMM means N-methylmorpholine; NMP means N-methylpyrrolidine; PPh$_3$ means triphenylphosphine.

The following schemes and examples are presented to provide what is believed to be the most useful and readily understood description of procedures and conceptual aspects of this invention.

SCHEME 1

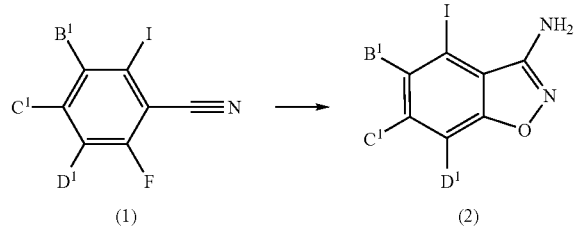

As shown in SCHEME 1, compounds having Formula (1) can be converted to compounds having Formula (2) by reacting the former, N-hydroxyacetamide and potassium tert-butoxide. The reaction is typically conducted at ambient temperature in a solvent such as DMF, DME, NMP or a mixture thereof.

SCHEME 2

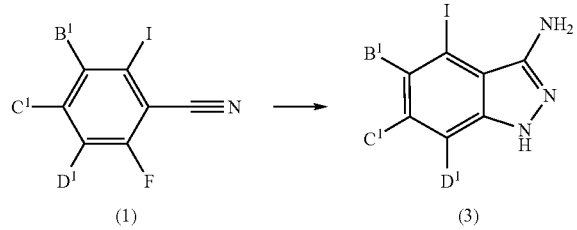

As shown in SCHEME 2, compounds having Formula (1) can be converted to compounds having Formula (3) by reacting the former and hydrazine. The reaction is typically conducted in refluxing ethanol.

SCHEME 3

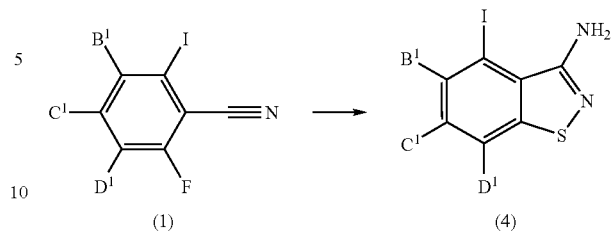

As shown in SCHEME 3, compounds having Formula (1) can be converted to compounds having Formula (4) by reacting the former, phenylmethanethiol and potassium tert-butoxide and reacting the product thereform with sulfuryl chloride and then ammonia. The reactions are typically conducted at ambient temperature in a solvent such as THF, dichloromethane, methanol or a mixture thereof.

SCHEME 4

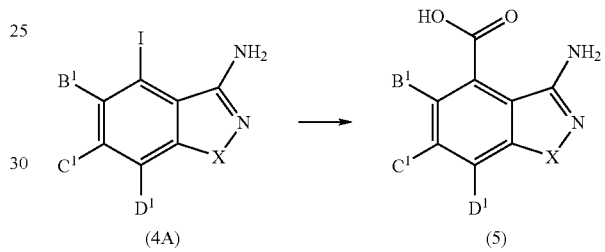

As shown in SCHEME 4, compounds having Formula (4A) can be converted to compounds having Formula (5) by reacting the former, carbon monoxide, a palladium catalyst, and a base, followed by hydrolysis of the ester. Examples of palladium catalysts include (1,1'-bis(diphenylphosphino)ferrocene)dichloropalladium(II), bis(triphenylphosphine)palladium(II) dichloride and the like. Examples of bases include TEA and potassium carbonate. The reaction is typically conducted at elevated temperatures in a solvent such as methanol or ethanol. Hydrolysis of the ester is typically performed using a aqueous base such as but not limited to LiOH in a solvent such as but not limited to methanol, THF and the like or mixtures thereof.

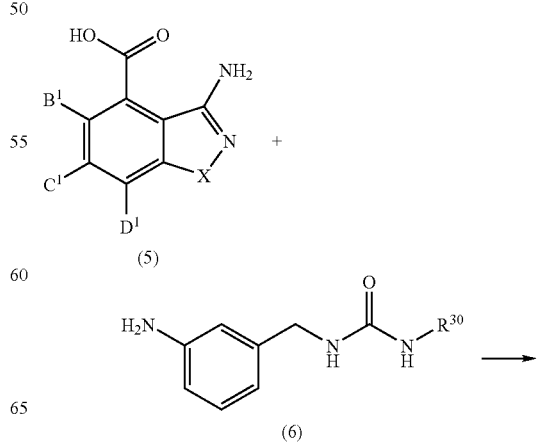

-continued

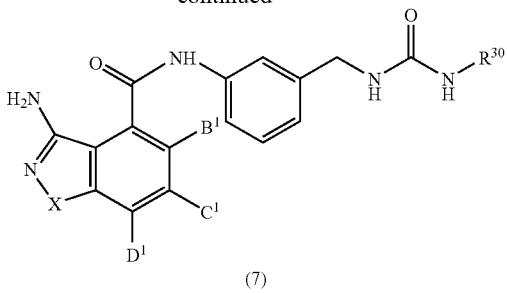

(7)

As shown in SCHEME 5, compounds having Formula (5) can be converted to compounds having formula (7) by reacting the former, compounds having Formula (6), a coupling agent and a base, with or without a coupling auxiliary. Examples of coupling agents include DCC, EDCI, HATU, TBTU and the like. Examples of bases include DIEA, TEA, NMM and the like. Examples of coupling auxiliaries include DMAP, HOAT, HOBT and the like. The reaction is typically conducted between about 25° C. and about 45° C., over about 1 to about 24 hours, in a solvent such as THF, DMF, dichloromethane, ethyl acetate or a mixture thereof.

As shown in SCHEME 6, compounds having Formula (5) can be converted to compounds having formula (9) by reacting the former and compounds having Formula (8) as described for the conversion of compounds having Formula (5) to compounds having Formula (7) in SCHEME 5.

Compounds having Formula (9) can be converted to compounds having Formula (10) by reacting the former and an acid. Examples of acids include TFA or HCl. The reaction is typically conducted at ambient temperature in a solvent such as dichloromethane, dioxane, ethyl acetate or a mixture thereof.

Compounds having Formula (10) can be converted to compounds having Formula (11) by reacting the former and compounds having formula $R^{30}NCO$, with or without a base. Examples of bases include TEA, DIEA and the like. The reaction is typically initially conducted below room temperature and then warmed to room temperature.

Alternatively, compounds having Formula (10) can be converted to compounds having Formula (12) by reacting the former and compounds having formula $R^{30}COH$ as described for the conversion of compounds having Formula (5) to compounds having Formula (7) in SCHEME 5.

SCHEME 6

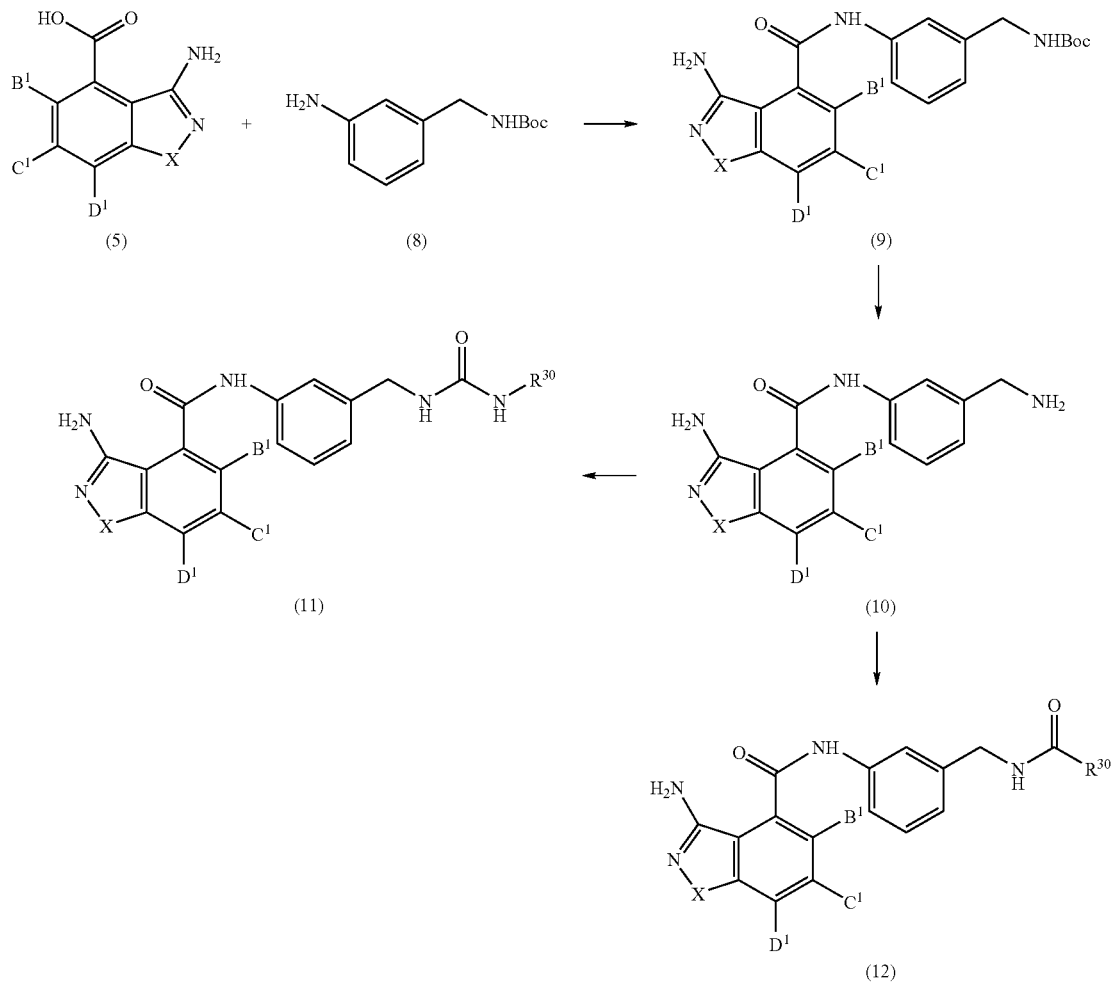

EXAMPLE 1

3-amino-N-(3-(((((3-fluorophenyl)amino)carbonyl)amino)methyl)phenyl)-1,2-benzisoxazole-4-carboxamide

EXAMPLE 1A

A mixture of N-hydroxyacetamide (7.37 g) in DMF (100 mL) was treated with potassium tert-butoxide (11 g), stirred at room temperature for 30 minutes, treated with 2-fluoro-6-iodobenzonitrile (12.1 g), stirred at room temperature for 8 hours, diluted with water and filtered.

EXAMPLE 1B

A mixture of EXAMPLE 1A (8.5 g), (1,1'-bis(diphenylphosphino)ferrocene)dichloropalladium(II) (940 mg) and TEA (6.2 mL) in methanol (100 mL) under 60 psi carbon monoxide was heated at 100° C. for 2 hours, cooled to room temperature and concentrated. The concentrate was dissolved in methanol (50 mL) and THF (100 mL), treated with 2M lithium hydroxide (50 mL), stirred at room temperature for 2 hours, diluted with water and washed with diethyl ether. The aqueous layer was neutralized to pH 4-5 with 3N HCl and filtered.

EXAMPLE 1C

A mixture of 3-(aminomethyl)aniline (1.12 g) in dichloromethane (40 mL) at −30° C. was treated with 1-fluoro-3-isocyanatobenzene (1.03 mL), warmed to room temperature, stirred for 30 minutes and filtered. The solid was suspended in 100 mL of 4N HCl, stirred at room temperature for 30 minutes and filtered. The filtrate was neutralized with 10% aqueous NaOH and filtered.

EXAMPLE 1D 3-amino-N-(3-(((((3-fluorophenyl)amino)carbonyl)amino)methyl)phenyl)-1,2-benzisoxazole-4-carboxamide A mixture of EXAMPLE 1B (0.036 g), EXAMPLE 1C (0.052 g), HATU (0.077 g) and TEA (0.078 mL) in DMF (2 mL) was stirred at room temperature for 24 hours, diluted with water and extracted with ethyl acetate. The extract was washed (brine) and dried ($MgSO_4$), filtered and concentrated. The concentrate was flash chromatographed on silica gel with 0-5% methanol in dichloromethane. $^1$H NMR (300 MHz, DMSO-$d_6$) δ 4.32 (d, J=5.76 Hz, 2H) 6.32 (s, 2H) 6.63-6.82 (m, 2H) 7.08 (dd, J=17.97, 8.48 Hz, 2H) 7.17-7.54 (m, 3H) 7.58-7.86 (m, 5H) 8.83 (s, 1H) 10.79 (s, 1H).

EXAMPLE 2

3-amino-N-(3-(((((2-fluorophenyl)amino)carbonyl)amino)methyl)phenyl)-1,2-benzisoxazole-4-carboxamide The title compound was prepared by substituting 1-fluoro-2-isocyanatobenzene for 1-fluoro-3-isocyanatobenzene in EXAMPLES 1C-D. $^1$H NMR (300 MHz, DMSO-$d_6$) δ 4.34 (d, J=6.10 Hz, 2H) 6.31 (s, 2H) 6.83-6.98 (m, 1H) 6.99-7.25 (m, 4H) 7.36 (t, J=7.80 Hz, 1H) 7.59-7.81 (m, 5H) 8.01-8.26 (m, 1H) 8.39 (d, J=2.37 Hz, 1H) 10.78 (s, 1H).

EXAMPLE 3

3-amino-N-(3-(((anilinocarbonyl)amino)methyl)phenyl)-1,2-benzisoxazole-4-carboxamide The title compound was prepared by substituting isocyanatobenzene for 1-fluoro-3-isocyanatobenzene in EXAMPLES 1C-D. $^1$H NMR (300 MHz, DMSO-$d_6$) δ 4.32 (d, J=6.10 Hz, 2H) 6.31 (s, 2H) 6.63 (t, J=5.93 Hz, 1H) 6.89 (t, J=7.29 Hz, 1H) 7.11 (d, J=7.80 Hz, 1H) 7.15-7.29 (m, 2H) 7.28-7.49 (m, 3H) 7.55-7.85 (m, 5H) 8.55 (s, 1H) 10.78 (s, 1H).

EXAMPLE 4

3-amino-N-(3-(((((4-(trifluoromethyl)phenyl)amino)carbonyl)amino)methyl)phenyl)-1,2-benzisoxazole-4-carboxamide The title compound was prepared by substituting 1-isocyanato-4-trifluoromethylbenzene for 1-fluoro-3-isocyanatobenzene in EXAMPLES 1C-D. $^1$H NMR (300 MHz, DMSO-$d_6$) δ 4.34 (d, J=5.95 Hz, 2H) 6.32 (s, 2H) 6.81 (t, J=5.95 Hz, 1H) 7.12 (d, J=7.93 Hz, 1H) 7.36 (t, J=7.93 Hz, 1H) 7.48-7.87 (m, 9H) 9.03 (s, 1H) 10.78 (s, 1H).

EXAMPLE 5

3-amino-N-(3-(((((4-methylphenyl)amino)carbonyl)amino)methyl)phenyl)-1,2-benzisoxazole-4-carboxamide

EXAMPLE 5A

A mixture of EXAMPLE 1B (1.0 g), tert-butyl 3-aminobenzylcarbamate (1.373 g), HATU (2.348 g) and TEA (2.347 mL) in DMF (30 mL) was stirred at room temperature for 24 hours, then diluted with water and extracted with ethyl acetate. The ethyl acetate phase was washed (brine), dried ($MgSO_4$) and filtered. The filtrate was evaporated to dryness to leave an oil which was triturated with water. The resulting precipitate was filtered and dried.

EXAMPLE 5B

A mixture of EXAMPLE 5A (1.6 g) in dichloromethane (10 mL) was treated with trifluoroacetic acid (5 mL), stirred at room temperature for 2 hours and concentrated.

EXAMPLE 5C 3-amino-N-(3-(((((4-methylphenyl)amino)carbonyl)amino)methyl)phenyl)-1,2-benzisoxazole-4-carboxamide A mixture of EXAMPLE 5B (51 mg) in DMF (2 mL) was treated with TEA (27.9 μL), cooled to −20° C., treated with 1-isocyanato-4-methylbenzene (13.3 mg), stirred for 30 minutes, then at room temperature for 30 minutes, treated with water and filtered. $^1$H NMR (300 MHz, DMSO-$d_6$) δ 2.21 (s, 3H) 4.31 (d, J=6.10 Hz, 2H) 6.32 (s, 2H) 6.58 (t, J=5.93 Hz, 1H) 6.91-7.21 (m, 3H) 7.21-7.42 (m, 3H) 7.53-7.84 (m, 5H) 8.44 (s, 1H) 10.79 (s, 1H).

EXAMPLE 6

3-amino-N-(3-(((((2-fluoro-5-methylphenyl)amino) carbonyl)amino)methyl)phenyl)-1,2-benzisoxazole-4-carboxamide The title compound was prepared by substituting 1-fluoro-2-isocyanato-4-methylbenzene for 1-isocyanato-4-methylbenzene in EXAMPLE 5C. $^1$H NMR (300 MHz, DMSO-$d_6$) δ 2.23 (s, 3H) 4.33 (d, J=5.76 Hz, 2H) 6.32 (s, 2H) 6.52-6.81 (m, 1H) 6.91-7.21 (m, 3H) 7.36 (t, J=7.80 Hz, 1H) 7.56-7.85 (m, 5H) 7.98 (dd, J=7.97, 1.86 Hz, 1H) 8.32 (d, J=2.37 Hz, 1H) 10.80 (s, 1H).

EXAMPLE 7

3-amino-N-(3-(((((3-methoxyphenyl)amino)carbonyl)amino)methyl)phenyl)-1,2-benzisoxazole-4-carboxamide The title compound was prepared by substituting 1-isocyanato-3-methoxylbenzene for 1-isocyanato-4-methylbenzene in EXAMPLE 5C. $^1$H NMR (300 MHz, DMSO-$d_6$) δ 3.70 (s, 3H) 4.32 (d, J=5.95 Hz, 2H) 6.31 (s, 2H) 6.47 (dd, J=7.73, 2.18 Hz, 1H) 6.63 (t, J=5.95 Hz, 1H) 6.79-7.01 (m, 1H) 7.03-7.23 (m, 3H) 7.35 (t, J=7.93 Hz, 1H) 7.55-7.87 (m, 5H) 8.58 (s, 1H) 10.79 (s, 1H).

EXAMPLE 8

3-amino-N-(3-(((((4-methoxyphenyl)amino)carbonyl)amino)methyl)phenyl)-1,2-benzisoxazole-4-carboxamide The title compound was prepared by substituting 1-isocyanato-4-methoxylbenzene for 1-isocyanato-4-methylbenzene in EXAMPLE 5C. $^1$H NMR (300 MHz, DMSO-$d_6$) δ 3.69 (s, 3H) 4.31 (d, J=5.95 Hz, 2H) 6.32 (s, 2H) 6.53 (t, J=5.95 Hz, 1H) 6.81 (d, J=9.12 Hz, 2H) 7.10 (d, J=7.54 Hz, 1H) 7.21-7.49 (m, 3H) 7.54-7.86 (m, 5H) 8.35 (s, 1H) 10.78 (s, 1H).

EXAMPLE 9

3-amino-N-(3-(((((3,4-difluorophenyl)amino)carbonyl)amino)methyl)phenyl)-1,2-benzisoxazole-4-carboxamide The title compound was prepared by substituting 1,2-difluoro-4-isocyanatobenzene for 1-isocyanato-4-methylbenzene in EXAMPLE 5C. $^1$H NMR (300 MHz, DMSO-$d_6$) δ 4.32 (d, J=5.76 Hz, 2H) 6.32 (s, 2H) 6.74 (t, J=5.93 Hz, 1H) 6.94-7.17 (m, 2H) 7.17-7.46 (m, 2H) 7.51-7.88 (m, 6H) 8.83 (s, 1H) 10.78 (s, 1H).

EXAMPLE 10

3-amino-N-(3-(((((3,5-difluorophenyl)amino)carbonyl)amino)methyl)phenyl)-1,2-benzisoxazole-4-carboxamide The title compound was prepared by substituting 1,3-difluoro-5-isocyanatobenzene for 1-isocyanato-4-methylbenzene in EXAMPLE 5C. $^1$H NMR (300 MHz, DMSO-$d_6$) δ 4.32 (d, J=5.95 Hz, 2H) 6.31 (s, 2H) 6.69 (s, 1H) 6.86 (s, 1H) 7.01-7.24 (m, 3H) 7.35 (t, J=7.93 Hz, 1H) 7.57-7.86 (m, 5H) 9.04 (s, 1H) 10.78 (s, 1H).

EXAMPLE 11

3-amino-N-(3-(((((4-fluorophenyl)amino)carbonyl)amino)methyl)phenyl)-1,2-benzisoxazole-4-carboxamide The title compound was prepared by substituting 1-fluoro-4-isocyanatobenzene for 1-isocyanato-4-methylbenzene in EXAMPLE 5C. $^1$H NMR (300 MHz, DMSO-$d_6$) δ 4.32 (d, J=6.10 Hz, 2H) 6.32 (s, 2H) 6.63 (t, J=5.93 Hz, 1H) 6.97-7.16 (m, 3H) 7.30-7.51 (m, 3H) 7.58-7.84 (m, 5H) 8.60 (s, 1H) 10.78 (s, 1H).

EXAMPLE 12

3-amino-N-(3-((((cyclopentylamino)carbonyl)amino)methyl)phenyl)-1,2-benzisoxazole-4-carboxamide The title compound was prepared by substituting isocyanatocyclopentane for 1-isocyanato-4-methylbenzene in EXAMPLE 5C. $^1$H NMR (300 MHz, DMSO-$d_6$) δ 1.22-1.40 (m, 2H) 1.42-1.67 (m, 4H) 1.70-1.90 (m, 2H) 3.70-4.03 (m, 1H) 4.22 (d, J=5.76 Hz, 2H) 5.92 (d, J=7.46 Hz, 1H) 6.17 (t, J=5.93 Hz, 1H) 6.32 (s, 2H) 7.05 (d, J=7.46 Hz, 1H) 7.33 (t, J=7.80 Hz, 1H) 7.52-7.90 (m, 5H) 10.76 (s, 1H).

EXAMPLE 13

3-amino-N-(3-((((cyclohexylamino)carbonyl)amino)methyl)phenyl)-1,2-benzisoxazole-4-carboxamide The title compound was prepared by substituting isocyanatocyclohexane for 1-isocyanato-4-methylbenzene in EXAMPLE 5C. $^1$H NMR (300 MHz, DMSO-$d_6$) δ 0.82-1.37 (m, 6H) 1.40-1.87 (m, 5H) 4.21 (d, J=5.76 Hz, 2H) 5.83 (d, J=8.14 Hz, 1H) 6.20 (t, J=5.93 Hz, 1H) 6.33 (s, 2H) 7.04 (d, J=7.80 Hz, 1H) 7.32 (t, J=7.80 Hz, 1H) 7.52-7.87 (m, 5H) 10.76 (s, 1H).

EXAMPLE 14

3-amino-N-(3-((((thien-2-ylamino)carbonyl)amino)methyl)phenyl)-1,2-benzisoxazole-4-carboxamide The title compound was prepared by substituting 2-isocyanatothiophene for 1-isocyanato-4-methylbenzene in EXAMPLE 5C. $^1$H NMR (300 MHz, DMSO-$d_6$) δ 4.33 (d, J=6.10 Hz, 2H) 6.31 (s, 2H) 6.44 (dd, J=3.22, 1.86 Hz, 1H) 6.65-6.78 (m, 3H) 7.10 (d, J=7.46 Hz, 1H) 7.35 (t, J=7.80 Hz, 1H) 7.59-7.80 (m, 5H) 9.55 (s, 1H) 10.78 (s, 1H).

EXAMPLE 15

3-amino-N-(3-((((thien-3-ylamino)carbonyl)amino)methyl)phenyl)-1,2-benzisoxazole-4-carboxamide The title compound was prepared by substituting 3-isocyanatothiophene for 1-isocyanato-4-methylbenzene in EXAMPLE 5C. $^1$H NMR (300 MHz, DMSO-$d_6$) δ 4.31 (d, J=5.95 Hz, 2H) 6.31 (s, 2H) 6.60 (s, 1H) 6.98 (d, J=5.16 Hz, 1H) 7.10 (d, J=7.54 Hz, 1H) 7.17 (d, J=1.98 Hz, 1H) 7.25-7.43 (m, 2H) 7.55-7.84 (m, 5H) 8.84 (s, 1H) 10.78 (s, 1H).

EXAMPLE 16

3-amino-N-(3-(((((3-methylphenyl)amino)carbonyl)amino)methyl)phenyl)-1,2-benzisoxazole-4-carboxamide The title compound was prepared by substituting 1-isocyanato-3-methylbenzene for 1-isocyanato-4-methylbenzene in EXAMPLE 5C. $^1$H NMR (300 MHz, DMSO-$d_6$) δ 2.24 (s, 3H) 4.31 (d, J=5.43 Hz, 2H) 6.31 (s, 2H) 6.53-6.79 (m, 2H) 7.02-7.44 (m, 5H) 7.57-7.90 (m, 5H) 8.47 (s, 1H) 10.78 (s, 1H).

EXAMPLE 17

3-amino-N-(3-(((((3,5-dimethylphenyl)amino)carbonyl)amino)methyl)phenyl)-1,2-benzisoxazole-4-carboxamide The title compound was prepared by substituting 1,3-dimethyl-5-isocyanatobenzene for 1-isocyanato-4-methylbenzene in EXAMPLE 5C. $^1$H NMR (300 MHz, DMSO-$d_6$) δ 2.19 (s, 6H) 4.30 (d, J=5.55 Hz, 2H) 6.32 (s, 2H) 6.48-6.76 (m, 2H) 7.03 (s, 2H) 7.10 (d, J=7.93 Hz, 1H) 7.35 (t, J=7.73 Hz, 1H) 7.53-7.85 (m, 5H) 8.39 (s, 1H) 10.78 (s, 1H).

EXAMPLE 18

3-amino-N-(3-(((((3-chlorophenyl)amino)carbonyl)amino)methyl)phenyl)-1,2-benzisoxazole-4-carboxamide The title compound was prepared by substituting 1-chloro-3-isocyanatobenzene for 1-isocyanato-4-methylbenzene in EXAMPLE 5C. $^1$H NMR (300 MHz, DMSO-$d_6$) δ 4.32 (d, J=5.95 Hz, 2H) 6.32 (s, 2H) 6.75 (t, J=5.95 Hz, 1H) 6.85-6.99 (m, 1H) 7.11 (d, J=7.93 Hz, 1H) 7.16-7.28 (m, 2H) 7.35 (t, J=7.73 Hz, 1H) 7.54-7.88 (m, 6H) 8.81 (s, 1H) 10.78 (s, 1H).

EXAMPLE 19

3-amino-N-(3-(((((2-(trifluoromethyl)phenyl)amino)carbonyl)amino)methyl)phenyl)-1,2-benzisoxazole-4-carboxamide The title compound was prepared by substituting 1-isocyanato-2-trifluoromethylbenzene for 1-isocyanato-4-methylbenzene in EXAMPLE 5C. $^1$H NMR (300 MHz, DMSO-$d_6$) δ 4.34 (d, J=5.76 Hz, 2H) 6.31 (s, 2H) 7.04-7.26 (m, 2H) 7.38 (t, J=7.80 Hz, 1H) 7.45-7.83 (m, 8H) 7.87 (s, 1H) 8.00 (d, J=8.14 Hz, 1H) 10.79 (s, 1H).

EXAMPLE 20

3-amino-N-(3-(((3-methylbenzoyl)amino)methyl)phenyl)-1,2-benzisoxazole-4-carboxamide The title compound was prepared by substituting EXAMPLE 5B and 3-methylbenzoic acid for EXAMPLES 1C and 1B, respectively, in EXAMPLE 1D. $^1$H NMR (300 MHz, DMSO-$d_6$) δ 2.36 (s, 3H) 4.49 (d, J=6.10 Hz, 2H) 6.31 (s, 2H) 7.13 (d, J=7.80 Hz, 1H) 7.25-7.49 (m, 3H) 7.54-7.91 (m, 7H) 9.02 (t, J=5.93 Hz, 1H) 10.78 (s, 1H).

EXAMPLE 21

3-amino-N-(3-((benzoylamino)methyl)phenyl)-1,2-benzisoxazole-4-carboxamide

The title compound was prepared by substituting EXAMPLE 5B and benzoic acid for EXAMPLES 1C and 1B, respectively, in EXAMPLE 1D. $^1$H NMR (300 MHz, DMSO-$d_6$) δ 4.51 (d, J=6.10 Hz, 2H) 6.31 (s, 2H) 7.13 (d, J=7.80 Hz, 1H) 7.35 (t, J=7.97 Hz, 1H) 7.41-7.60 (m, 3H) 7.60-7.83 (m, 5H) 7.82-8.00 (m, 2H) 9.07 (t, J=5.93 Hz, 1H) 10.77 (s, 1H).

EXAMPLE 22

3-amino-N-(3-(((phenylacetyl)amino)methyl)phenyl)-1,2-benzisoxazole-4-carboxamide The title compound was prepared by substituting EXAMPLE 5B and 2-phenylacetic acid for EXAMPLES 1C and 1B, respectively, in EXAMPLE 1D. $^1$H NMR (300 MHz, DMSO-$d_6$) δ 3.49 (s, 2H) 4.29 (d, J=5.76 Hz, 2H) 6.33 (s, 2H) 7.04 (d, J=8.14 Hz, 1H) 7.12-7.42 (m, 6H) 7.53-7.85 (m, 5H) 8.58 (t, J=5.76 Hz, 1H) 10.76 (s, 1H).

EXAMPLE 23

3-amino-N-(4-((((3-fluorophenyl)amino)carbonyl)amino)phenyl)-1,2-benzisoxazole-4-carboxamide

EXAMPLE 23A

A mixture of (4-aminophenyl)carbamic acid tert-butyl ester (1.04 g) in dichloromethane (20 mL) at 0° C. was treated with 1-fluoro-3-isocyanatobenzene (0.56 mL), stirred at ambient temperature for 4 hours and filtered. The filtrate was suspended in dichloromethane (20 mL), cooled in an ice bath, treated with trifluoroacetic acid (5 mL), stirred for 15 minutes at 0° C., then at ambient temperature for 3 hours, and concentrated. The concentrate was reconcentrated twice from methanol and toluene and dried.

EXAMPLE 23B 3-amino-N-(4-((((3-fluorophenyl)amino)carbonyl)amino)phenyl)-1,2-benzisoxazole-4-carboxamide A mixture of EXAMPLE 1B (35.6 mg), EXAMPLE 23A (72 mg), HATU (84 mg) and TEA (83 ul) in DMF (20 mL) at room temperature was stirred for 20 hours, poured into water (30 mL) and filtered. The filtrate was dried and suspended in refluxing diethyl ether. The mixture was cooled to room temperature, filtered and dried. $^1$H NMR (300 MHz, DMSO-$d_6$) δ 6.36 (s, 2H) 6.78 (t, J=8.31 Hz, 1H) 7.12 (d, J=7.80 Hz, 1H) 7.31 (q, J=7.80 Hz, 1H) 7.49 (t, J=8.48 Hz, 3H) 7.61-7.85 (m, 5H) 8.76 (s, 1H) 8.88 (s, 1H) 10.69 (s, 1H).

EXAMPLE 24

3-amino-N-(4-((anilinocarbonyl)amino)phenyl)-1,2-benzisoxazole-4-carboxamide

The title compound was prepared by substituting isocyanatobenzene for 1-fluoro-3-isocyanatobenzene in EXAMPLES 23A-B. $^1$H NMR (300 MHz, DMSO-$d_6$) δ 6.36 (s, 2H) 6.97 (t, J=7.29 Hz, 1H) 7.28 (t, J=7.80 Hz, 2H) 7.46 (dd, J=8.14, 4.41 Hz, 4H) 7.58-7.84 (m, 5H) 8.64 (s, 1H) 8.69 (s, 1H) 10.69 (s, 1H).

EXAMPLE 25

3-amino-N-(4-((((3-(trifluoromethyl)phenyl)amino) carbonyl)amino)phenyl)-1,2-benzisoxazole-4-carboxamide The title compound was prepared by substituting isocyanato-3-trifluoromethylbenzene for 1-fluoro-3-isocyanatobenzene in EXAMPLES 23A-B. $^1$H NMR (300 MHz, DMSO-d$_6$) δ 6.36 (s, 2H) 7.31 (d, J=7.12 Hz, 1H) 7.43-7.61 (m, 4H) 7.63-7.81 (m, 5H) 8.03 (s, 1H) 8.83 (s, 1H) 9.04 (s, 1H) 10.70 (s, 1H).

EXAMPLE 26

3-amino-N-(4-(((thien-3-ylamino)carbonyl)amino) phenyl)-1,2-benzisoxazole-4-carboxamide The title compound was prepared by substituting 3-isocyanatothiophene for 1-fluoro-3-isocyanatobenzene, in EXAMPLES 23A-B. $^1$H NMR (300 MHz, DMSO-d$_6$) δ 6.35 (s, 2H) 7.05 (dd, J=5.26, 1.53 Hz, 1H) 7.28 (dd, J=3.05, 1.36 Hz, 1H) 7.35-7.48 (m, 3H) 7.60-7.83 (m, 5H) 8.64 (s, 1H) 8.90 (s, 1H) 10.67 (s, 1H).

EXAMPLE 27

3-amino-N-(4-((((4-methylphenyl)amino)carbonyl) amino)phenyl)-1,2-benzisoxazole-4-carboxamide The title compound was prepared by substituting 1-isocyanato-4-methylbenzene for 1-fluoro-3-isocyanatobenzene, in EXAMPLES 23A-B. $^1$H NMR (300 MHz, DMSO-d$_6$) δ 2.07 (s, 3H) 6.35 (s, 2H) 7.08 (d, J=8.48 Hz, 2H) 7.34 (d, J=8.48 Hz, 2H) 7.46 (d, J=8.82 Hz, 2H) 7.55-7.99 (m, 6H) 8.52 (s, 1H) 8.63 (s, 1H).

EXAMPLE 28

3-amino-N-(4-((((3-methylphenyl)amino)carbonyl) amino)phenyl)-1,2-benzisoxazole-4-carboxamide The title compound was prepared by substituting 1-isocyanato-3-methylbenzene for 1-fluoro-3-isocyanatobenzene in EXAMPLES 23A-B. $^1$H NMR (300 MHz, DMSO-d$_6$) δ 2.28 (s, 3H) 6.35 (s, 2H) 7.11-7.26 (m, 2H) 7.30 (s, 1H) 7.47 (d, J=9.16 Hz, 2H) 7.59-7.86 (m, 6H) 8.55 (s, 1H) 8.66 (s, 1H) 10.67 (s, 1H).

EXAMPLE 29

3-amino-N-(4-((((2,4-difluorophenyl)amino)carbonyl)amino)phenyl)-1,2-benzisoxazole-4-carboxamide The title compound was prepared by substituting 2,4-difluoro-1-isocyanatobenzene for 1-fluoro-3-isocyanatobenzene, in EXAMPLES 23A-B. $^1$H NMR (300 MHz, DMSO-d$_6$) δ 6.35 (s, 2H) 6.91-7.13 (m, 1H) 7.21-7.39 (m, 1H) 7.40-7.54 (m, 2H) 7.57-7.86 (m, 5H) 7.97-8.21 (m, 1H) 8.48 (d, J=2.03 Hz, 1H) 9.04 (s, 1H) 10.69 (s, 1H).

EXAMPLE 30

3-amino-N-(4-((((3,5-difluorophenyl)amino)carbonyl)amino)phenyl)-1,2-benzisoxazole-4-carboxamide The title compound was prepared by substituting 1,3-difluoro-5-isocyanatobenzene for 1-fluoro-3-isocyanatobenzene, in EXAMPLES 23A-B. $^1$H NMR (500 MHz, DMSO-d$_6$ and D$_2$O) δ 6.71-6.84 (m, 1H) 7.14-7.23 (m, 2H) 7.43-7.52 (m, 2H) 7.66-7.73 (m, 3H) 7.73-7.78 (m, 2H).

EXAMPLE 31

3-amino-N-(4-(((((3,4-difluorophenyl)amino)carbonyl)amino)phenyl)-1,2-benzisoxazole-4-carboxamide The title compound was prepared by substituting 1,2-difluoro-4-isocyanatobenzene for 1-fluoro-3-isocyanatobenzene, in EXAMPLES 23A-B. $^1$H NMR (500 MHz, DMSO-d$_6$ and D$_2$O) δ 7.06-7.21 (m, 1H) 7.27-7.41 (m, 1H) 7.43-7.53 (m, 2H) 7.59-7.79 (m, 6H).

EXAMPLE 32

3-amino-N-(3-(((((3-fluorophenyl)amino)carbonyl) amino)methyl)phenyl)-7-methyl-1,2-benzisoxazole-4-carboxamide

EXAMPLE 32A

3-Amino-7-methylbenzo(d)isoxazole-4-carboxylic acid was prepared by substituting 4-iodo-7-methylbenzo(d)isoxazol-3-amine (prepared as in PCT application PCT/US2004/016166, published as WO2004/113304) for EXAMPLE 1A in EXAMPLE 1B.

EXAMPLE 32B 3-amino-N-(3-(((((3-fluorophenyl)amino)carbonyl) amino)methyl)phenyl)-7-methyl-1,2-benzisoxazole-4-carboxamide The title compound was prepared by substituting EXAMPLE 32A for EXAMPLE 1B in EXAMPLE 1D. $^1$H NMR (300 MHz, DMSO-d$_6$) δ 2.50 (d, J=2.03 Hz, 3H) 4.32 (d, J=5.76 Hz, 2H) 6.36 (s, 2H) 6.58-6.86 (m, 2H) 7.07 (dd, J=14.92, 8.48 Hz, 2H) 7.15-7.41 (m, 2H) 7.41-7.55 (m, 2H) 7.57-7.78 (m, 3H) 8.82 (s, 1H) 10.69 (s, 1H).

EXAMPLE 33

3-amino-N-(3-(((anilinocarbonyl)amino)methyl) phenyl)-7-methyl-1,2-benzisoxazole-4-carboxamide The title compound was prepared by substituting isocyanatobenzene for 1-fluoro-3-isocyanatobenzene and EXAMPLE 32A for EXAMPLE 1B in EXAMPLES 1C and EXAMPLE 1D, respectively. $^1$H NMR (300 MHz, DMSO-d$_6$) δ 2.50 (dd, J=3.57, 1.59 Hz, 3H) 4.32 (d, J=5.95 Hz, 2H) 6.36 (s, 2H) 6.63 (t, J=5.95 Hz, 1H) 6.89 (t, J=7.34 Hz, 1H) 7.10 (d, J=7.93 Hz, 1H) 7.16-7.27 (m, 2H) 7.29-7.44 (m, 3H) 7.49 (d, J=8.33 Hz, 1H) 7.59-7.79 (m, 3H) 8.55 (s, 1H) 10.70 (s, 1H).

EXAMPLE 34

3-amino-N-(4-(((((3-fluorophenyl)amino)carbonyl) amino)phenyl)-7-methyl-1,2-benzisoxazole-4-carboxamide The title compound was prepared by substituting EXAMPLE 32A for EXAMPLE 1B in EXAMPLE 23B. $^1$H NMR (300 MHz, DMSO-d$_6$) δ 2.34-2.56 (m, 3H) 6.41 (s, 2H)

6.64-6.87 (m, 1H) 7.12 (d, J=9.15 Hz, 1H) 7.21-7.37 (m, 1H) 7.41-7.57 (m, 4H) 7.60-7.86 (m, 3H) 8.76 (s, 1H) 8.89 (s, 1H) 10.61 (s, 1H).

EXAMPLE 35

3-amino-N-(4-((anilinocarbonyl)amino)phenyl)-7-methyl-1,2-benzisoxazole-4-carboxamide The title compound was prepared by substituting isocyanatobenzene for 1-fluoro-3-isocyanatobenzene and EXAMPLE 32A for EXAMPLE 1B in EXAMPLES 23A and EXAMPLE 23B, respectively. $^1$H NMR (300 MHz, DMSO-$d_6$) δ 2.33-2.55 (m, 3H) 6.41 (s, 2H) 6.97 (t, J=7.46 Hz, 1H) 7.28 (t, J=7.97 Hz, 2H) 7.38-7.53 (m, 5H) 7.60-7.81 (m, 3H) 8.64 (s, 1H) 8.68 (s, 1H) 10.60 (s, 1H).

EXAMPLE 36

3-amino-N-(4-(benzoylamino)phenyl)-1,2-benzisoxazole-4-carboxamide

The title compound was prepared by substituting N-(4-aminophenyl)benzamide for 23A in EXAMPLE 23B. $^1$H NMR (300 MHz, DMSO-$d_6$) δ 6.36 (s, 2H) 7.42-8.06 (m, 12H) 10.29 (s, 1H) 10.77 (s, 1H).

EXAMPLE 37

3-amino-N-(3-(((((3-fluorophenyl)amino)carbonyl)amino)methyl)phenyl)-1,2-benzisothiazole-4-carboxamide

EXAMPLE 37A

The title compound was prepared by substituting 4-iodobenzo(d)isothiazol-3-amine (prepared as in PCT application PCT/US2004/016166, published as WO2004/113304) for EXAMPLE 1A in EXAMPLE 1B.

EXAMPLE 37B 3-amino-N-(3-(((((3-fluorophenyl)amino)carbonyl)amino)methyl)phenyl)-1,2-benzisothiazole-4-carboxamide The title compound was prepared by substituting EXAMPLE 37A for EXAMPLE 1B in EXAMPLE 1D. $^1$H NMR (300 MHz, DMSO-$d_6$) δ 4.32 (none, 1H) 6.48 (s, 2H) 6.61-6.79 (m, 2H) 6.96-7.15 (m, 2H) 7.17-7.28 (m, 1H) 7.35 (t, J=7.80 Hz, 1H) 7.41-7.53 (m, 1H) 7.58-7.71 (m, 3H) 7.74 (s, 1H) 8.17 (dd, J=7.63, 1.53 Hz, 1H) 8.82 (s, 1H) 10.86 (s, 1H).

EXAMPLE 38

3-amino-N-(3-(((anilinocarbonyl)amino)methyl)phenyl)-1,2-benzisothiazole-4-carboxamide The title compound was prepared by substituting isocyanatobenzene for 1-fluoro-3-isocyanatobenzene and EXAMPLE 37A for EXAMPLE 1B in EXAMPLES 1C and 1D, respectively. $^1$H NMR (300 MHz, DMSO-$d_6$) δ 4.32 (d, J=6.10 Hz, 2H) 6.48 (s, 2H) 6.63 (t, J=5.93 Hz, 1H) 6.89 (t, J=7.46 Hz, 1H) 7.05-7.29 (m, 3H) 7.29-7.49 (m, 3H) 7.53-7.83 (m, 4H) 8.17 (dd, J=7.63, 1.53 Hz, 1H) 8.55 (s, 1H) 10.86 (s, 1H).

EXAMPLE 39

3-amino-N-(3-(((((4-(trifluoromethyl)phenyl)amino)carbonyl)amino)methyl)phenyl)-1,2-benzisothiazole-4-carboxamide The title compound was prepared by substituting 1-isocyanato-4-trifluoromethylbenzene for 1-fluoro-3-isocyanatobenzene and EXAMPLE 37A for EXAMPLE 1B in EXAMPLES 1C and 1D, respectively. $^1$H NMR (500 MHz, DMSO-$d_6$) δ 4.34 (d, J=5.80 Hz, 2H) 6.49 (s, 2H) 6.83 (t, J=5.95 Hz, 1H) 7.12 (d, J=7.93 Hz, 1H) 7.36 (t, J=7.93 Hz, 1H) 7.50-7.71 (m, 7H) 7.76 (s, 1H) 8.17 (d, J=7.93 Hz, 1H) 9.04 (s, 1H) 10.87 (s, 1H).

EXAMPLE 40

3-amino-N-(4-((((3-fluorophenyl)amino)carbonyl)amino)phenyl)-1,2-benzisothiazole-4-carboxamide The title compound was prepared by substituting EXAMPLE 37A for EXAMPLE 1B in EXAMPLE 23B. $^1$H NMR (300 MHz, DMSO-$d_6$) δ 6.53 (s, 2H) 6.68-6.91 (m, 1H) 7.12 (d, J=8.14 Hz, 1H) 7.20-7.39 (m, 1H) 7.42-7.57 (m, 3H) 7.56-7.76 (m, 4H) 8.17 (dd, J=7.63, 1.53 Hz, 1H) 8.77 (s, 1H) 8.89 (s, 1H) 10.76 (s, 1H).

EXAMPLE 41

3-amino-N-(4-((anilinocarbonyl)amino)phenyl)-1,2-benzisothiazole-4-carboxamide

The title compound was prepared by substituting isocyanatobenzene for 1-fluoro-3-isocyanatobenzene and EXAMPLE 37A for EXAMPLE 1B in EXAMPLES 23A and EXAMPLE 23B, respectively. $^1$H NMR (300 MHz, DMSO-$d_6$) δ 6.53 (s, 2H) 6.97 (t, J=7.29 Hz, 1H) 7.28 (t, J=7.80 Hz, 2H) 7.46 (dd, J=8.14, 5.43 Hz, 4H) 7.58-7.78 (m, 4H) 8.17 (dd, J=7.63, 1.53 Hz, 1H) 8.64 (s, 1H) 8.69 (s, 1H) 10.75 (s, 1H).

EXAMPLE 42

3-amino-N-(4-((((3-(2-hydroxyethyl)phenyl)amino)carbonyl)amino)phenyl)-1,2-benzisothiazole-4-carboxamide The title compound was prepared by substituting EXAMPLE 37A and 1-(4-aminophenyl)-3-(3-(2-hydroxyethyl)phenyl)urea for EXAMPLE 1B and EXAMPLE 1C, respectively, in EXAMPLE 1D. $^1$H NMR (300 MHz, DMSO-$d_6$) δ 2.69 (t, J=7.14 Hz, 2H) 3.50-3.67 (m, 2H) 4.63 (t, J=5.16 Hz, 1H) 6.54 (s, 2H) 6.83 (d, J=7.54 Hz, 1H) 7.07-7.36 (m, 3H) 7.47 (d, J=8.72 Hz, 2H) 7.54-7.82 (m, 4H) 8.06-8.33 (m, 1H) 8.59 (s, 1H) 8.67 (s, 1H) 10.75 (s, 1H).

EXAMPLES 43-53 were prepared by substituting the appropriate isocyanate (X) for 1-fluoro-3-isocyanatobenzene in EXAMPLE 23A, and then substituting the product for EXAMPLE 23A in EXAMPLE 23B.

EXAMPLE 43

3-amino-N-(4-((((3,4-dichlorophenyl)amino)carbonyl)amino)phenyl)-1,2-benzisoxazole-4-carboxamide X=1,2-dichloro-4-isocyanatobenzene. $^1$H NMR (500 MHz, DMSO-$D_2$O) δ 7.34 (dd, J=8.70, 2.59 Hz, 1H) 7.45-7.50 (m, 2H) 7.53 (d, J=8.54 Hz, 1H) 7.66-7.77 (m, 5H) 7.88 (d, J=2.44 Hz, 1H).

EXAMPLE 44

3-amino-N-(4-((((3-methoxyphenyl)amino)carbonyl)amino)phenyl)-1,2-benzisoxazole-4-carboxamide X=1-isocyanato-3-methoxybenzene. $^1$H NMR (500 MHz, DMSO-D$_2$O) δ 3.74 (s, 3H) 6.58 (dd, J=8.24, 1.83 Hz, 1H) 6.82-7.02 (m, 1H) 7.10-7.27 (m, 2H) 7.40-7.51 (m, 2H) 7.60-7.83 (m, 5H).

EXAMPLE 45

3-amino-N-(4-((((4-bromophenyl)amino)carbonyl)amino)phenyl)-1,2-benzisoxazole-4-carboxamide X=1-bromo-4-isocyanatobenzene. $^1$H NMR (500 MHz, DMSO-D$_2$O) δ 7.36-7.50 (m, 6H) 7.63-7.79 (m, 5H).

EXAMPLE 46

3-amino-N-(4-((((4-fluorophenyl)amino)carbonyl)amino)phenyl)-1,2-benzisoxazole-4-carboxamide X=1-fluoro-4-isocyanatobenzene. $^1$H NMR (500 MHz, DMSO-D$_2$O) δ 7.09-7.18 (m, 2H) 7.41-7.51 (m, 4H) 7.64-7.78 (m, 5H).

EXAMPLE 47

3-amino-N-(4-((((4-chlorophenyl)amino)carbonyl)amino)phenyl)-1,2-benzisoxazole-4-carboxamide X=1-chloro-4-isocyanatobenzene. $^1$H NMR (500 MHz, DMSO-D$_2$O) δ 7.31-7.36 (m, 2H) 7.44-7.52 (m, 4H) 7.63-7.78 (m, 5H).

EXAMPLE 48

3-amino-N-(4-((((4-methoxyphenyl)amino)carbonyl)amino)phenyl)-1,2-benzisoxazole-4-carboxamide X=1-isocyanato-4-methoxybenzene. $^1$H NMR (500 MHz, DMSO-D$_2$O) δ 3.72-3.78 (m, 3H) 6.82-6.92 (m, 2H) 7.32-7.40 (m, 2H) 7.42-7.50 (m, 2H) 7.63-7.77.

EXAMPLE 49

3-amino-N-(4-(((benzylamino)carbonyl)amino)phenyl)-1,2-benzisoxazole-4-carboxamide X=(isocyanatomethyl)benzene. $^1$H NMR (500 MHz, DMSO-D$_2$O) δ 4.31 (s, 2H) 7.23-7.38 (m, 5H) 7.38-7.48 (m, 2H) 7.57-7.65 (m, 2H) 7.68-7.80 (m, 3H).

EXAMPLE 50

3-amino-N-(4-((((3-cyanophenyl)amino)carbonyl)amino)phenyl)-1,2-benzisoxazole-4-carboxamide X=3-isocyanatobenzonitrile. $^1$H NMR (500 MHz, DMSO-D$_2$O) δ 7.33-7.57 (m, 4H) 7.61-7.86 (m, 6H) 7.98 (t, J=1.83 Hz, 1H).

EXAMPLE 51

3-amino-N-(4-((((3-(methylthio)phenyl)amino)carbonyl)amino)phenyl)-1,2-benzisoxazole-4-carboxamide X=(3-isocyanatophenyl)(methyl)sulfane. $^1$H NMR (500 MHz, DMSO-D$_2$O) δ 2.46 (s, 3H) 6.89 (d, J=7.63 Hz, 1H) 7.16 (dd, J=7.93, 1.22 Hz, 1H) 7.19-7.36 (m, 1H) 7.40-7.58 (m, 4H) 7.64-7.80 (m, 5H).

EXAMPLE 52

3-amino-N-(4-((((4-(methylthio)phenyl)amino)carbonyl)amino)phenyl)-1,2-benzisoxazole-4-carboxamide X=(4-isocyanatophenyl)(methyl)sulfane. $^1$H NMR (500 MHz, DMSO-D$_2$O) δ 2.38 (s, 3H) 7.49 (d, J=8.85 Hz, 2H) 7.59-7.93 (m, 9H).

EXAMPLE 53

3-amino-N-(4-((((3-chloro-4-fluorophenyl)amino)carbonyl)amino)phenyl)-1,2-benzisoxazole-4-carboxamide X=2-chloro-1-fluoro-4-isocyanatobenzene. $^1$H NMR (500 MHz, DMSO-D$_2$O) δ 7.28-7.37 (m, 2H) 7.44-7.50 (m, 2H) 7.66-7.77 (m, 5H) 7.79 (dd, J=6.87, 2.29 Hz, 1H).

EXAMPLE 54

3-amino-N-(3-(((((4-fluorophenyl)amino)carbonyl)amino)methyl)phenyl)-1H-indazole-4-carboxamide

EXAMPLE 54A

The title compound was prepared by substituting 4-iodo-1H-indazol-3-amine (prepared as described in PCT application PCT/US2004/016166, published as WO2004/113304) for EXAMPLE 1A in EXAMPLE 1B.

EXAMPLE 54B

The title compound was prepared by substituting EXAMPLE 54A for EXAMPLE 1B in EXAMPLES 5A-B.

EXAMPLE 54C 3-amino-N-(3-(((((4-fluorophenyl)amino)carbonyl)amino)methyl)phenyl)-1H-indazole-4-carboxamide The title compound was prepared by substituting EXAMPLE 54B and 1-fluoro-4-isocyanatobenzene for EXAMPLE 5B and 1-isocyanato-4-methylbenzene, respectively, in EXAMPLE 5C. $^1$H NMR (500 MHz, DMSO-d$_6$) δ 4.32 (d, J=5.49 Hz, 2H) 6.66 (t, J=5.95 Hz, 1H) 7.02-7.11 (m, 3H) 7.34 (t, J=7.78 Hz, 1H) 7.39-7.47 (m, 3H) 7.52 (d, J=7.02 Hz, 1H) 7.59 (d, J=8.24 Hz, 1H) 7.67 (d, J=7.93 Hz, 1H) 7.75 (s, 1H) 8.64 (s, 1H) 10.68 (s, 1H).

EXAMPLE 55

3-amino-N-(3-(((((3-chlorophenyl)amino)carbonyl)amino)methyl)phenyl)-1H-indazole-4-carboxamide The title compound was prepared by substituting EXAMPLE 54B and 1-chloro-3-isocyanatobenzene for EXAMPLE 5B and 1-isocyanato-4-methylbenzene, respectively, in EXAMPLE 5C. $^1$H NMR (300 MHz, DMSO-d$_6$) δ 4.32 (d, J=5.76 Hz, 2H) 6.75 (t, J=5.93 Hz, 1H) 6.91-6.96 (m, 1H) 7.08 (d, J=8.14 Hz, 1H) 7.20-7.25 (m, 2H) 7.30-7.35 (m, 1H) 7.42 (d, J=8.14 Hz, 1H) 7.45-7.51 (m, 1H) 7.56 (d, J=8.14 Hz, 1H) 7.65-7.72 (m, 2H) 7.75 (s, 1H) 8.81 (s, 1H) 10.65 (s, 1H).

EXAMPLE 56

3-amino-N-(3-(((((4-(trifluoromethoxy)phenyl) amino)carbonyl)amino)methyl)phenyl)-1H-indazole-4-carboxamide The title compound was prepared by substituting EXAMPLE 54B and 1-isocyanato-4-trifluoromethoxybenzene for EXAMPLE 5B and 1-isocyanato-4-methylbenzene, respectively, in EXAMPLE 5C. $^1$H NMR (300 MHz, DMSO-d$_6$) δ 4.32 (d, J=5.95 Hz, 2H) 6.72 (t, J=5.95 Hz, 1H) 7.08 (d, J=7.93 Hz, 1H) 7.22 (d, J=8.33 Hz, 2H) 7.34 (t, J=7.73 Hz, 1H) 7.40 (d, J=7.93 Hz, 1H) 7.42-7.47 (m, 1H) 7.48-7.55 (m, 3H) 7.66 (d, J=9.12 Hz, 1H) 7.76 (s, 1H) 8.81 (s, 1H) 10.64 (s, 1H).

EXAMPLE 57

3-amino-N-(3-(((((3-methylphenyl)amino)carbonyl) amino)methyl)phenyl)-1H-indazole-4-carboxamide The title compound was prepared by substituting EXAMPLE 54B and 1-isocyanato-3-methylbenzene for EXAMPLE 5B and 1-isocyanato-4-methylbenzene, respectively, in EXAMPLE 5C. $^1$H NMR (300 MHz, DMSO-d$_6$) δ 2.24 (s, 3H) 4.31 (d, J=5.76 Hz, 2H) 6.62 (t, J=5.93 Hz, 1H) 6.71 (d, J=6.78 Hz, 1H) 7.05-7.13 (m, 2H) 7.15-7.22 (m, 1H) 7.25 (s, 1H) 7.34 (t, J=7.80 Hz, 1H) 7.38-7.46 (m, 1H) 7.47-7.52 (m, 1H) 7.57 (d, J=8.48 Hz, 1H) 7.67 (d, J=8.81 Hz, 1H) 7.75 (s, 1H) 8.48 (s, 1H) 10.67 (s, 1H).

EXAMPLE 58

3-amino-N-(3-(((((4-(trifluoromethyl)phenyl)amino) carbonyl)amino)methyl)phenyl)-1H-indazole-4-carboxamide The title compound was prepared by substituting EXAMPLE 54B and 1-isocyanato-4-trifluoromethylbenzene for EXAMPLE 5B and 1-isocyanato-4-methylbenzene, respectively, in EXAMPLE 5C. $^1$H NMR (300 MHz, DMSO-d$_6$) δ 4.34 (d, J=5.95 Hz, 2H) 6.82 (t, J=5.95 Hz, 1H) 7.09 (d, J=7.54 Hz, 1H) 7.34 (t, J=7.73 Hz, 1H) 7.38-7.45 (m, 1H) 7.46-7.52 (m, 1H) 7.53-7.70 (m, 6H) 7.76 (s, 1H) 9.04 (s, 1H) 10.66 (s, 1H).

EXAMPLE 59

3-amino-N-(3-(((((3-(trifluoromethyl)phenyl)amino) carbonyl)amino)methyl)phenyl)-1H-indazole-4-carboxamide The title compound was prepared by substituting EXAMPLE 54B and 1-isocyanato-3-trifluoromethylbenzene for EXAMPLE 5B and 1-isocyanato-4-methylbenzene, respectively, in EXAMPLE 5C. $^1$H NMR (300 MHz, DMSO-d$_6$) δ 4.33 (d, J=5.55 Hz, 2H) 6.81 (t, J=5.95 Hz, 1H) 7.09 (d, J=7.93 Hz, 1H) 7.23 (d, J=7.54 Hz, 1H) 7.31-7.35 (m, 1H) 7.36-7.59 (m, 5H) 7.68 (d, J=9.12 Hz, 1H) 7.75 (s, 1H) 8.00 (s, 1H) 8.99 (s, 1H) 10.66 (s, 1H)

EXAMPLE 60

3-amino-N-(3-(((((3-fluorophenyl)amino)carbonyl) amino)methyl)phenyl)-1H-indazole-4-carboxamide The title compound was prepared by substituting EXAMPLE 54B and 1-fluoro-3-isocyanatobenzene for EXAMPLE 5B and 1-isocyanato-4-methylbenzene, respectively, in EXAMPLE 5C. $^1$H NMR (300 MHz, DMSO-d$_6$) δ 4.32 (d, J=5.95 Hz, 2H) 6.65-6.77 (m, 2H) 7.02-7.11 (m, 2H) 7.19-7.29 (m, 1H) 7.34 (t, J=7.93 Hz, 1H) 7.38-7.52 (m, 3H) 7.57 (d, J=8.33 Hz, 1H) 7.67 (d, J=7.93 Hz, 1H) 7.75 (s, 1H) 8.84 (s, 1H) 10.66 (s, 1H).

EXAMPLE 61

3-amino-N-(4-((anilinocarbonyl)amino)phenyl)-1H-indazole-4-carboxamide

The title compound was prepared by substituting EXAMPLE 54B and isocyanatobenzene for EXAMPLE 1B and 1-fluoro-3-isocyanatobenzene, respectively, in EXAMPLE 23A and EXAMPLE 23B. $^1$H NMR (300 MHz, DMSO-d$_6$) δ 5.35 (s, 2H) 6.96 (t, J=7.29 Hz, 1H) 7.24-7.37 (m, 4H) 7.42-7.49 (m, 5H) 7.70 (d, J=8.82 Hz, 2H) 8.62 (s, 1H) 8.64 (s, 1H) 10.51 (s, 1H) 11.81 (s, 1H).

EXAMPLE 62

3-amino-N-(4-((((3-fluorophenyl)amino)carbonyl) amino)phenyl)-1H-indazole-4-carboxamide The title compound was prepared by substituting EXAMPLE 54B for EXAMPLE 1B in EXAMPLE 23B. $^1$H NMR (300 MHz, DMSO-d$_6$) δ 5.35 (s, 2H) 6.73-6.82 (m, 1H) 7.12 (d, J=9.16 Hz, 1H) 7.25-7.39 (m, 3H) 7.42-7.53 (m, 4H) 7.71 (d, J=9.16 Hz, 2H) 8.72 (s, 1H) 8.86 (s, 1H) 10.52 (s, 1H) 11.82 (s, 1H).

EXAMPLE 63

3-amino-N-(3-(((((3-fluorophenyl)amino)carbonyl) amino)methyl)phenyl)-7-(3-hydroxypropoxy)-1,2-benzisoxazole-4-carboxamide

EXAMPLE 63A

A mixture of 2-fluoro-3-hydroxy-6-iodobenzonitrile (650 mg), (prepared as described in J. Med. Chem. 2007, 50, 1584), 3-iodopropan-1-ol (261 µL) and Cs$_2$CO$_3$ (886 mg) in DMF (10 mL) at 60° C. was stirred for 4 hours, cooled to room temperature, poured into water and extracted with ethyl acetate. The extract was dried, filtered and concentrated, and the concentrate was flash chromatographed on silica gel with 0-4% methanol/dichloromethane. $^1$H NMR (300 MHz, DMSO-d$_6$) δ 1.77-1.95 (m, 2H) 3.54 (q, J=6.10 Hz, 2H) 4.17 (t, J=6.44 Hz, 2H) 4.59 (t, J=5.26 Hz, 1H) 7.37 (t, J=8.81 Hz, 1H) 7.77 (dd, J=8.81, 1.36 Hz, 1H).

EXAMPLE 63B

A mixture of N-hydroxyacetamide (421 mg) and potassium tert-butoxide (0.63 g) in DMF (15 mL) at room temperature was stirred for 30 minutes, treated with EXAMPLE 63A (0.6 g), stirred overnight, diluted with water and extracted with ethyl acetate. The extract was dried, filtered and concentrated, and the concentrate was flash chromatographed on silica gel with 0-5% methanol/dichloromethane.

EXAMPLE 63C

The title compound was prepared by substituting EXAMPLE 63B for EXAMPLE 1A in EXAMPLE 1B.

EXAMPLE 63D 3-amino-N-(3-(((((3-fluorophenyl)amino)carbonyl)amino)methyl)phenyl)-7-(3-hydroxypropoxy)-1,2-benzisoxazole-4-carboxamide The title compound was prepared by substituting EXAMPLE 63C for EXAMPLE 1B in EXAMPLE 1D. $^1$H NMR (400 MHz, DMSO-$d_6$) δ 1.77-2.09 (m, 2H) 3.60 (q, J=5.73 Hz, 2H) 4.31 (t, J=5.37 Hz, 4H) 6.43 (s, 2H) 6.58-6.82 (m, 2H) 6.96-7.14 (m, 2H) 7.14-7.38 (m, 3H) 7.38-7.54 (m, 1H) 7.56-7.84 (m, 3H) 8.81 (s, 1H) 10.59 (s, 1H).

EXAMPLE 64

3-amino-N-(3-(((anilinocarbonyl)amino)methyl)phenyl)-7-(3-hydroxypropoxy)-1,2-benzisoxazole-4-carboxamide The title compound was prepared by substituting isocyanatobenzene for 1-fluoro-3-isocyanatobenzene and EXAMPLE 63C for EXAMPLE 1B in EXAMPLE 1C and EXAMPLE 1D, respectively. $^1$H NMR (400 MHz, DMSO-$d_6$) δ 1.77-2.03 (m, 2H) 3.47-3.68 (m, 2H) 4.20-4.40 (m, 4H) 4.60 (t, J=5.06 Hz, 1H) 6.44 (s, 2H) 6.61 (t, J=5.98 Hz, 1H) 6.89 (t, J=7.36 Hz, 1H) 7.09 (d, J=7.67 Hz, 1H) 7.16-7.28 (m, 3H) 7.28-7.48 (m, 3H) 7.57-7.91 (m, 3H) 8.54 (s, 1H) 10.59 (s, 1H).

EXAMPLE 65

3-amino-N-(3-(1-((((3-fluorophenyl)amino)carbonyl)amino)ethyl)phenyl)-1,2-benzisoxazole-4-carboxamide The title compound was prepared by substituting tert-butyl 3-(1-aminoethyl)phenylcarbamate and 1-fluoro-3-isocyanatobenzene for tert-butyl 3-aminobenzylcarbamate and 1-isocyanato-4-methylbenzene, respectively, in EXAMPLES 5A-C. $^1$H NMR (300 MHz, DMSO-$d_6$) δ 1.40 (1H) 1.42 (d, J=6.74 Hz, 3H) 2.08 (none, 1H) 4.81 (q, J=7.14 Hz, 1H) 6.32 (s, 2H) 6.58-6.78 (m, 2H) 6.99 (d, J=8.33 Hz, 1H) 7.11-7.29 (m, 2H) 7.31-7.49 (m, 2H) 7.56-7.89 (m, 5H) 8.63 (s, 1H) 10.78 (s, 1H).

EXAMPLE 66

3-amino-N-(4-((anilinocarbonyl)amino)benzyl)-1,2-benzisoxazole-4-carboxamide

The title compound was prepared by substituting 1-(4-(aminomethyl)phenyl)-3-phenylurea for EXAMPLE 1C in EXAMPLE 1D. $^1$H NMR (500 MHz, DMSO-$d_6$) δ 4.51 (d, J=6.10 Hz, 2H) 6.22-6.75 (m, 2H) 6.96 (t, J=7.48 Hz, 2H) 7.15-7.33 (m, 3H) 7.32-7.54 (m, 4H) 7.54-7.77 (m, 3H) 8.62 (s, 1H) 8.70 (s, 1H) 9.55 (t, J=5.95 Hz, 1H).

EXAMPLE 67

3-amino-N-(3-(((anilinocarbonyl)amino)methyl)phenyl)-1H-indazole-4-carboxamide

The title compound was prepared by substituting EXAMPLE 54B and isocyanatobenzene for EXAMPLE 5B and 1-isocyanato-4-methylbenzene, respectively, in EXAMPLE 5C. $^1$H NMR (300 MHz, DMSO-$d_6$) δ 4.32 (d, J=5.55 Hz, 2H) 6.63 (t, J=5.95 Hz, 1H) 6.89 (t, J=7.34 Hz, 1H) 7.08 (d, J=7.93 Hz, 1H) 7.17-7.27 (m, 2H) 7.29-7.48 (m, 5H) 7.53 (d, J=8.33 Hz, 1H) 7.67 (d, J=7.93 Hz, 1H) 7.76 (s, 1H) 8.56 (s, 1H) 10.65 (s, 1H).

EXAMPLE 68

3-amino-N-(3-(((((4-chlorophenyl)amino)carbonyl)amino)methyl)phenyl)-1H-indazole-4-carboxamide The title compound was prepared by substituting EXAMPLE 54B and 1-chloro-4-isocyanatobenzene for EXAMPLE 5B and 1-isocyanato-4-methylbenzene, respectively, in EXAMPLE 5C. $^1$H NMR (300 MHz, DMSO-$d_6$) δ 4.32 (d, J=5.76 Hz, 2H) 6.69 (t, J=5.76 Hz, 1H) 7.08 (d, J=7.80 Hz, 1H) 7.22-7.29 (m, 2H) 7.34 (t, J=7.97 Hz, 1H) 7.37-7.51 (m, 4H) 7.56 (d, J=8.14 Hz, 1H) 7.67 (d, J=7.80 Hz, 1H) 7.75 (s, 1H) 8.73 (s, 1H) 10.65 (s, 1H).

EXAMPLE 69

3-amino-N-(3-(((((4-chloro-2-fluorophenyl)amino)carbonyl)amino)methyl)phenyl)-1H-indazole-4-carboxamide The title compound was prepared by substituting EXAMPLE 54B and 1-chloro-3-fluoro-4-isocyanatobenzene for EXAMPLE 5B and 1-isocyanato-4-methylbenzene, respectively, in EXAMPLE 5C. $^1$H NMR (300 MHz, DMSO-$d_6$) δ 4.34 (d, J=5.95 Hz, 2H) 7.05-7.21 (m, 3H) 7.32-7.48 (m, 3H) 7.49-7.55 (m, 1H) 7.59 (d, J=7.93 Hz, 1H) 7.68 (d, J=9.12 Hz, 1H) 7.75 (s, 2H) 8.18 (t, J=8.92 Hz, 1H) 8.52 (d, J=2.38 Hz, 1H) 10.68 (s, 1H).

EXAMPLE 70

3-amino-N-(3-(((((3-fluoro-4-methylphenyl)amino)carbonyl)amino)methyl)phenyl)-1H-indazole-4-carboxamide The title compound was prepared by substituting EXAMPLE 54B and 2-fluoro-4-isocyanato-1-methylbenzene for EXAMPLE 5B and 1-isocyanato-4-methylbenzene, respectively, in EXAMPLE 5C. $^1$H NMR (300 MHz, DMSO-$d_6$) δ 2.13 (d, J=1.36 Hz, 3H) 4.31 (d, J=5.76 Hz, 2H) 6.67 (t, J=5.93 Hz, 1H) 6.95 (dd, J=8.14, 2.03 Hz, 1H) 7.09 (t, J=8.65 Hz, 2H) 7.30-7.45 (m, 4H) 7.52 (d, J=8.14 Hz, 1H) 7.66 (d, J=8.14 Hz, 1H) 7.75 (s, 1H) 8.68 (s, 1H) 10.63 (s, 1H).

EXAMPLE 71

3-amino-N-(3-(((((2-fluoro-5-methylphenyl)amino)carbonyl)amino)methyl)phenyl)-1H-indazole-4-carboxamide The title compound was prepared by substituting EXAMPLE 54B and 1-fluoro-2-isocyanato-4-methylbenzene for EXAMPLE 5B and 1-isocyanato-4-methylbenzene, respectively, in EXAMPLE 5C. $^1$H NMR (300 MHz, DMSO-$d_6$) δ 2.23 (s, 3H) 4.33 (d, J=5.76 Hz, 2H) 6.67-6.76 (m, 1H) 6.99-7.14 (m, 3H) 7.35 (t, J=7.80 Hz, 1H) 7.39-7.47 (m, 1H) 7.48-7.53 (m, 1H) 7.57 (d, J=8.48 Hz, 1H) 7.68 (d, J=7.80 Hz, 1H) 7.75 (s, 1H) 7.98 (dd, J=7.80, 2.03 Hz, 1H) 8.31 (d, J=2.71 Hz, 1H) 10.67 (s, 1H).

EXAMPLE 72

3-amino-N-(3-(((((2-fluoro-5-(trifluoromethyl)phenyl)amino)carbonyl)amino)methyl)phenyl)-1H-indazole-4-carboxamide The title compound was prepared by substituting EXAMPLE 54B and 1-fluoro-2-isocyanato-4-(trifluoromethyl)benzene for EXAMPLE 5B and 1-isocyanato-4-methylbenzene, respectively, in EXAMPLE 5C. $^1$H NMR (300 MHz, DMSO-$d_6$) δ 4.35 (d, J=5.76 Hz, 2H) 7.09 (d, J=7.46 Hz, 1H) 7.24 (t, J=5.93 Hz, 1H) 7.27-7.53 (m, 6H) 7.69 (d, J=8.14 Hz, 1H) 7.77 (s, 1H) 8.63 (dd, J=7.46, 2.03 Hz, 1H) 8.77 (d, J=2.71 Hz, 1H) 10.63 (s, 1H).

EXAMPLE 73

3-amino-N-(3-(((((3,5-difluorophenyl)amino)carbonyl)amino)methyl)phenyl)-1H-indazole-4-carboxamide The title compound was prepared by substituting EXAMPLE 54B and 1,3-difluoro-5-isocyanatobenzene for EXAMPLE 5B and 1-isocyanato-4-methylbenzene, respectively, in EXAMPLE 5C. $^1$H NMR (300 MHz, DMSO-$d_6$) δ 4.32 (d, J=5.76 Hz, 2H) 6.69 (tt, J=9.32, 2.37 Hz, 1H) 6.87 (t, J=5.93 Hz, 1H) 7.05-7.18 (m, 3H) 7.30-7.50 (m, 3H) 7.55 (d, J=7.80 Hz, 1H) 7.67 (d, J=9.15 Hz, 1H) 7.75 (s, 1H) 9.05 (s, 1H) 10.66 (s, 1H).

EXAMPLE 74

3-amino-N-(3-(((((3,4-difluorophenyl)amino)carbonyl)amino)methyl)phenyl)-1H-indazole-4-carboxamide The title compound was prepared by substituting EXAMPLE 54B and 1,2-difluoro-4-isocyanatobenzene for EXAMPLE 5B and 1-isocyanato-4-methylbenzene, respectively, in EXAMPLE 5C. $^1$H NMR (300 MHz, DMSO-$d_6$) δ 4.31 (d, J=5.76 Hz, 2H) 6.75 (t, J=5.93 Hz, 1H) 7.01-7.10 (m, 2H) 7.22-7.50 (m, 4H) 7.55 (d, J=8.14 Hz, 1H) 7.60-7.70 (m, 2H) 7.75 (s, 1H) 8.84 (s, 1H) 10.65 (s, 1H).

EXAMPLE 75

3-amino-N-(3-(((((3-fluoro-4-methylphenyl)amino)carbonyl)amino)methyl)phenyl)-1,2-benzisoxazole-4-carboxamide The title compound was prepared by substituting 2-fluoro-4-isocyanato-1-methylbenzene for 1-isocyanato-4-methylbenzene in EXAMPLE 5C. $^1$H NMR (300 MHz, DMSO-$d_6$) δ 2.13 (s, 3H) 4.31 (d, J=5.95 Hz, 2H) 6.32 (s, 2H) 6.67 (t, J=5.95 Hz, 1H) 6.95 (dd, J=8.33, 1.98 Hz, 1H) 7.00-7.21 (m, 2H) 7.25-7.50 (m, 2H) 7.54-7.87 (m, 5H) 8.68 (s, 1H) 10.78 (s, 1H).

EXAMPLE 76

3-amino-N-(3-(((((4-chlorophenyl)amino)carbonyl)amino)methyl)phenyl)-1,2-benzisoxazole-4-carboxamide The title compound was prepared by substituting 1-chloro-4-isocyanatobenzene for 1-isocyanato-4-methylbenzene in EXAMPLE 5C. $^1$H NMR (300 MHz, DMSO-$d_6$) δ 4.32 (d, J=5.76 Hz, 2H) 6.31 (s, 2H) 6.69 (t, J=5.93 Hz, 1H) 7.11 (d, J=7.80 Hz, 1H) 7.21-7.53 (m, 5H) 7.57-7.89 (m, 5H) 8.72 (s, 1H) 10.78 (s, 1H).

EXAMPLE 77

3-amino-N-(3-(((((3-bromophenyl)amino)carbonyl)amino)methyl)phenyl)-1,2-benzisoxazole-4-carboxamide The title compound was prepared by substituting 1-bromo-3-isocyanatobenzene for 1-isocyanato-4-methylbenzene in EXAMPLE 5C. $^1$H NMR (300 MHz, DMSO-$d_6$) δ 4.32 (d, J=5.83 Hz, 2H) 6.33 (s, 2H) 6.74 (t, J=5.83 Hz, 1H) 6.96-7.45 (m, 5H) 7.55-7.79 (m, 5H) 7.84 (t, J=1.99 Hz, 1H) 8.79 (s, 1H) 10.77 (s, 1H).

EXAMPLE 78

3-amino-N-(3-(((((3-fluorophenyl)amino)carbonyl)amino)methyl)phenyl)-7-(2-morpholin-4-ylethoxy)-1,2-benzisoxazole-4-carboxamide

EXAMPLE 78A 3-amino-7-(2-morpholinoethoxy)benzo(d)isoxazole-4-carboxylic acid

The title compound was prepared by substituting 4-iodo-7-(2-morpholinoethoxy)benzo(d)isoxazol-3-amine (J. Med. Chem. 2008, 51, 1231-1241) for EXAMPLE 1A in EXAMPLE 1B. MS (ESI(+)) m/e 308 (M+H)$^+$.

EXAMPLE 78B 3-amino-N-(3-(((((3-fluorophenyl)amino)carbonyl)amino)methyl)phenyl)-7-(2-morpholin-4-ylethoxy)-1,2-benzisoxazole-4-carboxamide The title compound was prepared by substituting EXAMPLE 78A for EXAMPLE 1B in EXAMPLE 1D. $^1$H NMR (500 MHz, DMSO-$d_6$) □ ppm 2.51 (s, 4 H) 2.79 (t, J=5.49 Hz, 2 H) 3.54-3.63 (m, 4 H) 4.32 (d, J=5.80 Hz, 2 H) 4.36 (t, J=5.49 Hz, 2 H) 6.45 (s, 2 H) 6.64-6.77 (m, 2 H) 7.05 (d, J=8.24 Hz, 1 H) 7.09 (d, J=7.32 Hz, 1 H) 7.20-7.28 (m, 2 H) 7.34 (t, J=7.78 Hz, 1 H) 7.47 (d, J=12.51 Hz, 1 H) 7.63 (d, J=7.93 Hz, 1 H) 7.70 (s, 1 H) 7.75 (d, J=8.24 Hz, 1 H) 8.84 (s, 1 H) 10.62 (s, 1 H). MS (ESI(+)) m/e 549 (M+H)$^+$.

EXAMPLE 79

3-amino-N-(3-(((anilinocarbonyl)amino)methyl)phenyl)-7-(2-morpholin-4-ylethoxy)-1,2-benzisoxazole-4-carboxamide The title compound was prepared by substituting isocyanatobenzene for 1-fluoro-3-isocyanatobenzene and EXAMPLE 78A for EXAMPLE 1B in EXAMPLE 1C and 1D, respectively. ¹H NMR (500 MHz, DMSO-d₆) ☐ ppm 2.51 (d, J=1.53 Hz, 4 H) 2.79 (t, J=5.49 Hz, 2 H) 3.51-3.63 (m, 4 H) 4.32 (d, J=5.80 Hz, 2 H) 4.37 (t, J=5.65 Hz, 2 H) 6.46 (s, 2 H) 6.63 (t, J=5.95 Hz, 1 H) 6.89 (t, J=7.32 Hz, 1 H) 7.09 (d, J=7.63 Hz, 1 H) 7.17-7.27 (m, 3 H) 7.34 (t, J=7.93 Hz, 1 H) 7.41 (d, J=7.63 Hz, 2 H) 7.63 (d, J=7.93 Hz, 1 H) 7.71 (s, 1 H) 7.76 (d, J=8.24 Hz, 1 H) 8.56 (s, 1 H) 10.62 (s, 1 H). MS (ESI(+)) m/e 531 (M+H)⁺.

EXAMPLE 80

3-amino-7-(2-morpholin-4-ylethoxy)-N-(3-(((((4-(trifluoromethyl)phenyl)amino)carbonyl)amino)methyl)phenyl)-1,2-benzisoxazole-4-carboxamide The title compound was prepared by substituting 1-isocyanato-4-(trifluoromethyl)benzene for 1-fluoro-3-isocyanatobenzene and EXAMPLE 78A for EXAMPLE 1B in EXAMPLE 1C and 1D, respectively. ¹H NMR (500 MHz, DMSO-d₆) ☐ ppm 2.50 (s, 4 H) 2.79 (s, 2 H) 3.59 (s, 4 H) 4.29-4.43 (m, 4 H) 6.46 (s, 2 H) 6.82 (t, J=5.65 Hz, 1 H) 7.10 (d, J=7.32 Hz, 1 H) 7.26 (d, J=8.24 Hz, 1 H) 7.34 (t, J=7.78 Hz, 1 H) 7.51-7.66 (m, 5 H) 7.72 (s, 1 H) 7.76 (d, J=8.24 Hz, 1 H) 9.04 (s, 1 H) 10.62 (s, 1 H). MS (ESI(+)) m/e 599 (M+H)⁺.

EXAMPLE 81

3-amino-N-(3-(((((3-fluorophenyl)amino)carbonyl)amino)methyl)phenyl)-7-methoxy-1,2-benzisoxazole-4-carboxamide

EXAMPLE 81A 3-amino-7-methoxybenzo(d)isoxazole-4-carboxylic acid

The title compound was prepared by substituting 4-iodo-7-methoxybenzo(d)isoxazol-3-amine (J. Med. Chem. 2008, 51, 1231-1241) for EXAMPLE 1A in EXAMPLE 1B. MS (ESI(+)) m/e 209 (M+H)⁺.

EXAMPLE 81B 3-amino-N-(3-(((((3-fluorophenyl)amino)carbonyl)amino)methyl)phenyl)-7-methoxy-1,2-benzisoxazole-4-carboxamide The title compound was prepared by substituting EXAMPLE 81A for EXAMPLE 1B in EXAMPLE 1D. ¹H NMR (400 MHz, DMSO-d₆) ☐ ppm 4.02 (s, 3 H) 4.32 (d, J=6.14 Hz, 2 H) 6.43 (s, 2 H) 6.62-6.78 (m, 2 H) 7.07 (dd, J=16.11, 8.44 Hz, 2 H) 7.18-7.27 (m, 2 H) 7.34 (t, J=7.83 Hz, 1 H) 7.42-7.51 (m, 1 H) 7.63 (d, J=8.29 Hz, 1 H) 7.70 (s, 1 H) 7.77 (d, J=8.29 Hz, 1 H) 8.82 (s, 1 H) 10.60 (s, 1 H). MS (ESI(+)) m/e 450 (M+H)⁺.

EXAMPLE 82

3-amino-N-(3-(((anilinocarbonyl)amino)methyl)phenyl)-7-methoxy-1,2-benzisoxazole-4-carboxamide The title compound was prepared by substituting isocyanatobenzene for 1-fluoro-3-isocyanatobenzene and EXAMPLE 81A for EXAMPLE 1B in EXAMPLE 1C and 1D, respectively. ¹H NMR (500 MHz, DMSO-d₆) ☐ ppm 4.01 (s, 3 H) 4.32 (d, J=5.80 Hz, 2 H) 6.29-6.57 (m, 2 H) 6.63 (t, J=5.95 Hz, 1 H) 6.89 (t, J=7.32 Hz, 1 H) 7.09 (d, J=7.63 Hz, 1 H) 7.22 (t, J=7.78 Hz, 3 H) 7.34 (t, J=7.78 Hz, 1 H) 7.41 (d, J=7.63 Hz, 2 H) 7.63 (d, J=7.93 Hz, 1 H) 7.71 (s, 1 H) 7.77 (d, J=8.24 Hz, 1 H) 8.56 (s, 1 H) 10.62 (s, 1 H). MS (ESI(+)) m/e 432 (M+H)⁺.

EXAMPLE 83

3-amino-7-methoxy-N-(3-(((((4-(trifluoromethyl)phenyl)amino)carbonyl)amino)methyl)phenyl)-1,2-benzisoxazole-4-carboxamide The title compound was prepared by substituting 1-isocyanato-4-(trifluoromethyl)benzene for 1-fluoro-3-isocyanatobenzene and EXAMPLE 81A for EXAMPLE 1B in EXAMPLE 1C and 1D, respectively. ¹H NMR (500 MHz, DMSO-d₆) ☐ ppm 4.01 (s, 3 H) 4.34 (d, J=5.80 Hz, 2 H) 6.30-6.60 (m, 2 H) 6.82 (t, J=5.95 Hz, 1 H) 7.10 (d, J=7.93 Hz, 1 H) 7.23 (d, J=8.24 Hz, 1 H) 7.34 (t, J=7.78 Hz, 1 H) 7.52-7.67 (m, 5 H) 7.72 (s, 1 H) 7.77 (d, J=8.24 Hz, 1 H) 9.04 (s, 1 H) 10.63 (s, 1 H). MS (ESI(+)) m/e 500 (M+H)⁺.

EXAMPLE 84

3-amino-N-(3-(((((4-chloro-2-fluorophenyl)amino)carbonyl)amino)methyl)phenyl)-1,2-benzisoxazole-4-carboxamide The title compound was prepared by substituting 4-chloro-2-fluoro-1-isocyanatobenzene for 1-fluoro-3-isocyanatobenzene in EXAMPLES 1C-1D. ¹H NMR (500 MHz, DMSO-d₆) ☐ ppm 4.34 (d, J=5.76 Hz, 2 H) 6.31 (s, 2 H) 6.99-7.25 (m, 3 H) 7.28-7.50 (m, 2 H) 7.56-7.84 (m, 5 H) 8.17 (t, J=8.82 Hz, 1 H) 8.51 (d, J=2.71 Hz, 1 H) 10.78 (s, 1 H). MS (ESI(+)) m/e 454 (M+H)⁺.

EXAMPLE 85

3-amino-N-(3-(((((4-chloro-2-fluorophenyl)amino)carbonyl)amino)methyl)phenyl)-7-methoxy-1,2-benzisoxazole-4-carboxamide The title compound was prepared by substituting 4-chloro-2-fluoro-1-isocyanatobenzene for 1-fluoro-3-isocyanatobenzene and EXAMPLE 81A for EXAMPLE 1B in EXAMPLE 1C and 1D, respectively. ¹H NMR (500 MHz, DMSO-d₆) ☐ ppm 4.02 (s, 3 H) 4.33 (d, J=5.55 Hz, 2 H) 6.45 (s, 2 H) 7.01-7.26 (m, 4 H) 7.29-7.46 (m, 2 H) 7.64 (d, J=8.33 Hz, 1 H) 7.71 (s, 1 H) 7.77 (d, J=8.33 Hz, 1 H) 8.18 (t, J=8.92 Hz, 1 H) 8.51 (d, J=2.38 Hz, 1 H) 10.62 (s, 1 H)
MS (ESI(+)) m/e 484 (M+H)⁺.

EXAMPLE 86

3-amino-7-(3-hydroxypropoxy)-N-(3-(((((4-(trifluoromethyl)phenyl)amino)carbonyl)amino)methyl)phenyl)-1,2-benzisoxazole-4-carboxamide The title compound was prepared by substituting 1-isocyanato-4-(trifluoromethyl)benzene for 1-fluoro-3-isocyanatobenzene and EXAMPLE 63C for EXAMPLE 1B in EXAMPLE 1C and 1D, respectively. ¹H NMR (500 MHz, DMSO-d₆) ☐ ppm 1.76-2.06 (m, 2 H) 3.60 (t, J=6.10 Hz, 2 H) 4.22-4.40 (m, 4 H) 4.59 (s, 1 H) 6.45 (s, 2 H) 6.80 (t, J=5.93 Hz, 1 H) 7.03-7.14 (m, 1 H) 7.23 (d, J=8.48 Hz, 1 H) 7.34 (t, J=7.80 Hz, 1 H) 7.52-7.68 (m, 5 H) 7.68-7.83 (m, 2 H) 9.02 (s, 1 H) 10.60 (s, 1 H). MS (ESI(+)) m/e 544 (M+H)+.

EXAMPLE 87

3-amino-N-(3-(((((3,4-difluorophenyl)amino)carbonyl)amino)methyl)phenyl)-7-methoxy-1,2-benzisoxazole-4-carboxamide The title compound was prepared by substituting 1,2-difluoro-4-isocyanatobenzene for 1-fluoro-3-isocyanatobenzene and EXAMPLE 81A for EXAMPLE 1B in EXAMPLE 1C and 1D, respectively. $^1$H NMR (500 MHz, DMSO-d$_6$) □ ppm 4.02 (s, 3 H) 4.31 (d, J=5.76 Hz, 2 H) 6.44 (s, 2 H) 6.74 (t, J=5.93 Hz, 1 H) 6.96-7.14 (m, 2 H) 7.17-7.41 (m, 3 H) 7.55-7.72 (m, 3 H) 7.77 (d, J=8.14 Hz, 1 H) 8.82 (s, 1 H) 10.60 (s, 1 H). MS (ESI(+)) m/e 468 (M+H)+.

EXAMPLE 88

3-amino-N-(3-(((((pyridin-3-ylamino)carbonyl)amino)methyl)phenyl)-1,2-benzisoxazole-4-carboxamide The title compound was prepared by substituting 3-isocyanatopyridine for 1-fluoro-3-isocyanatobenzene in EXAMPLES 1C-1D. $^1$H NMR (500 MHz, DMSO-d$_6$) □ ppm 4.34 (d, J=5.76 Hz, 2 H) 6.32 (s, 2 H) 6.88 (t, J=5.93 Hz, 1 H) 7.12 (d, J=7.12 Hz, 1 H) 7.27-7.45 (m, 2 H) 7.55-7.84 (m, 5 H) 7.97 (d, J=9.16 Hz, 1 H) 8.17 (d, J=4.07 Hz, 1 H) 8.64 (s, 1 H) 8.91 (s, 1 H) 10.78 (s, 1 H). MS (ESI(+)) m/e 403 (M+H)+.

EXAMPLE 89

3-amino-7-methoxy-N-(3-((((pyridin-3-ylamino)carbonyl)amino)methyl)phenyl)-1,2-benzisoxazole-4-carboxamide The title compound was prepared by substituting 3-isocyanatopyridine for 1-fluoro-3-isocyanatobenzene and EXAMPLE 81A for EXAMPLE 1B in EXAMPLE 1C and 1D, respectively. $^1$H NMR (500 MHz, DMSO-d$_6$) □ ppm 4.01 (s, 3 H) 4.34 (d, J=5.76 Hz, 2 H) 6.44 (s, 2 H) 6.88 (t, J=5.76 Hz, 1 H) 7.10 (d, J=7.46 Hz, 1 H) 7.22 (d, J=8.14 Hz, 1 H) 7.28-7.44 (m, 2 H) 7.62 (d, J=8.14 Hz, 1 H) 7.67-7.82 (m, 2 H) 7.97 (d, J=8.82 Hz, 1 H) 8.18 (d, J=4.07 Hz, 1 H) 8.66 (s, 1 H) 8.92 (s, 1 H) 10.61 (s, 1 H). MS (ESI(+)) m/e 433 (M+H)+.

EXAMPLE 90

3-amino-N-(3-(((((4-chlorophenyl)amino)carbonyl)amino)methyl)phenyl)-7-(2-morpholin-4-ylethoxy)-1,2-benzisoxazole-4-carboxamide The title compound was prepared by substituting 1-chloro-4-isocyanatobenzene for 1-fluoro-3-isocyanatobenzene and EXAMPLE 78A for EXAMPLE 1B in EXAMPLE 1C and 1D, respectively. $^1$H NMR (500 MHz, DMSO-d$_6$) □ ppm 3.64 (d, J=15.47 Hz, 10 H) 4.32 (d, J=5.95 Hz, 2 H) 4.62 (s, 2 H) 6.48 (s, 2 H) 6.75 (t, J=6.15 Hz, 1 H) 7.09 (d, J=7.54 Hz, 1 H) 7.21-7.49 (m, 6 H) 7.64 (d, J=7.93 Hz, 1 H) 7.69 (s, 1 H) 7.80 (d, J=8.33 Hz, 1 H) 8.78 (s, 1 H) 10.64 (s, 1 H). MS (ESI(+)) m/e 565 (M+H)+.

EXAMPLE 91

3-amino-N-(4-((anilinocarbonyl)amino)phenyl)-7-(2-morpholin-4-ylethoxy)-1,2-benzisoxazole-4-carboxamide The title compound was prepared by substituting 1-(4-aminophenyl)-3-phenylurea for EXAMPLE 1C and EXAMPLE 78A for EXAMPLE 1B in EXAMPLE 1D. $^1$H NMR (500 MHz, DMSO-d$_6$) □ ppm 3.46-4.21 (m, 10 H) 4.62 (s, 2 H) 6.52 (s, 2 H) 6.97 (t, J=7.29 Hz, 1 H) 7.21-7.36 (m, 3 H) 7.40-7.53 (m, 4 H) 7.65 (d, J=9.16 Hz, 2 H) 7.80 (d, J=8.14 Hz, 1 H) 8.68 (s, 1 H) 8.71 (s, 1 H) 10.53 (s, 1 H)MS (ESI(+)) m/e 517 (M+H)+.

EXAMPLE 92

3-amino-N-(3-(((((4-chlorophenyl)amino)carbonyl)amino)methyl)phenyl)-7-(2-(4-methylpiperazin-1-yl)ethoxy)-1,2-benzisoxazole-4-carboxamide

EXAMPLE 92A 3-amino-7-(2-(4-methylpiperazin-1-yl)ethoxy)benzo(d)isoxazole-4-carboxylic acid The title compound was prepared by substituting 4-iodo-7-(2-(4-methylpiperazin-1-yl)ethoxy)benzo(d)isoxazol-3-amine (J. Med. Chem. 2008, 51, 1231-1241) for EXAMPLE 1A in EXAMPLE 1B. MS (ESI(+)) m/e 321 (M+H)+.

EXAMPLE 92B 3-amino-N-(3-(((((4-chlorophenyl)amino)carbonyl)amino)methyl)phenyl)-7-(2-(4-methylpiperazin-1-yl)ethoxy)-1,2-benzisoxazole-4-carboxamide The title compound was prepared by substituting 1-chloro-4-isocyanatobenzene for 1-fluoro-3-isocyanatobenzene and EXAMPLE 92A for EXAMPLE 1B in EXAMPLE 1C and 1D, respectively. $^1$H NMR (500 MHz, DMSO-d$_6$) □ ppm 2.65 (s, 3 H) 2.69-3.15 (m, 10 H) 4.31 (d, J=5.95 Hz, 2 H) 4.37 (t, J=5.16 Hz, 2 H) 6.46 (s, 2 H) 6.70 (t, J=5.95 Hz, 1 H) 7.09 (d, J=7.54 Hz, 1 H) 7.19-7.48 (m, 6 H) 7.63 (d, J=7.93 Hz, 1 H) 7.69 (s, 1 H) 7.76 (d, J=8.33 Hz, 1 H) 8.74 (s, 1 H) 10.60 (s, 1 H). MS (ESI(+)) m/e 578 (M+H)+.

EXAMPLE 93

3-amino-7-(2-(4-methylpiperazin-1-yl)ethoxy)-N-(3-(((((4-(trifluoromethyl)phenyl)amino)carbonyl)amino)methyl)phenyl)-1,2-benzisoxazole-4-carboxamide The title compound was prepared by substituting 1-isocyanato-4-(trifluoromethyl)benzene for 1-fluoro-3-isocyanatobenzene and EXAMPLE 92A for EXAMPLE 1B in EXAMPLE 1C and 1D, respectively. $^1$H NMR (500 MHz, DMSO-d$_6$) □ ppm 2.77 (s, 3 H) 2.83-3.24 (m, 10 H) 4.33 (d, J=5.95 Hz, 2 H) 4.40 (s, 2 H) 6.46 (s, 2 H) 6.85 (t, J=5.95 Hz, 1 H) 7.10 (d, J=7.93 Hz, 1 H) 7.25 (d, J=8.33 Hz, 1 H) 7.34 (t, J=7.73 Hz, 1 H) 7.53-7.69 (m, 5 H) 7.71 (s, 1 H) 7.77 (d, J=8.33 Hz, 1 H) 9.10 (s, 1 H) 10.62 (s, 1 H). MS (ESI(+)) m/e 612 (M+H)$^+$.

EXAMPLE 94

3-amino-N-(3-(((((4-methylphenyl)amino)carbonyl) amino)methyl)phenyl)-7-(2-(4-methylpiperazin-1-yl) ethoxy)-1,2-benzisoxazole-4-carboxamide The title compound was prepared by substituting 1-isocyanato-4-methylbenzene for 1-fluoro-3-isocyanatobenzene and EXAMPLE 92A for EXAMPLE 1B in EXAMPLE 1C and 1D, respectively. $^1$H NMR (500 MHz, DMSO-d$_6$) ppm 2.21 (s, 3 H) 2.66 (s, 3 H) 2.70-3.17 (m, 10 H) 4.30 (d, J=5.76 Hz, 2 H) 4.37 (t, J=5.09 Hz, 2 H) 6.46 (s, 2 H) 6.57 (t, J=5.93 Hz, 1 H) 6.97-7.14 (m, 3 H) 7.21-7.42 (m, 4 H) 7.63 (d, J=8.48 Hz, 1 H) 7.69 (s, 1 H) 7.77 (d, J=8.14 Hz, 1 H) 8.43 (s, 1 H) 10.60 (s, 1 H). MS (ESI(+)) m/e 558 (M+H)$^+$.

EXAMPLE 95

3-amino-N-(3-(((((2,4-difluorophenyl)amino)carbonyl)amino)methyl)phenyl)-7-methoxy-1,2-benzisoxazole-4-carboxamide The title compound was prepared by substituting 2,4-difluoro-1-isocyanatobenzene for 1-fluoro-3-isocyanatobenzene and EXAMPLE 81A for EXAMPLE 1B in EXAMPLE 1C and 1D, respectively. $^1$H NMR (500 MHz, DMSO-d$_6$) ppm 4.02 (s, 3 H) 4.33 (d, J=6.10 Hz, 2 H) 6.44 (s, 2 H) 6.92-7.12 (m, 3 H) 7.15-7.29 (m, 2 H) 7.34 (t, J=7.80 Hz, 1 H) 7.64 (d, J=8.14 Hz, 1 H) 7.71 (s, 1 H) 7.77 (d, J=8.48 Hz, 1 H) 7.94-8.17 (m, 1 H) 8.36 (d, J=2.03 Hz, 1 H) 10.61 (s, 1 H). MS (ESI(+)) m/e 468 (M+H)$^+$.

EXAMPLE 96

3-amino-N-(3-(((((4-chlorophenyl)amino)carbonyl)amino)methyl)phenyl)-7-methoxy-1,2-benzisoxazole-4-carboxamide The title compound was prepared by substituting 1-chloro-4-isocyanatobenzene for 1-fluoro-3-isocyanatobenzene and EXAMPLE 81A for EXAMPLE 1B in EXAMPLE 1C and 1D, respectively. $^1$H NMR (500 MHz, DMSO-d$_6$) ppm 4.01 (s, 3 H) 4.31 (d, J=6.10 Hz, 2 H) 6.44 (s, 2 H) 6.68 (t, J=5.93 Hz, 1 H) 7.08 (d, J=7.46 Hz, 1 H) 7.17-7.38 (m, 4 H) 7.39-7.48 (m, 2 H) 7.63 (d, J=8.14 Hz, 1 H) 7.70 (s, 1 H) 7.77 (d, J=8.14 Hz, 1 H) 8.72 (s, 1 H) 10.60 (s, 1 H). MS (ESI(+)) m/e 433 (M+H)$^+$.

EXAMPLE 97

3-amino-7-methoxy-N-(3-(((((4-methylphenyl)amino)carbonyl)amino)methyl)phenyl)-1,2-benzisoxazole-4-carboxamide The title compound was prepared by substituting 1-isocyanato-4-methylbenzene for 1-fluoro-3-isocyanatobenzene and EXAMPLE 81A for EXAMPLE 1B in EXAMPLE 1C and 1D, respectively. $^1$H NMR (500 MHz, DMSO-d$_6$) ppm 2.21 (s, 3 H) 4.01 (s, 3 H) 4.30 (d, J=5.76 Hz, 2 H) 6.44 (s, 1 H) 6.56 (t, J=5.93 Hz, 2 H) 6.99-7.12 (m, 3 H) 7.18-7.38 (m, 4 H) 7.63 (d, J=8.14 Hz, 1 H) 7.70 (s, 1 H) 7.77 (d, J=8.14 Hz, 1 H) 8.42 (s, 1 H) 10.61 (s, 1 H). MS (ESI(+)) m/e 433 (M+H)$^+$.

EXAMPLE 98

3-amino-N-(3-(((((2,5-difluorophenyl)amino)carbonyl)amino)methyl)phenyl)-7-methoxy-1,2-benzisoxazole-4-carboxamide The title compound was prepared by substituting 1,4-difluoro-2-isocyanatobenzene for 1-fluoro-3-isocyanatobenzene and EXAMPLE 81A for EXAMPLE 1B in EXAMPLE 1C and 1D, respectively. $^1$H NMR (300 MHz, DMSO-d$_6$) ppm 4.02 (s, 3 H) 4.34 (d, J=5.55 Hz, 2 H) 6.46 (s, 2 H) 6.60-6.84 (m, 1 H) 7.09 (d, J=7.54 Hz, 1 H) 7.16-7.28 (m, 3 H) 7.35 (t, J=7.93 Hz, 1 H) 7.65 (d, J=7.93 Hz, 1 H) 7.70 (s, 1 H) 7.78 (d, J=8.33 Hz, 1 H) 7.91-8.17 (m, 1 H) 8.65 (s, 1 H) 10.64 (s, 1 H). MS (ESI(+)) m/e 468 (M+H)$^+$.

EXAMPLE 99

3-amino-N-(3-(((((4-(difluoromethoxy)phenyl)amino)carbonyl)amino)methyl)phenyl)-7-methoxy-1,2-benzisoxazole-4-carboxamide The title compound was prepared by substituting 1-(difluoromethoxy)-4-isocyanatobenzene for 1-fluoro-3-isocyanatobenzene and EXAMPLE 81A for EXAMPLE 1B in EXAMPLE 1C and 1D, respectively. $^1$H NMR (500 MHz, DMSO-d$_6$) ppm 4.01 (s, 3 H) 4.31 (d, J=5.55 Hz, 2 H) 6.46 (s, 2 H) 6.66 (t, J=5.95 Hz, 1 H) 6.99-7.15 (m, 4 H) 7.23 (d, J=8.33 Hz, 1 H) 7.34 (t, J=7.73 Hz, 1 H) 7.44 (d, J=9.12 Hz, 2 H) 7.63 (d, J=7.93 Hz, 1 H) 7.71 (s, 1 H) 7.77 (d, J=8.33 Hz, 1 H) 8.67 (s, 1 H) 10.63 (s, 1 H). MS (ESI(+)) m/e 498 (M+H)$^+$.

EXAMPLE 100

3-amino-N-(4-((((3-fluorophenyl)amino)carbonyl)amino)-3-methylphenyl)-1,2-benzisoxazole-4-carboxamide

EXAMPLE 100A 1-(3-fluorophenyl)-3-(2-methyl-4-nitrophenyl)urea

The title compound was prepared by substituting 1-isocyanato-2-methyl-4-nitrobenzene and 3-fluoroaniline for 1-fluoro-3-isocyanatobenzene and 3-(aminomethyl)aniline in EXAMPLE 1C. MS (ESI(+)) m/e 290 (M+H)$^+$.

EXAMPLE 100B 1-(4-amino-2-methylphenyl)-3-(3-fluorophenyl)urea

A solution of EXAMPLE 100A (1.28 g, 4.43 mmol) in 12 mL of N,N-dimethylformamide was degassed and hydrogenated under an atmosphere of hydrogen (balloon) in the presence of catalytic amount of 10% Pd on carbon for 24 hours. The mixture was filtered and the filtrate was extracted with ethyl acetate. The organic extract was washed with brine, dried with MgSO$_4$ and concentrated to provide EXAMPLE 100B. MS (ESI(+)) m/e 260 (M+H)$^+$.

EXAMPLE 100C 3-amino-N-(4-((((3-fluorophenyl)amino)carbonyl)amino)-3-methylphenyl)-1,2-benzisoxazole-4-carboxamide The title compound was prepared by substituting EXAMPLE 100B for EXAMPLE 1C in EXAMPLE 1D. $^1$H NMR (500 MHz, DMSO-d$_6$) δ ppm 2.27 (s, 3 H) 6.35 (s, 2 H) 6.62-6.89 (m, 1 H) 7.11 (d, J=8.14 Hz, 1 H) 7.22-7.41 (m, 1 H) 7.42-7.59 (m, 2 H) 7.59-7.84 (m, 5 H) 8.02 (s, 1 H) 9.18 (s, 1 H) 10.65 (s, 1 H). MS (ESI(+)) m/e 420 (M+H)$^+$.

EXAMPLE 101

3-amino-N-(4-((((3-fluorophenyl)amino)carbonyl) amino)-3-methylphenyl)-7-methoxy-1,2-benzisoxazole-4-carboxamide The title compound was prepared by substituting EXAMPLE 100B and EXAMPLE 81A for EXAMPLES 1C and 1B, respectively in EXAMPLE 1D. $^1$H NMR (500 MHz, DMSO-d$_6$) δ ppm 2.26 (s, 3 H) 4.02 (s, 3 H) 6.48 (s, 2 H) 6.64-6.87 (m, 1 H) 7.10 (d, J=9.12 Hz, 1 H) 7.17-7.39 (m, 2 H) 7.43-7.58 (m, 2 H) 7.61 (d, J=1.98 Hz, 1 H) 7.76 (dd, J=8.53, 6.15 Hz, 2 H) 8.00 (s, 1 H) 9.17 (s, 1 H) 10.48 (s, 1 H). MS (ESI(+)) m/e 450 (M+H)$^+$.

EXAMPLE 102

3-amino-N-(4-((((2-fluorophenyl)amino)carbonyl) amino)-3-methylphenyl)-1,2-benzisoxazole-4-carboxamide The title compound was prepared by substituting 2-fluoroaniline for 3-fluoroaniline in EXAMPLE 100A then following procedures of EXAMPLES 100B-C. $^1$H NMR (300 MHz, DMSO-d$_6$) δ ppm 2.28 (s, 3 H) 6.36 (s, 2 H) 6.90-7.04 (m, 1 H) 7.14 (t, J=7.14 Hz, 1 H) 7.19-7.33 (m, 1 H) 7.46-7.87 (m, 6 H) 8.10-8.27 (m, 1 H) 8.38 (s, 1 H) 8.93 (d, J=2.38 Hz, 1 H) 10.65 (s, 1 H). MS (ESI(+)) m/e 420 (M+H)$^+$.

EXAMPLE 103

3-amino-N-(4-((((2-fluorophenyl)amino)carbonyl) amino)-3-methylphenyl)-7-methoxy-1,2-benzisoxazole-4-carboxamide The title compound was prepared by substituting 2-fluoroaniline for 3-fluoroaniline in EXAMPLE 100A-B then coupling the product with EXAMPLE 81A as described in EXAMPLE 1D. $^1$H NMR (300 MHz, DMSO-d$_6$) δ ppm 2.28 (s, 3 H) 4.02 (s, 3 H) 6.49 (s, 2 H) 6.91-7.05 (m, 1 H) 7.14 (t, J=7.63 Hz, 1 H) 7.18-7.33 (m, 2 H) 7.50 (dd, J=8.81, 2.37 Hz, 1 H) 7.60 (d, J=2.03 Hz, 1 H) 7.79 (dd, J=11.36, 8.65 Hz, 2 H) 8.07-8.29 (m, 1 H) 8.37 (s, 1 H) 8.92 (d, J=2.71 Hz, 1 H) 10.48 (s, 1 H). MS (ESI(+)) m/e 450 (M+H)$^+$.

EXAMPLE 104

3-amino-N-(3-methyl-4-((((4-(trifluoromethyl)phenyl)amino)carbonyl)amino)phenyl)-1,2-benzisoxazole-4-carboxamide The title compound was prepared by substituting 4-trifluomethylaniline for 3-fluoroaniline in EXAMPLE 100A then following procedures of EXAMPLES 100B-C. $^1$H NMR (300 MHz, DMSO-d$_6$) δ ppm 2.28 (s, 3 H) 6.36 (d, J=1.59 Hz, 2 H) 7.38-7.88 (m, 10 H) 8.08 (s, 1 H) 9.37 (s, 1 H) 10.66 (s, 1 H). MS (ESI(+)) m/e 470 (M+H)$^+$.

EXAMPLE 105

3-amino-7-methoxy-N-(3-methyl-4-((((4-(trifluoromethyl)phenyl)amino)carbonyl)amino)phenyl)-1,2-benzisoxazole-4-carboxamide The title compound was prepared by substituting 4-trifluoromethylaniline for 3-fluoroaniline in EXAMPLE 100A-B then coupling the product with EXAMPLE 81A as described in EXAMPLE 1D. $^1$H NMR (300 MHz, DMSO-d$_6$) δ ppm 2.27 (s, 3 H) 4.02 (s, 3 H) 6.48 (s, 2 H) 7.23 (d, J=8.33 Hz, 1 H) 7.45-7.91 (m, 8 H) 8.07 (s, 1 H) 9.36 (s, 1 H) 10.49 (s, 1 H). MS (ESI(+)) m/e 500 (M+H)$^+$.

EXAMPLE 106

3-amino-N-(3-(((((4-chlorophenyl)amino)carbonyl) amino)methyl)-4-fluorophenyl)-1,2-benzisoxazole-4-carboxamide

EXAMPLE 106A 3-amino-N-(3-(aminomethyl)-4-fluorophenyl)benzo (d)isoxazole-4-carboxamide The title compound was prepared following the procedures of EXAMPLE 5A and EXAMPLE 5B, substituting tert-butyl 5-amino-2-fluorobenzylcarbamate for tert-butyl 3-aminobenzylcarbamate in EXAMPLE 5A. MS (ESI(+)) m/e 301 (M+H)$^+$.

EXAMPLE 106B

The title compound was prepared by substituting 1-chloro-4-isocyanatobenzene for 1-isocyanato-4-methylbenzene and EXAMPLE 106A for EXAMPLE 5B in EXAMPLE 5C. $^1$H NMR (300 MHz, DMSO-d$_6$) δ ppm 4.36 (d, J=5.76 Hz, 2 H) 6.32 (s, 2 H) 6.71 (t, J=5.93 Hz, 1 H) 7.08-7.33 (m, 3 H) 7.34-7.48 (m, 2 H) 7.57-7.96 (m, 5 H) 8.79 (s, 1 H) 10.83 (s, 1 H). MS (ESI(+)) m/e 454 (M+H)$^+$.

EXAMPLE 107

3-amino-N-(4-fluoro-3-(((((4-methylphenyl)amino) carbonyl)amino)methyl)phenyl)-1,2-benzisoxazole-4-carboxamide The title compound was prepared by substituting EXAMPLE 106A for EXAMPLE 5B in EXAMPLE 5C. $^1$H NMR (300 MHz, DMSO-d$_6$) δ ppm 2.20 (s, 3 H) 4.35 (d, J=5.76 Hz, 2 H) 6.32 (s, 2 H) 6.59 (s, 1 H) 7.02 (d, J=8.14 Hz, 2 H) 7.12-7.37 (m, 3 H) 7.52-7.85 (m, 5 H) 8.49 (s, 1 H) 10.84 (s, 1 H). MS (ESI(+)) m/e 434 (M+H)$^+$.

EXAMPLE 108

3-amino-N-(3-(((((4-(difluoromethoxy)phenyl) amino)carbonyl)amino)methyl)-4-fluorophenyl)-1,2-benzisoxazole-4-carboxamide The title compound was prepared by substituting 1-(difluoromethoxy)-4-isocyanatobenzene for 1-isocyanato-4-methylbenzene and EXAMPLE 106A for EXAMPLE 5B in EXAMPLE 5C. $^1$H NMR (300 MHz, DMSO-d$_6$) δ ppm 4.36 (d, J=5.76 Hz, 2 H) 6.32 (s, 2 H) 6.66 (t, J=6.10 Hz, 2 H)

6.99-7.12 (m, 2 H) 7.14-7.28 (m, 1 H) 7.37-7.51 (m, 2 H) 7.58-8.03 (m, 5 H) 8.71 (s, 1 H) 10.83 (s, 1 H). MS (ESI(+)) m/e 486 (M+H)$^+$.

EXAMPLE 109

3-amino-N-(4-fluoro-3-(((((2-fluoro-5-methylphenyl)amino)carbonyl)amino)methyl)phenyl)-1,2-benzisoxazole-4-carboxamide The title compound was prepared by substituting 1-fluoro-2-isocyanato-4-methylbenzene for 1-isocyanato-4-methylbenzene and EXAMPLE 106A for EXAMPLE 5B in EXAMPLE 5C. $^1$H NMR (300 MHz, DMSO-d$_6$) ☐ ppm 2.22 (s, 3 H) 4.37 (d, J=5.76 Hz, 2 H) 6.31 (s, 2 H) 6.59-6.79 (m, 1 H) 6.92-7.37 (m, 3 H) 7.57-7.86 (m, 5 H) 7.97 (dd, J=7.97, 1.86 Hz, 1 H) 8.36 (d, J=2.37 Hz, 1 H) 10.83 (s, 1 H). MS (ESI(+)) m/e 452 (M+H)$^+$.

EXAMPLE 110

3-amino-N-(3-(((((4-chloro-2-fluorophenyl)amino)carbonyl)amino)methyl)-4-fluorophenyl)-1,2-benzisoxazole-4-carboxamide The title compound was prepared by substituting 4-chloro-2-fluoro-1-isocyanatobenzene for 1-isocyanato-4-methylbenzene and EXAMPLE 106A for EXAMPLE 5B in EXAMPLE 5C. $^1$H NMR (300 MHz, DMSO-d$_6$) ☐ ppm 4.38 (d, J=5.55 Hz, 2 H) 6.32 (s, 2 H) 7.03-7.30 (m, 3 H) 7.40 (dd, J=11.10, 2.38 Hz, 1 H) 7.60-7.93 (m, 5 H) 8.16 (t, J=8.92 Hz, 1 H) 8.56 (d, J=2.78 Hz, 1 H) 10.83 (s, 1 H). MS (ESI(+)) m/e 472 (M+H)$^+$.

EXAMPLE 111

3-amino-N-(4-fluoro-3-(((((4-(trifluoromethyl)phenyl)amino)carbonyl)amino)methyl)phenyl)-1,2-benzisoxazole-4-carboxamide The title compound was prepared by substituting 1-isocyanato-4-(trifluoromethyl)benzene for 1-isocyanato-4-methylbenzene and EXAMPLE 106A for EXAMPLE 5B in EXAMPLE 5C. $^1$H NMR (300 MHz, DMSO-d$_6$) ☐ ppm 4.40 (d, J=5.76 Hz, 2 H) 6.28 (s, 2 H) 6.77 (t, J=5.93 Hz, 1 H) 7.01-7.27 (m, 1 H) 7.37-7.91 (m, 9 H) 8.99 (s, 1 H) 10.77 (s, 1 H). MS (ESI(+)) m/e 488 (M+H)$^+$.

EXAMPLE 112

3-amino-N-(3-(((anilinocarbonyl)amino)methyl)-4-fluorophenyl)-1,2-benzisoxazole-4-carboxamide The title compound was prepared by substituting isocyanatobenzene for 1-isocyanato-4-methylbenzene and EXAMPLE 106A for EXAMPLE 5B in EXAMPLE 5C. $^1$H NMR (300 MHz, DMSO-d$_6$) ☐ ppm 4.36 (d, J=5.95 Hz, 2 H) 6.31 (s, 2 H) 6.65 (t, J=5.95 Hz, 1 H) 6.89 (t, J=7.34 Hz, 1 H) 7.12-7.33 (m, 3 H) 7.34-7.52 (m, 2 H) 7.59-7.86 (m, 5 H) 8.61 (s, 1 H) 10.83 (s, 1 H). MS (ESI(+)) m/e 420 (M+H)$^+$.

EXAMPLE 113

3-amino-N-(4-fluoro-3-(((((4-fluorophenyl)amino)carbonyl)amino)methyl)phenyl)-1,2-benzisoxazole-4-carboxamide The title compound was prepared by substituting 1-fluoro-4-isocyanatobenzene for 1-isocyanato-4-methylbenzene and EXAMPLE 106A for EXAMPLE 5B in EXAMPLE 5C. $^1$H NMR (300 MHz, DMSO-d$_6$) ☐ ppm 4.36 (d, J=5.76 Hz, 2 H) 6.31 (s, 2 H) 6.64 (t, J=5.93 Hz, 1 H) 6.95-7.95 (m, 10 H) 8.65 (s, 1 H) 10.82 (s, 1 H). MS (ESI(+)) m/e 438 (M+H)$^+$.

EXAMPLE 114

3-amino-N-(4-fluoro-3-(((((3-(trifluoromethyl)phenyl)amino)carbonyl)amino)methyl)phenyl)-1,2-benzisoxazole-4-carboxamide The title compound was prepared by substituting 1-isocyanato-3-(trifluoromethyl)benzene for 1-isocyanato-4-methylbenzene and EXAMPLE 106A for EXAMPLE 5B in EXAMPLE 5C. $^1$H NMR (300 MHz, DMSO-d$_6$) ☐ ppm 4.38 (d, J=5.95 Hz, 2 H) 6.31 (s, 2 H) 6.81 (t, J=5.95 Hz, 1 H) 7.02-7.36 (m, 2 H) 7.36-7.57 (m, 2 H) 7.59-7.89 (m, 5 H) 7.99 (s, 1 H) 9.04 (s, 1 H) 10.83 (s, 1 H) MS (ESI(+)) m/e 488 (M+H)$^+$.

EXAMPLE 115

3-amino-N-(3-(((((2,5-difluorophenyl)amino)carbonyl)amino)methyl)-4-fluorophenyl)-1,2-benzisoxazole-4-carboxamide The title compound was prepared by substituting 2,4-difluoro-1-isocyanatobenzene for 1-isocyanato-4-methylbenzene and EXAMPLE 106A for EXAMPLE 5B in EXAMPLE 5C. $^1$H NMR (300 MHz, DMSO-d$_6$) ☐ ppm 4.38 (d, J=5.95 Hz, 2 H) 6.31 (s, 2 H) 6.60-6.84 (m, 1 H) 7.14-7.38 (m, 3 H) 7.55-7.86 (m, 5 H) 7.90-8.16 (m, 1 H) 8.68 (s, 1 H) 10.83 (s, 1 H). MS (ESI(+)) m/e 456 (M+H)$^+$.

EXAMPLE 116

3-amino-N-(3-(((4-fluorobenzoyl)amino)methyl)phenyl)-1,2-benzisoxazole-4-carboxamide The title compound was prepared by substituting EXAMPLE 5B for EXAMPLE 1C and 4-fluorobenzoic acid for EXAMPLE 1B in EXAMPLE 1D. $^1$H NMR (300 MHz, DMSO-d$_6$) ☐ ppm 4.50 (d, J=5.95 Hz, 2 H) 6.31 (s, 2 H) 7.13 (d, J=7.54 Hz, 1 H) 7.22-7.50 (m, 3 H) 7.56-7.83 (m, 5 H) 7.85-8.14 (m, 2 H) 9.11 (t, J=5.95 Hz, 1 H) 10.77 (s, 1 H) MS (ESI(+)) m/e 405 (M+H)$^+$.

EXAMPLE 117

3-amino-N-(3-(((3-fluorobenzoyl)amino)methyl)phenyl)-1,2-benzisoxazole-4-carboxamide The title compound was prepared by substituting EXAMPLE 5B for EXAMPLE 1C and 3-fluorobenzoic acid for EXAMPLE 1B in EXAMPLE 1D. $^1$H NMR (300 MHz, DMSO-d$_6$) ☐ ppm 4.51 (d, J=5.95 Hz, 2 H) 6.31 (s, 2 H) 7.13 (d, J=7.54 Hz, 1 H) 7.28-7.46 (m, 2 H) 7.47-7.62 (m, 1 H) 7.62-7.85 (m, 7 H) 9.18 (t, J=5.95 Hz, 1 H) 10.77 (s, 1 H). MS (ESI(+)) m/e 405 (M+H)$^+$.

EXAMPLE 118

3-amino-N-(3-(((anilinocarbonyl)amino)methyl)-4-methylphenyl)-1,2-benzisoxazole-4-carboxamide The title compound was prepared by substituting aniline for 3-fluoroaniline in EXAMPLE 100A then following procedures of EXAMPLES 100B-C. ¹H NMR (300 MHz, DMSO-d₆) ☐ ppm 2.49 (s, 3 H) 4.49 (d, J=5.55 Hz, 2 H) 6.52 (s, 2 H) 6.72 (t, J=5.75 Hz, 1 H) 7.08 (t, J=7.34 Hz, 1 H) 7.27-7.47 (m, 3 H) 7.59 (d, J=7.54 Hz, 2 H) 7.71-8.03 (m, 5 H) 8.71 (s, 1 H) 10.92 (s, 1 H). MS (ESI(+)) m/e 416 (M+H)⁻.

EXAMPLE 119

3-amino-N-(3-(aminomethyl)phenyl)-1,2-benzisoxazole-4-carboxamide

The title compound was prepared as described in EXAMPLE 5B. ¹H NMR (300 MHz, DMSO-d₆) ☐ ppm 4.07 (q, J=5.76 Hz, 2 H) 6.33 (s, 2 H) 7.27 (d, J=8.14 Hz, 1 H) 7.46 (t, J=7.80 Hz, 1 H) 7.56-7.89 (m, 4 H) 8.03 (s, 1 H) 8.21 (s, 2 H) 10.91 (s, 1 H). MS (ESI(+)) m/e 283 (M+H)⁺.

EXAMPLE 120

3-amino-N-(3-(((((3-fluorophenyl)amino)carbonyl)amino)methyl)phenyl)-1-methyl-1H-indazole-4-carboxamide

EXAMPLE 120A 3-amino-N-(3-(aminomethyl)phenyl)-1-methyl-1H-indazole-4-carboxamide The title compound was prepared following the procedures of EXAMPLES 5A and EXAMPLE 5B, except substituting 4-iodo-1-methyl-1H-indazol-3-amine ((J. Med. Chem. 2007, 50, 1584-1597) for EXAMPLE 1B in EXAMPLE 5A. MS (ESI(+)) m/e 296 (M+H)⁺.

EXAMPLE 120B 3-amino-N-(3-(((((3-fluorophenyl)amino)carbonyl)amino)methyl)phenyl)-1-methyl-1H-indazole-4-carboxamide The title compound was prepared by substituting 1-fluoro-3-isocyanatobenzene for 1-isocyanato-4-methylbenzene and EXAMPLE 120A for EXAMPLE 5B in EXAMPLE 5C. ¹H NMR (300 MHz, DMSO-d₆) ☐ 3.80 (s, 3 H) 4.32 (d, J=5.95 Hz, 2 H) 5.38 (s, 2 H) 6.65-6.75 (m, 2 H) 7.06 (t, J=8.33 Hz, 2 H) 7.18-7.43 (m, 4 H) 7.47 (dt, J=12.29, 2.38 Hz, 1 H) 7.60 (dd, J=7.14, 2.38 Hz, 1 H) 7.65 (d, J=7.14 Hz, 1 H) 7.76 (s, 1 H) 8.82 (s, 1 H) 10.63 (s, 1 H); MS (ESI) m/z 433 (M+H)+.

EXAMPLE 121

3-amino-N-(3-(((((4-chloro-2-fluorophenyl)amino)carbonyl)amino)methyl)phenyl)-1-methyl-1H-indazole-4-carboxamide The title compound was prepared by substituting 4-chloro-2-fluoro-1-isocyanatobenzene for 1-isocyanato-4-methylbenzene and EXAMPLE 120A for EXAMPLE 5B in EXAMPLE 5C. ¹H NMR (300 MHz, DMSO-d₆) ☐ ppm 3.80 (s, 3 H) 4.33 (d, J=5.55 Hz, 2 H) 5.38 (s, 2 H) 7.01-7.23 (m, 3 H) 7.28-7.47 (m, 4 H) 7.56-7.82 (m, 3 H) 8.18 (t, J=8.92 Hz, 1 H) 8.51 (d, J=2.38 Hz, 1 H) 10.64 (s, 1 H); MS (ESI) m/z 467 (M+H)+.

EXAMPLE 122

3-amino-N-(3-(((((4-chlorophenyl)amino)carbonyl)amino)methyl)phenyl)-1-methyl-1H-indazole-4-carboxamide The title compound was prepared by substituting 4-chloro-1-isocyanatobenzene for 1-isocyanato-4-methylbenzene and EXAMPLE 120A for EXAMPLE 5B in EXAMPLE 5C. ¹H NMR (300 MHz, DMSO-d₆) ☐ ppm 3.85 (s, 3 H) 4.31 (d, J=5.76 Hz, 2 H) 6.69 (t, J=6.0 Hz, 1 H) 7.08 (d, J=7.80 Hz, 1 H) 7.22-7.29 (m, 2 H) 7.33 (t, J=7.80 Hz, 1 H) 7.39-7.48 (m, 4 H) 7.66 (dd, J=7.12, 2.37 Hz, 2 H) 7.75 (s, 1 H) 8.73 (s, 1 H) 10.65 (s, 1 H); MS (ESI) m/z 449 (M+H)+.

EXAMPLE 123

3-amino-N-(3-(((((3-fluoro-4-methylphenyl)amino)carbonyl)amino)methyl)phenyl)-1-methyl-1H-indazole-4-carboxamide The title compound was prepared by substituting 2-fluoro-4-isocyanato-1-methylbenzene for 1-isocyanato-4-methylbenzene and EXAMPLE 120A for EXAMPLE 5B in EXAMPLE 5C. ¹H NMR (300 MHz, DMSO-d₆) ☐ ppm 2.10 (d, J=16.28 Hz, 3 H) 3.82 (s, 3 H) 4.31 (d, J=5.76 Hz, 2 H) 6.66 (t, J=5.93 Hz, 1 H) 6.95 (dd, J=8.14, 2.03 Hz, 1 H) 7.09 (t, J=8.82 Hz, 2 H) 7.26-7.45 (m, 4 H) 7.56-7.69 (m, 2 H) 7.75 (s, 1 H) 8.67 (s, 1 H) 10.64 (s, 1 H); MS (ESI) m/z 447 (M+H)+.

EXAMPLE 124

3-amino-N-(3-(((((3-chloro-4-fluorophenyl)amino)carbonyl)amino)methyl)phenyl)-1-methyl-1H-indazole-4-carboxamide The title compound was prepared by substituting 2-chloro-1-fluoro-4-isocyanatobenzene for 1-isocyanato-4-methylbenzene and EXAMPLE 120A for EXAMPLE 5B in EXAMPLE 5C. ¹H NMR (300 MHz, DMSO-d₆) ☐ ppm 3.80 (s, 3 H) 4.31 (d, J=5.55 Hz, 2 H) 5.38 (s, 2 H) 6.76 (t, J=5.95 Hz, 1 H) 7.07 (d, J=7.93 Hz, 1 H) 7.21-7.43 (m, 5 H) 7.60 (dd, J=7.14, 1.98 Hz, 1 H) 7.65 (d, J=9.12 Hz, 1 H) 7.73-7.82 (m, 2 H) 8.81 (s, 1 H) 10.63 (s, 1 H). MS (ESI) m/z 467 (M+H)+.

EXAMPLE 125

3-amino-1-methyl-N-(3-(((((3-(trifluoromethyl)phenyl)amino)carbonyl)amino)methyl)phenyl)-1H-indazole-4-carboxamide The title compound was prepared by substituting 1-isocyanato-3-(trifluoromethyl)benzene for 1-isocyanato-4-methylbenzene and EXAMPLE 120A for EXAMPLE 5B in EXAMPLE 5C. ¹H NMR (300 MHz, DMSO-d₆) ☐ ppm 3.83 (s, 3 H) 4.33 (d, J=5.55 Hz, 2 H) 6.80 (t, J=5.95 Hz, 1 H) 7.09 (d, J=7.93 Hz, 1 H) 7.22 (d, J=7.54 Hz, 1 H) 7.30-7.56 (m, 5 H) 7.59-7.70 (m, 2 H) 7.75 (s, 1 H) 8.00 (s, 1 H) 8.98 (s, 1 H) 10.64 (s, 1 H); MS (ESI) m/z 483 (M+H)+.

EXAMPLE 126

3-amino-1-methyl-N-(3-(((((4-(trifluoromethyl)phenyl)amino)carbonyl)amino)methyl)phenyl)-1H-indazole-4-carboxamide The title compound was prepared by substituting 1-isocyanato-4-(trifluoromethyl)benzene for 1-isocyanato-4-methylbenzene and EXAMPLE 120A for EXAMPLE 5B in EXAMPLE 5C. $^1$H NMR (300 MHz, DMSO-$d_6$) ☐ ppm 3.84 (s, 3 H) 4.33 (d, J=5.55 Hz, 2 H) 6.81 (t, J=5.95 Hz, 1 H) 7.09 (d, J=7.54 Hz, 1 H) 7.39-7.46 (m, 2 H) 7.53-7.70 (m, 6 H) 7.76 (s, 1 H) 9.03 (s, 1 H) 10.65 (s, 1 H); MS (ESI) m/z 483 (M+H)+.

EXAMPLE 127

3-amino-N-(3-(((((4-fluorophenyl)amino)carbonyl)amino)methyl)phenyl)-1-methyl-1H-indazole-4-carboxamide The title compound was prepared by substituting 1-fluoro-4-isocyanatobenzene for 1-isocyanato-4-methylbenzene and EXAMPLE 120A for EXAMPLE 5B in EXAMPLE 5C. $^1$H NMR (300 MHz, DMSO-$d_6$) ☐ ppm 3.85 (s, 3 H) 4.31 (d, J=5.76 Hz, 2 H) 6.63 (t, J=5.76 Hz, 1 H) 7.01-7.12 (m, 3 H) 7.33 (t, J=7.80 Hz, 1 H) 7.37-7.48 (m, 4 H) 7.59-7.70 (m, 2 H) 7.75 (s, 1 H) 8.60 (s, 1 H) 10.65 (s, 1 H); MS (ESI) m/z 433 (M+H)+.

EXAMPLE 128

3-amino-N-(3-(((((2-chlorophenyl)amino)carbonyl)amino)methyl)phenyl)-1-methyl-1H-indazole-4-carboxamide The title compound was prepared by substituting 1-chloro-2-isocyanatobenzene for 1-isocyanato-4-methylbenzene and EXAMPLE 120A for EXAMPLE 5B in EXAMPLE 5C. $^1$H NMR (300 MHz, DMSO-$d_6$) ☐ ppm 3.81 (s, 3 H) 4.33 (d, J=5.76 Hz, 2 H) 6.90-6.99 (m, 1 H) 7.09 (d, J=7.80 Hz, 1 H) 7.24 (td, 1 H) 7.31-7.43 (m, 4 H) 7.51 (t, J=5.76 Hz, 1 H) 7.58-7.65 (m, 1 H) 7.67 (d, J=9.16 Hz, 1 H) 7.78 (s, 1 H) 8.11 (s, 1 H) 8.18 (dd, J=8.31, 1.53 Hz, 1 H) 10.65 (s, 1 H); MS (ESI) m/z 449 (M+H)+.

EXAMPLE 129

3-amino-N-(3-(((((4-methylphenyl)amino)carbonyl)amino)methyl)phenyl)-1H-indazole-4-carboxamide The title compound was prepared by substituting EXAMPLE 54B for EXAMPLE 5B in EXAMPLE 5C and purified by preparative HPLC on a Waters Symmetry C8 column (25 mm×100 mm, 7 µm particle size) using a gradient of 10% to 100% acetonitrile/0.1% aqueous TFA over 8 minutes (10 minute run time) at a flow rate of 40 mL/min. and was isolated as the TFA salt. $^1$H NMR (300 MHz, DMSO-$d_6$) ☐ ppm 2.21 (s, 3 H) 4.31 (d, J=5.43 Hz, 2 H) 6.57 (t, J=5.93 Hz, 1 H) 7.02 (d, J=8.14 Hz, 2 H) 7.08 (d, J=7.80 Hz, 1 H) 7.25-7.51 (m, 5 H) 7.56 (d, J=8.14 Hz, 1 H) 7.67 (d, J=7.80 Hz, 1 H) 7.75 (s, 1 H) 8.43 (s, 1 H) 10.65 (s, 1 H); MS (ESI) m/z=415 (M+H)+.

EXAMPLE 130

3-amino-N-(3-(((((2-fluorophenyl)amino)carbonyl)amino)methyl)phenyl)-1H-indazole-4-carboxamide The title compound was prepared by substituting EXAMPLE 54B and 1-fluoro-2-isocyanatobenzene for EXAMPLE 5B and 1-isocyanato-4-methylbenzene, respectively in EXAMPLE 5C and purified by preparative HPLC on a Waters Symmetry C8 column (25 mm×100 mm, 7 µm particle size) using a gradient of 10% to 100% acetonitrile/ 0.1% aqueous TFA over 8 minutes (10 minute run time) at a flow rate of 40 mL/min. and was isolated as the TFA salt. $^1$H NMR (300 MHz, DMSO-$d_6$) ☐ ppm 4.34 (d, J=5.76 Hz, 2 H) 6.87-6.98 (m, 1 H) 7.03-7.23 (m, 4 H) 7.36 (t, J=7.80 Hz, 1 H) 7.40-7.48 (m, 1 H) 7.49-7.56 (m, 1 H) 7.59 (d, J=8.14 Hz, 1 H) 7.69 (d, J=8.14 Hz, 1 H) 7.75 (s, 1 H) 8.15 (td, J=8.31, 1.70 Hz, 1 H) 8.39 (d, J=2.37 Hz, 1 H) 10.68 (s, 1 H); MS (ESI) m/z=419 (M+H)+.

EXAMPLE 131

3-amino-N-(3-(((((4-isopropylphenyl)amino)carbonyl)amino)methyl)phenyl)-1H-indazole-4-carboxamide The title compound was prepared by substituting EXAMPLE 54B and 1-isocyanato-4-isopropylbenzene for EXAMPLE 5B and 1-isocyanato-4-methylbenzene, respectively in EXAMPLE 5C and purified by preparative HPLC on a Waters Symmetry C8 column (25 mm×100 mm, 7 µm particle size) using a gradient of 10% to 100% acetonitrile/ 0.1% aqueous TFA over 8 minutes (10 minute run time) at a flow rate of 40 mL/min. and was isolated as the TFA salt. $^1$H NMR (300 MHz, DMSO-$d_6$) ☐ ppm 1.16 (d, J=6.78 Hz, 6 H) 2.71-2.88 (m, 1 H) 4.31 (d, J=5.76 Hz, 2 H) 6.57 (t, J=5.93 Hz, 1 H) 7.04-7.12 (m, 3 H) 7.27-7.47 (m, 5 H) 7.53 (d, J=7.80 Hz, 1 H) 7.66 (d, J=7.80 Hz, 1 H) 7.75 (s, 1 H) 8.44 (s, 1 H) 10.64 (s, 1H); MS (ESI) m/z=433 (M+H)+.

The foregoing is meant to illustrate the invention but not to limit it. Variations and changes obvious to one skilled in the art are intended to be within the scope of the invention as defined in the claims.

We claim:
1. A compound having Formula I

(I)

or a therapeutically acceptable salt thereof, wherein
X is S, O or NG$^1$;
G$^1$ is H or is alkyl, alkenyl or alkynyl, each of which is unsubstituted or substituted with one, two, three, four or five of independently selected R$^6$, OR$^6$, NH$_2$, NHR$^6$, N(R$^6$)$_2$, OH or (O);
A$^1$ is C(O)NHR$^1$;
B$^1$, C$^1$, and D$^1$ are H;
R$^1$ is R$^2$;
R$^2$ is phenyl;
wherein R$^2$ is substituted with one or two or three or four or five of independently selected R$^{10}$, OR$^{10}$, SR$^{10}$, S(O)R$^{10}$, SO$_2$R$^{10}$, C(O)R$^{10}$, CO(O)R$^{10}$, OC(O)R$^{10}$, OC(O)OR$^{10}$, NH$_2$, NHR$^{10}$, N(R$^{10}$)$_2$, NHC(O)R$^{10}$, NR$^{10}$C(O)R$^{10}$, NHS(O)$_2$R$^{10}$, NR$^{10}$S(O)$_2$R$^{10}$, NHC(O)OR$^{10}$, NR$^{10}$C(O)OR$^{10}$, NHC(O)NH$_2$, NHC(O)NHR$^{10}$,)NHC(O)N(R$^{10}$)$_2$, NR$^{10}$C(O)NHR$^{10}$,)NR$^{10}$C(O)N(R$^{10}$)$_2$, C(O)NH$_2$, C(O)NHR$^{10}$, C(O)N(R$^{10}$)$_2$C(O)NHOH, C(O)NHOR$^{10}$, C(O)NHSO$_2$R$^{10}$, C(O)NR$^{10}$SO$_2$R$^{10}$, SO$_2$NH$_2$, SO$_2$NHR$^{10}$,)SO$_2$N(R$^{10}$)$_2$, C(O)H, C(O)OH, C(N)NH$_2$, C(N)NHR$^{10}$, C(N)N(R$^{10}$)$_2$, CNOH, CNOCH$_3$, OH, (O), CN, N$_3$, NO$_2$, CF$_3$, CF$_2$CF$_3$, OCF$_3$, OCF$_2$CF$_3$, F, Cl, Br or I;

R$^{10}$ is R$^{11}$, R$^{12}$, R$^{13}$ or R$^{14}$;

R$^{11}$ is phenyl which is unfused or fused with benzene, heteroarene or R$^{11.4}$; R$^{11.4}$ is cycloalkane, cycloalkene, heterocycloalkane or heterocycloalkene;

R$^{12}$ is heteroaryl which is unfused or fused with benzene, heteroarene or R$^{12.4}$; R$^{12.4}$ is cycloalkane, cycloalkene, heterocycloalkane or heterocycloalkene;

R$^{13}$ is cycloalkyl, cycloalkenyl, heterocycloalkyl or heterocycloalkenyl, each of which is unfused or fused with benzene, heteroarene or R$^{13.4}$; R$^{13.4}$ is cycloalkane, cycloalkene, heterocycloalkane or heterocycloalkene;

R$^{14}$ is alkyl, alkenyl or alkenyl, each of which is unsubstituted or substituted with one, two, three, four or five of independently selected R$^{15}$, OR$^{15}$, SR$^{15}$, S(O)R$^{15}$, SO$_2$R$^{15}$, CO(O)R$^{15}$, OC(O)R$^{15}$, OC(O)OR$^{15}$, NH$_2$, NHR$^{15}$, N(R$^{15}$)$_2$, NHC(O)R$^{15}$, NR$^{15}$C(O)R$^{15}$, NHS(O)$_2$R$^{15}$, NR$^{15}$S(O)$_2$R$^{15}$, NHC(O)OR$^{15}$, NR$^{15}$C(O)OR$^{15}$, NHC(O)NH$_2$, NHC(O)NHR$^{15}$, NHC(O)N(R$^{15}$)$_2$, NR$^{15}$C(O)NHR$^{15}$, NR$^{15}$C(O)N(R$^{15}$)$_2$, C(O)NH$_2$, C(O)NHR$^{15}$, C(O)N(R$^{15}$)$_2$, C(O)NHOH, C(O)NHOR$^{15}$, C(O)NHSO$_2$R$^{15}$, C(O)NR$^{15}$SO$_2$R$^{15}$, SO$_2$NH$_2$, SO$_2$NHR$^{15}$, SO$_2$N(R$^{15}$)$_2$, C(O)OH, C(N)NH$_2$, C(N)NHR$^{15}$, C(N)N(R$^{15}$)$_2$, CNOH, CNOCH$_3$, OH, (O), CN, N$_3$, NO$_2$, CF$_3$, CF$_2$CF$_3$, OCF$_3$, OCF$_2$CF$_3$, F, Cl, Br or I;

R$^{15}$ is R$^{16}$, R$^{17}$, R$^{18}$ or R$^{19}$;

R$^{16}$ is phenyl which is unfused or fused with benzene, heteroarene or R$^{16.4}$; R$^{16.4}$ is cycloalkane, cycloalkene, heterocycloalkane or heterocycloalkene;

R$^{17}$ is heteroaryl which is unfused or fused with benzene, heteroarene or R$^{17.4}$; R$^{17.4}$ is cycloalkane, cycloalkene, heterocycloalkane or heterocycloalkene;

R$^{18}$ is cycloalkyl, cycloalkenyl, heterocycloalkyl or heterocycloalkenyl, each of which is unfused or fused with benzene, heteroarene or R$^{18.4}$; R$^{18.4}$ is cycloalkane, cycloalkene, heterocycloalkane or heterocycloalkene;

R$^{19}$ is alkyl, alkenyl or alkenyl, each of which is unsubstituted or substituted with R$^{20}$;

R$^{20}$ is phenyl, heteroaryl, cycloalkyl, cycloalkenyl, heterocycloalkyl or heterocycloalkenyl;

wherein the moieties represented by R$^{11}$, R$^{12}$, R$^{13}$, R$^{16}$, R$^{17}$, R$^{18}$ and R$^{20}$ are independently unsubstituted or substituted with one or two or three of independently selected R$^{21}$, OR$^{21}$, SR$^{21}$, S(O)R$^{21}$, SO$_2$R$^{21}$, C(O)R$^{21}$, CO(O)R$^{21}$, OC(O)R$^{21}$, OC(O)OR$^{21}$, NH$_2$, NHR$^{21}$, N(R$^{21}$)$_2$, NHC(O)R$^{21}$, NR$^{21}$C(O)R$^{21}$, NHS(O)$_2$R$^{21}$, NR$^{21}$S(O)$_2$R$^{21}$, NHC(O)OR$^{21}$, NR$^{21}$C(O)OR$^{21}$, NHC(O)NH$_2$, NHC(O)NHR$^{21}$, NHC(O)N(R$^{21}$)$_2$, NR$^{21}$C(O)NHR$^{21}$, NR$^{21}$C(O)N(R$^{21}$)$_2$, C(O)NH$_2$, C(O)NHR$^{21}$, C(O)N(R$^{21}$)$_2$, C(O)NHOH, C(O)NHOR$^{21}$, C(O)NHSO$_2$R$^{21}$, C(O)NR$^{21}$SO$_2$R$^{21}$, SO$_2$NH$_2$, SO$_2$NHR$^{21}$, SO$_2$N(R$^{21}$)$_2$, C(O)H, C(O)OH, C(N)NH$_2$, C(N)NHR$^{21}$, C(N)N(R$^{21}$)$_2$, CNOH, CNOCH$_3$, OH, (O), CN, N$_3$, NO$_2$, CF$_3$, CF$_2$CF$_3$, OCF$_3$, OCF$_2$CF$_3$, F, Cl, Br or I;

R$^{21}$ is alkyl, alkenyl or alkynyl, each of which is unsubstituted or substituted with one or two or three of independently selected R$^{22}$, F, Cl, Br, I, OH, C(O)OH, NO$_2$ or NH$_2$; and R$^{22}$ K is phenyl, heteroaryl, cycloalkyl, cycloalkenyl or heterocycloalkyl.

2. A compound of claim 1 which is 3-amino-N-(3-(((((3-fluorophenyl)amino)carbonyl)amino)methyl)phenyl)-1,2-benzisoxazole-4-carboxamide, 3-amino-N-(3-(((((2-fluorophenyl)amino)carbonyl)amino)methyl)phenyl)-1,2-benzisoxazole-4-carboxamide, 3-amino-N-(3-(((anilinocarbonyl)amino)methyl)phenyl)-1,2-benzisoxazole-4-carboxamide, 3-amino-N-(3-(((((4-(trifluoromethyl)phenyl)amino)carbonyl)amino)methyl)phenyl)-1,2-benzisoxazole-4-carboxamide, 3-amino-N-(3-(((((4-methylphenyl)amino)carbonyl)amino)methyl)phenyl)-1,2-benzisoxazole-4-carboxamide, 3-amino-N-(3-(((((2-fluoro-5-methylphenyl)amino)carbonyl)amino)methyl)phenyl)-1,2-benzisoxazole-4-carboxamide, 3-amino-N-(3-(((((3-methoxyphenyl)amino)carbonyl)amino)methyl)phenyl)-1,2-benzisoxazole-4-carboxamide, 3-amino-N-(3-(((((4-methoxyphenyl)amino)carbonyl)amino)methyl)phenyl)-1,2-benzisoxazole-4-carboxamide, 3-amino-N-(3-(((((3,4-difluorophenyl)amino)carbonyl)amino)methyl)phenyl)-1,2-benzisoxazole-4-carboxamide, 3-amino-N-(3-(((((3,5-difluorophenyl)amino)carbonyl)amino)methyl)phenyl)-1,2-benzisoxazole-4-carboxamide, 3-amino-N-(3-(((((4-fluorophenyl)amino)carbonyl)amino)methyl)phenyl)-1,2-benzisoxazole-4-carboxamide, 3-amino-N-(3-((((cyclopentylamino)carbonyl)amino)methyl)phenyl)-1,2-benzisoxazole-4-carboxamide, 3-amino-N-(3-((((cyclohexylamino)carbonyl)amino)methyl)phenyl)-1,2-benzisoxazole-4-carboxamide, 3-amino-N-(3-((((thien-2-ylamino)carbonyl)amino)methyl)phenyl)-1,2-benzisoxazole-4-carboxamide, 3-amino-N-(3-((((thien-3-ylamino)carbonyl)amino)methyl)phenyl)-1,2-benzisoxazole-4-carboxamide, 3-amino-N-(3-(((((3-methylphenyl)amino)carbonyl)amino)methyl)phenyl)-1,2-benzisoxazole-4-carboxamide, 3-amino-N-(3-(((((3,5-dimethylphenyl)amino)carbonyl)amino)methyl)phenyl)-1,2-benzisoxazole-4-carboxamide, 3-amino-N-(3-(((((3-chlorophenyl)amino)carbonyl)amino)methyl)phenyl)-1,2-benzisoxazole-4-carboxamide, 3-amino-N-(3-(((((2-(trifluoromethyl)phenyl)amino)carbonyl)amino)methyl)phenyl)-1,2-benzisoxazole-4-carboxamide, 3-amino-N-(3-(((3-methylbenzoyl)amino)methyl)phenyl)-1,2-benzisoxazole-4-carboxamide, 3-amino-N-(3-((benzoylamino)methyl)phenyl)-1,2-benzisoxazole-4-carboxamide, 3-amino-N-(3-(((phenylacetyl)amino)methyl)phenyl)-1,2-benzisoxazole-4-carboxamide, 3-amino-N-(4-((((3-fluorophenyl)amino)carbonyl)amino)phenyl)-1,2-benzisoxazole-4-carboxamide, 3-amino-N-(4-((andinocarbonyl)amino)phenyl)-1,2-benzisoxazole-4-carboxamide, 3-amino-N-(4-((((3-(trifluoromethyl)phenyl)amino)carbonyl)amino)phenyl)-1,2-benzisoxazole-4-carboxamide, 3-amino-N-(4-(((thien-3-ylamino)carbonyl)amino)phenyl)-1,2-benzisoxazole-4-carboxamide, 3-amino-N-(4-(4-((((4-methylphenyl)amino)carbonyl)amino)phenyl)-1,2-benzisoxazole-4-carboxamide, 3-amino-N-(4-((((3-methylphenyl)amino)carbonyl)amino)phenyl)-1,2-benzisoxazole-4-carboxamide,
3-amino-N-(4-((((2,4-difluorophenyl)amino)carbonyl)amino)phenyl)-1,2-benzisoxazole-4-carboxamide,
3-amino-N-(4-((((3,5-difluorophenyl)amino)carbonyl)amino)phenyl)-1,2-benzisoxazole-4-carboxamide,
3-amino-N-(4-((((3,4-difluorophenyl)amino)carbonyl)amino)phenyl)-1,2-benzisoxazole-4-carboxamide,
3-amino-N-(4-((anilinocarbonyl)amino)phenyl)-7-methyl-1,2-benzisoxazole-4-carboxamide,
3-amino-N-(4-(benzoylamino)phenyl)-1,2-benzisoxazole-4-carboxamide,
3-amino-N-(3-(((((3-fluorophenyl)amino)carbonyl)amino)methyl)phenyl)-1,2-benzisothiazole-4-carboxamide,
3-amino-N-(3-(((anilinocarbonyl)amino)methyl)phenyl)-1,2-benzisothiazole-4-carboxamide,
3-amino-N-(3-(((((4-(trifluoromethyl)phenyl)amino)carbonyl)amino)methyl)phenyl)-1,2-benzisothiazole-4-carboxamide,
3-amino-N-(4-((((3-fluorophenyl)amino)carbonyl)amino)phenyl)-1,2-benzisothiazole-4-carboxamide,
3-amino-N-(4-((anilinocarbonyl)amino)phenyl)-1,2-benzisothiazole-4-carboxamide,
3-amino-N-(4-((((3-(2-hydroxyethyl)phenyl)amino)carbonyl)amino)phenyl)-1,2-benzisothiazole-4-carboxamide,
3-amino-N-(4-((((3,4-dichlorophenyl)amino)carbonyl)amino)phenyl)-1,2-benzisoxazole-4-carboxamide,
3-amino-N-(4-((((3-methoxyphenyl)amino)carbonyl)amino)phenyl)-1,2-benzisoxazole-4-carboxamide,
3-amino-N-(4-((((4-bromophenyl)amino)carbonyl)amino)phenyl)-1,2-benzisoxazole-4-carboxamide,
3-amino-N-(4-(((((4-fluorophenyl)amino)carbonyl)amino)phenyl)-1,2-benzisoxazole-4-carboxamide,
3-amino-N-(4-(((((4-chlorophenyl)amino)carbonyl)amino)phenyl)-1,2-benzisoxazole-4-carboxamide,
3-amino-N-(4-(((((4-methoxyphenyl)amino)carbonyl)amino)phenyl)-1,2-benzisoxazole-4-carboxamide,
3-amino-N-(4-(((benzylamino)carbonyl)amino)phenyl)-1,2-benzisoxazole-4-carboxamide,
3-amino-N-(4-(((((3-cyanophenyl)amino)carbonyl)amino)phenyl)-1,2-benzisoxazole-4-carboxamide,
3-amino-N-(4-((((3-(methylthio)phenyl)amino)carbonyl)amino)phenyl)-1,2-benzisoxazole-4-carboxamide,
3-amino-N-(4-((((4-(methylthio)phenyl)amino)carbonyl)amino)phenyl)-1,2-benzisoxazole-4-carboxamide,
3-amino-N-(4-((((3-chloro-4-fluorophenyl)amino)carbonyl)amino)phenyl)-1,2-benzisoxazole-4-carboxamide,
3-amino-N-(3-(((((4-fluorophenyl)amino)carbonyl)amino)methyl)phenyl)-1H-indazole-4-carboxamide,
3-amino-N-(3-(((((3-chlorophenyl)amino)carbonyl)amino)methyl)phenyl)-1H-indazole-4-carboxamide,
3-amino-N-(3-(((((4-(trifluoromethoxy)phenyl)amino)carbonyl)amino)methyl)phenyl)-1H-indazole-4-carboxamide,
3-amino-N-(3-(((((3-methylphenyl)amino)carbonyl)amino)methyl)phenyl)-1H-indazole-4-carboxamide,
3-amino-N-(3-(((((4-(trifluoromethyl)phenyl)amino)carbonyl)amino)methyl)phenyl)-1H-indazole-4-carboxamide,
3-amino-N-(3-(((((3-(trifluoromethyl)phenyl)amino)carbonyl)amino)methyl)phenyl)-1H-indazole-4-carboxamide,
3-amino-N-(3-(((((3-fluorophenyl)amino)carbonyl)amino)methyl)phenyl)-1H-indazole-4-carboxamide,
3-amino-N-(4-((anilinocarbonyl)amino)phenyl)-1H-indazole-4-carboxamide,
3-amino-N-(4-((((3-fluorophenyl)amino)carbonyl)amino)phenyl)-1H-indazole-4-carboxamide,
3-amino-N-(3-(1-((((3-fluorophenyl)amino)carbonyl)amino)ethyl)phenyl)-1,2-benzisoxazole-4-carboxamide,
3-amino-N-(3-(((anilinocarbonyl)amino)methyl)phenyl)-1H-indazole-4-carboxamide,
3-amino-N-(3-(((((4-chlorophenyl)amino)carbonyl)amino)methyl)phenyl)-1H-indazole-4-carboxamide,
3-amino-N-(3-(((((4-chloro-2-fluorophenyl)amino)carbonyl)amino)methyl)phenyl)-1H-indazole-4-carboxamide,
3-amino-N-(3-(((((3-fluoro-4-methylphenyl)amino)carbonyl)amino)methyl)phenyl)-1H-indazole-4-carboxamide,
3-amino-N-(3-(((((2-fluoro-5-methylphenyl)amino)carbonyl)amino)methyl)phenyl)-1H-indazole-4-carboxamide,
3-amino-N-(3-(((((2-fluoro-5-(trifluoromethyl)phenyl)amino)carbonyl)amino)methyl)phenyl)-1H-indazole-4-carboxamide,
3-amino-N-(3-(((((3,5-difluorophenyl)amino)carbonyl)amino)methyl)phenyl)-1H-indazole-4-carboxamide,
3-amino-N-(3-(((((3,4-difluorophenyl)amino)carbonyl)amino)methyl)phenyl)-1H-indazole-4-carboxamide,
3-amino-N-(3-(((((3-fluoro-4-methylphenyl)amino)carbonyl)amino)methyl)phenyl)-1,2-benzisoxazole-4-carboxamide,
3-amino-N-(3-(((((4-chlorophenyl)amino)carbonyl)amino)methyl)phenyl)-1,2-benzisoxazole-4-carboxamide,
3-amino-N-(3-(((((3-bromophenyl)amino)carbonyl)amino)methyl)phenyl)-1,2-benzisoxazole-4-carboxamide,
3-amino-N-(3-(((((4-chloro-2-fluorophenyl)amino)carbonyl)amino)methyl)phenyl)-1,2-benzisoxazole-4-carboxamide;
3-amino-N-(3-((((pyridin-3-ylamino)carbonyl)amino)methyl)phenyl)-1,2-benzisoxazole-4-carboxamide;
3-amino-N-(4-((((3-fluorophenyl)amino)carbonyl)amino)-3-methylphenyl)-1,2-benzisoxazole-4-carboxamide;
3-amino-N-(4-((((3-fluorophenyl)amino)carbonyl)amino)-3-methylphenyl)-7-methoxy-1,2-benzisoxazole-4-carboxamide;
3-amino-N-(4-((((2-fluorophenyl)amino)carbonyl)amino)-3-methylphenyl)-1,2-benzisoxazole-4-carboxamide;
3-amino-N-(4-((((2-fluorophenyl)amino)carbonyl)amino)-3-methylphenyl)-7-methoxy-1,2-benzisoxazole-4-carboxamide;
3-amino-N-(3-methyl-4-((((4-(trifluoromethyl)phenyl)amino)carbonyl)amino)phenyl)-1,2-benzisoxazole-4-carboxamide;
3-amino-7-methoxy-N-(3-methyl-4-((((4-(trifluoromethyl)phenyl)amino)carbonyl)amino)phenyl)-1,2-benzisoxazole-4-carboxamide;
3-amino-N-(3-(((((4-chlorophenyl)amino)carbonyl)amino)methyl)-4-fluorophenyl)-1,2-benzisoxazole-4-carboxamide;
3-amino-N-(4-fluoro-3-(((((4-methylphenyl)amino)carbonyl)amino)methyl)phenyl)-1,2-benzisoxazole-4-carboxamide;

3-amino-N-(3-(((((4-(difluoromethoxy)phenyl)amino)
carbonyl)amino)methyl)-4-fluorophenyl)-1,2-ben-
zisoxazole-4-carboxamide;
3-amino-N-(4-fluoro-3-(((((2-fluoro-5-methylphenyl)
amino)carbonyl)amino)methyl)phenyl)-1,2-benzisox-
azole-4-carboxamide;
3-amino-N-(3-(((((4-chloro-2-fluorophenyl)amino)carbo-
nyl)amino)methyl)-4-fluorophenyl)-1,2-benzisox-
azole-4-carboxamide;
3-amino-N-(4-fluoro-3-(((((4-(trifluoromethyl)phenyl)
amino)carbonyl)amino)methyl)phenyl)-1,2-benzisox-
azole-4-carboxamide;
3-amino-N-(3-(((anilinocarbonyl)amino)methyl)-4-fluo-
rophenyl)-1,2-benzisoxazole-4-carboxamide;
3-amino-N-(4-fluoro-3-(((((4-fluorophenyl)amino)carbo-
nyl)amino)methyl)phenyl)-1,2-benzisoxazole-4-car-
boxamide;
3-amino-N-(4-fluoro-3-(((((3-(trifluoromethyl)phenyl)
amino)carbonyl)amino)methyl)phenyl)-1,2-benzisox-
azole-4-carboxamide;
3-amino-N-(3-(((((2,5-difluorophenyl)amino)carbonyl)
amino)methyl)-4-fluorophenyl)-1,2-benzisoxazole-4-
carboxamide;
3-amino-N-(3-(((4-fluorobenzoyl)amino)methyl)phenyl)-
1,2-benzisoxazole-4-carboxamide;
3-amino-N-(3(((3-fluorobenzoyl)amino)methyl)phenyl)-
1,2-benzisoxazole-4-carboxamide;
3-amino-N-(3-(((anilinocarbonyl)amino)methyl)-4-meth-
ylphenyl)-1,2-benzisoxazole-4-carboxamide;
3-amino-N-(3-(aminomethyl)phenyl)-1,2-benzisoxazole-
4-carboxamide;
3-amino-N-(3-(((((3-fluorophenyl)amino)carbonyl)
amino)methyl)phenyl)-1-methyl-1H-indazole-4-car-
boxamide;
3-amino-N-(3-(((((4-chloro-2-fluorophenyl)amino)carbo-
nyl)amino)methyl)phenyl)-1-methyl-1H-indazole-4-
carboxamide;
3-amino-N-(3-(((((4-chlorophenyl)amino)carbonyl)
amino)methyl)phenyl)-1-methyl-1H-indazole-4-car-
boxamide ;
3-amino-N-(3-(((((3-fluoro-4-methylphenyl)amino)car-
bonyl)amino)methyl)phenyl)-1-methyl-1H-indazole-4-
carboxamide;
3-amino-N-(3-(((((3-chloro-4-fluorophenyl)amino)carbo-
nyl)amino)methyl)phenyl)-1-methyl-1H-indazole-4-
carboxamide;
3-amino-1-methyl-N-(3-(((((3-(trifluoromethyl)phenyl)
amino)carbonyl)amino)methyl)phenyl)-1H-indazole-
4-carboxamide;
3-amino-1-methyl-N-(3-(((((4-(trifluoromethyl)phenyl)
amino)carbonyl)amino)methyl)phenyl)-1H-indazole-
4-carboxamide;
3-amino-N-(3-(((((4-fluorophenyl)amino)carbonyl)
amino)methyl)phenyl)-1-methyl-1H-indazole-4-car-
boxamide;
3-amino-N-(3-(((((2-chlorophenyl)amino)carbonyl)
amino)methyl)phenyl)-1-methyl-1H-indazole-4-car-
boxamide;
3-amino-N-(3-(((((4-methylphenyl)amino)carbonyl)
amino)methyl)phenyl)-1H-indazole-4-carboxamide;
3-amino-N-(3-(((((2-fluorophenyl)amino)carbonyl)
amino)methyl)phenyl)-1H-indazole-4-carboxamide;
3-amino-N-(3-(((((4-isopropylphenyl)amino)carbonyl)
amino)methyl)phenyl)-1H-indazole-4-carboxamide;
or a therapeutically acceptable salt thereof.

3. A composition comprising an excipient and a therapeutically effective amount of a compound having Formula I of claim 1.

4. The compound of claim 1, wherein X is S.

5. The compound of claim 4, wherein $R^2$ is substituted with NHC(O)NHR$^{10}$;
$R^{10}$ is $R^{11}$ or $R^{12}$;
$R^{11}$ is phenyl;
$R^{12}$ is heteroaryl;
wherein the moieties represented by $R^{11}$ and $R^{12}$ are independently unsubstituted or substituted with one or two or three of independently selected $R^{21}$, OR$^{21}$; SR$^{21}$, CN, CF$_3$, OCF$_3$, F, Cl, Br or I; and
$R^{21}$ is alkyl which is unsubstituted or substituted with one or two or three of independently selected F, Cl, Br, I, or OH.

6. The compound of claim 4, wherein $R^2$ is substituted with $R^{10}$,
$R^{10}$ is $R^{14}$;
$R^{14}$ is alkyl which is substituted with NHC(O)R$^{15}$ or NHC(O)NHR$^{15}$;
$R^{15}$ is $R^{16}$;
$R^{16}$ is phenyl;
wherein $R^{16}$ is unsubstituted or substituted with one or two or three of independently selected $R^{21}$, OR$^{21}$, SR$^{21}$, CN, CF$_3$, OCF$_3$, F, Cl, Br or I; and
$R^{21}$ is alkyl which is unsubstituted or substituted with one or two or three of independently selected F, Cl, Br, I, or OH.

7. The compound of claim 4, wherein $R^2$ is substituted with NHC(O)R$^{10}$;
$R^{10}$ is $R^{11}$ or $R^{12}$;
$R^{11}$ is phenyl;
$R^{12}$ is heteroaryl;
wherein the moieties represented by $R^{11}$ and $R^{12}$ are independently unsubstituted or substituted with one or two or three of independently selected $R^{21}$, OR$^{21}$, SR$^{21}$, CN, CF$_3$, OCF$_3$, F, Cl, Br or I; and
$R^{21}$ is alkyl which is unsubstituted or substituted with one or two or three of independently selected F, Cl, Br, I, or OH.

8. The compound of claim 1, wherein X is O.

9. The compound of claim 8, wherein $R^2$ is substituted with NHC(O)NHR$^{10}$;
$R^{10}$ is $R^{11}$ or $R^{12}$;
$R^{11}$ is phenyl;
$R^{12}$ is heteroaryl;
wherein the moieties represented by $R^{11}$ and $R^{12}$ are independently unsubstituted or substituted with one or two or three of independently selected $R^{21}$, OR$^{21}$, SR$^{21}$, CN, CF$_3$, OCF$_3$, F, Cl, Br or I; and
$R^{21}$ is alkyl which is unsubstituted or substituted with one or two or three of independently selected F, Cl, Br, I, or OH.

10. The compound of claim 8, wherein $R^2$ is substituted with $R^{10}$,
$R^{10}$ is $R^{14}$;
$R^{14}$ is alkyl which is substituted with NHC(O)R$^{15}$ or NHC(O)NHR$^{15}$;
$R^{15}$ is $R^{16}$;
$R^{16}$ is phenyl;
wherein $R^{16}$ is unsubstituted or substituted with one or two or three of independently selected $R^{21}$, OR$^{21}$, SR$^{21}$, CN, CF$_3$, OCF$_3$, F, Cl, Br or I; and
$R^{21}$ is alkyl which is unsubstituted or substituted with one or two or three of independently selected F, Cl, Br, I, or OH.

11. The compound of claim 8, wherein $R^2$ is substituted with $NHC(O)R^{10}$;
$R^{10}$ is $R^{11}$ or $R^{12}$;
$R^{11}$ is phenyl;
$R^{12}$ is heteroaryl;
wherein the moieties represented by $R^{11}$ and $R^{12}$ are independently unsubstituted or substituted with one or two or three of independently selected $R^{21}$, $OR^{21}$, $SR^{21}$, CN, $CF_3$, $OCF_3$, F, Cl, Br or I; and
$R^{21}$ is alkyl which is unsubstituted or substituted with one or two or three of independently selected F, Cl, Br, I, or OH.

12. The compound of claim 1, wherein X is $NG^1$, and $G^1$ is H or alkyl.

13. The compound of claim 12, wherein $R^2$ is substituted with $NHC(O)NHR^{10}$;
$R^{10}$ is $R^{11}$ or $R^{12}$;
$R^{11}$ is phenyl;
$R^{12}$ is heteroaryl;
wherein the moieties represented by $R^{11}$ and $R^{12}$ are independently unsubstituted or substituted with one or two or three of independently selected $R^{21}$, $OR^{21}$, $SR^{21}$, CN, $CF_3$, $OCF_3$, F, Cl, Br or I; and
$R^{21}$ is alkyl which is unsubstituted or substituted with one or two or three of independently selected F, Cl, Br, I, or OH.

14. The compound of claim 12, wherein $R^2$ is substituted with $R^{10}$,
$R^{10}$ is $R^{14}$;
$R^{14}$ is alkyl which is substituted with $NHC(O)R^{15}$ or $NHC(O)NHR^{15}$;
$R^{15}$ is $R^{16}$;
$R^{16}$ is phenyl;
wherein $R^{16}$ is unsubstituted or substituted with one or two or three of independently selected $R^{21}$, $OR^{21}$, $SR^{21}$, CN, $CF_3$, $OCF_3$, F, Cl, Br or I; and
$R^{21}$ is alkyl which is unsubstituted or substituted with one or two or three of independently selected F, Cl, Br, I, or OH.

15. The compound of claim 12, wherein $R^2$ is substituted with $NHC(O)R^{10}$;
$R^{10}$ is $R^{11}$ or $R^{12}$;
$R^{11}$ is phenyl;
$R^{12}$ is heteroaryl;
wherein the moieties represented by $R^{11}$ and $R^{12}$ are independently unsubstituted or substituted with one or two or three of independently selected $R^{21}$, $OR^{21}$, $SR^{21}$, CN, $CF_3$, $OCF_3$, F, Cl, Br or I; and
$R^{21}$ is alkyl which is unsubstituted or substituted with one or two or three of independently selected F, Cl, Br, I, or OH.

* * * * *

UNITED STATES PATENT AND TRADEMARK OFFICE
CERTIFICATE OF CORRECTION

Page 1 of 2

PATENT NO. : 8,110,572 B2
APPLICATION NO. : 12/174334
DATED : February 7, 2012
INVENTOR(S) : Dai et al.

It is certified that error appears in the above-identified patent and that said Letters Patent is hereby corrected as shown below:

In the Claims:

Column 60, line 63, claim 1: "$R^{10}$,)N" to read as --$R^{10}$, N--

Column 60, line 64, claim 1: "$R^{10}$,)N" to read as --$R^{10}$, N--

Column 60, line 65, claim 1: "$(R^{10})_2$)C" to read as --$(R^{10})_2$, C--

Column 60, line 67, claim 1: "$R^{10}$,)S" to read as --$R^{10}$, S--

Column 61, line 15, claim 1: "alkenyl or alkenyl" to read as --alkenyl or alkynyl--

Column 61, line 40, claim 1: "alkenyl or alkenyl" to read as --alkenyl or alkynyl--

Column 61, line 44, claim 1: "$R^{12},R^{13}$," to read as --$R^{12}$, $R^{13}$,--

Column 61, line 44, claim 1: "$R^{16},R^{17}$," to read as --$R^{16}$, $R^{17}$,--

Column 61, line 49, claim 1: "NHC(O)R $^{21}$," to read as --NHC(O)$R^{21}$,--

Column 61, line 62, claim 1: "K is" to read as --is--

Column 62, line 59, claim 2: "andinocarbonyl" to read as --anilinocarbonyl--

Column 63, line 52, claim 2: "indazole -4" to read as --indazole-4--

Column 65, line 42, claim 2: "carboxamide ;" to read as --carboxamide;--

Column 66, line 12, claim 5: "$OR^{21}$; $SR^{21}$," to read as --$OR^{21}$, $SR^{21}$,--

Signed and Sealed this
Twenty-first Day of May, 2013

Teresa Stanek Rea
*Acting Director of the United States Patent and Trademark Office*

CERTIFICATE OF CORRECTION (continued)
U.S. Pat. No. 8,110,572 B2

Column 66, line 18, claim 6: "$R^{10}$," to read as --$R^{10}$;--

Column 66, line 56, claim 10: "$R^{10}$," to read as --$R^{10}$;--

Column 68, line 02, claim 14: "$R^{10}$," to read as --$R^{10}$;--